US008445447B2

(12) United States Patent
Chen

(10) Patent No.: US 8,445,447 B2
(45) Date of Patent: *May 21, 2013

(54) B7-DC VARIANTS IMMUNOGENIC COMPOSITIONS AND METHODS OF USE THEREOF

(75) Inventor: Lieping Chen, New Haven, CT (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/413,990

(22) Filed: Mar. 7, 2012

(65) Prior Publication Data

US 2012/0164168 A1    Jun. 28, 2012

Related U.S. Application Data

(63) Continuation of application No. 12/171,802, filed on Jul. 11, 2008, now Pat. No. 8,153,595.

(60) Provisional application No. 60/949,785, filed on Jul. 13, 2007.

(51) Int. Cl.
*A61K 38/16* (2006.01)

(52) U.S. Cl.
USPC ....................................... 514/21.2

(58) Field of Classification Search
None
See application file for complete search history.

(56) References Cited

U.S. PATENT DOCUMENTS

| 4,272,398 | A | 6/1981 | Jaffe |
| 4,376,110 | A | 3/1983 | David |
| 4,650,764 | A | 3/1987 | Temin |
| 4,769,330 | A | 9/1988 | Paoletti |
| 4,861,627 | A | 8/1989 | Mathiowitz |
| 4,861,719 | A | 8/1989 | Miller |
| 4,925,673 | A | 5/1990 | Steiner |
| 4,980,289 | A | 12/1990 | Temin |
| 5,013,556 | A | 5/1991 | Woodle |
| 5,124,263 | A | 6/1992 | Temin |
| 5,155,020 | A | 10/1992 | Paoletti |
| 5,155,027 | A | 10/1992 | Sledziewski |
| 5,175,099 | A | 12/1992 | Wills |
| 5,204,243 | A | 4/1993 | Paoletti |
| 5,225,336 | A | 7/1993 | Paoletti |
| 5,225,538 | A | 7/1993 | Capon |
| 5,240,846 | A | 8/1993 | Collins |
| 5,278,056 | A | 1/1994 | Bank |
| 5,284,656 | A | 2/1994 | Platz |
| 5,451,569 | A | 9/1995 | Wong |
| 5,521,288 | A | 5/1996 | Linsley |
| 5,567,584 | A | 10/1996 | Sledziewski |
| 5,675,848 | A | 10/1997 | Kappel |
| 5,714,147 | A | 2/1998 | Capon |
| 5,750,375 | A | 5/1998 | Sledziewski |
| 5,843,725 | A | 12/1998 | Sledziewski |
| 5,861,310 | A | 1/1999 | Freeman |
| 5,942,607 | A | 8/1999 | Freeman |
| 6,018,026 | A | 1/2000 | Sledziewski |
| 6,291,212 | B1 | 9/2001 | Sledziewski |
| 6,291,646 | B1 | 9/2001 | Sledziewski |
| 6,300,099 | B1 | 10/2001 | Sledziewski |
| 6,323,323 | B1 | 11/2001 | Sledziewski |
| 6,630,575 | B2 | 10/2003 | Coyle |
| 6,635,750 | B1 | 10/2003 | Coyle |
| 6,743,619 | B1 | 6/2004 | Tang |
| 6,919,193 | B2 | 7/2005 | Tang |
| 6,965,018 | B2 | 11/2005 | Mikesell |
| 7,029,674 | B2 | 4/2006 | Carreno |
| 7,030,219 | B2 | 4/2006 | Pardoll |
| 7,122,351 | B2 | 10/2006 | Moore |
| 7,279,567 | B2 | 10/2007 | Mikesell |
| 7,358,354 | B2 | 4/2008 | Mikesell |
| 7,368,531 | B2 | 5/2008 | Rosen |
| 7,381,794 | B2 | 6/2008 | Moore |
| 7,414,122 | B2 | 8/2008 | Fox |
| 7,432,059 | B2 | 10/2008 | Freeman |
| 7,432,062 | B2 | 10/2008 | Coyle |
| 7,432,351 | B1 | 10/2008 | Chen |
| 7,560,540 | B2 | 7/2009 | Pardoll |
| 7,563,869 | B2 | 7/2009 | Honjo |
| 7,595,048 | B2 | 9/2009 | Honjo |
| 7,709,214 | B2 | 5/2010 | Freeman |
| 7,723,479 | B2 | 5/2010 | Mikesell |

(Continued)

FOREIGN PATENT DOCUMENTS

| EP | 1074617 | 2/2001 |
| WO | 9007861 | 7/1990 |

(Continued)

OTHER PUBLICATIONS

Acsadi, et al., "Direct gene transfer and expression into rat heart in vivo", The New Biologist, 3:71-81 (1991).
Agata, et al., "Expression of the PD-1 antigen on the surface of stimulated mouse T and B lymphocytes", Int. Immunol., 8:765-772 (1996).
Aldovini and Young, "Humoral and cell-mediated immune responses to live recombinant BCG-HIV vaccines", Nature, 351:479-482 (1991).
Anderson, "Human gene therapy", Science, 256:808-813 (1992).
Attwood, et al., "Genomics. The babel of bioinformatics", Science, 290 (5491):471-3 (2000).
Bajorath, et al., "Molecular modeling of CD28 and three-dimensional analysis of residue conservation in the CD28/CD152 family", J. Mol. Graph. Model., 15:135-139, 108-11 (1997).

(Continued)

Primary Examiner — Ilia Ouspenski
(74) Attorney, Agent, or Firm — Pabst Patent Group LLP

(57) ABSTRACT

Compositions and methods for costimulating T cells (i.e., increasing antigen-specific proliferation of T cells, enhancing cytokine production by T cells, stimulating differentiation ad effector functions of T cells and/or promoting T cell survival) are provided. Suitable compositions include variant B7-DC polypeptides, fragments and fusion proteins thereof. Variant B7-DC polypeptides have reduced binding affinity for the inhibitory PD-1 ligand and substantially retain the ability to costimulate T cells. Methods for using variant B7-DC polypeptides to stimulate immune responses in subjects in need thereof are provided.

25 Claims, 10 Drawing Sheets

U.S. PATENT DOCUMENTS

| | | | |
|---|---|---|---|
| 8,039,589 B1 | 10/2011 | Chen | |
| 8,053,414 B2 | 11/2011 | Pardoll | |
| 8,053,558 B2 | 11/2011 | Pardoll | |
| 8,153,595 B2 * | 4/2012 | Chen | 514/21.2 |
| 2002/0091246 A1 | 7/2002 | Pardoll | |
| 2002/0095024 A1 | 7/2002 | Mikesell | |
| 2002/0106730 A1 | 8/2002 | Coyle | |
| 2002/0107363 A1 | 8/2002 | Fox | |
| 2002/0110836 A1 | 8/2002 | Freeman | |
| 2002/0164600 A1 | 11/2002 | Freeman | |
| 2003/0142359 A1 | 7/2003 | Bean | |
| 2003/0171551 A1 | 9/2003 | Rosenblatt | |
| 2003/0208058 A1 | 11/2003 | Fiscella | |
| 2003/0232323 A1 | 12/2003 | Freeman | |
| 2004/0010134 A1 | 1/2004 | Rosen | |
| 2005/0228170 A1 | 10/2005 | Fox | |
| 2005/0260716 A1 | 11/2005 | Moore | |
| 2006/0034826 A1 | 2/2006 | Carreno | |
| 2006/0084794 A1 | 4/2006 | Rosen | |
| 2006/0110383 A1 | 5/2006 | Honjo | |
| 2006/0159685 A1 | 7/2006 | Mikesell | |
| 2006/0223088 A1 | 10/2006 | Rosen | |
| 2007/0037206 A1 | 2/2007 | Rosen | |
| 2007/0041963 A1 | 2/2007 | Rosen | |
| 2007/0065427 A1 | 3/2007 | Freeman | |
| 2007/0092504 A1 | 4/2007 | Carreno | |
| 2007/0099833 A1 | 5/2007 | Rosen | |
| 2007/0122378 A1 | 5/2007 | Freeman | |
| 2007/0224663 A1 | 9/2007 | Rosen | |
| 2007/0231344 A1 | 10/2007 | Leadbetter | |
| 2008/0025979 A1 | 1/2008 | Honjo | |
| 2008/0118511 A1 | 5/2008 | Freeman | |
| 2008/0226662 A1 | 9/2008 | Pardoll | |
| 2008/0241175 A1 | 10/2008 | Pardoll | |
| 2009/0042292 A1 | 2/2009 | Chen | |
| 2009/0075338 A1 | 3/2009 | Moore | |
| 2009/0269783 A1 | 10/2009 | Coyle | |
| 2012/0065374 A1 | 3/2012 | Pardoll | |
| 2012/0065385 A1 | 3/2012 | Pardoll | |

FOREIGN PATENT DOCUMENTS

| | | |
|---|---|---|
| WO | 9110741 | 7/1991 |
| WO | 9117271 | 11/1991 |
| WO | 9200092 | 1/1992 |
| WO | 9201047 | 1/1992 |
| WO | 9220791 | 11/1992 |
| WO | 9301222 | 1/1993 |
| WO | 9505464 | 2/1995 |
| WO | 9507707 | 3/1995 |
| WO | 9717613 | 5/1997 |
| WO | 9717614 | 5/1997 |
| WO | 9724447 | 7/1997 |
| WO | 9823635 | 6/1998 |
| WO | 9833914 | 8/1998 |
| WO | 9964597 | 12/1999 |
| WO | 0055375 | 9/2000 |
| WO | 0061612 | 10/2000 |
| WO | 0134629 | 5/2001 |
| WO | 0170979 | 9/2001 |
| WO | 0183750 | 11/2001 |
| WO | 0194413 | 12/2001 |
| WO | 0200692 | 1/2002 |
| WO | 0200730 | 1/2002 |
| WO | 0202587 | 1/2002 |
| WO | 0202891 | 1/2002 |
| WO | 0208279 | 1/2002 |
| WO | 0278731 | 1/2002 |
| WO | 0224891 | 3/2002 |
| WO | 02057453 | 7/2002 |
| WO | 02079474 | 10/2002 |
| WO | 02081731 | 10/2002 |
| WO | 02086083 | 10/2002 |
| WO | 03008583 | 1/2003 |
| WO | 2006050172 | 5/2006 |
| WO | 2008037080 | 4/2008 |
| WO | 2008083174 | 7/2008 |
| WO | 2009023566 | 2/2009 |
| WO | 2009029342 | 3/2009 |
| WO | 2009114110 | 9/2009 |
| WO | 2010027423 | 3/2010 |
| WO | 2010027827 | 3/2010 |
| WO | 2010027828 | 3/2010 |
| WO | 2010098788 | 9/2010 |
| WO | 2011066342 | 6/2011 |

OTHER PUBLICATIONS

Benita, et al., "Characterization of drug-loaded poly(d,l-lactide) microspheres", J. PPharm. Sci., 73:1721-1724 (1984).

Berman, et al, "The Protein Data Bank", Nucl. Acids Res., 28:235-242 (2000).

Blazar, et al., "Infusion of anti-B7.1 (C080) and anti-B7.2 (CD86) monoclonal antibodies inhibits murine graft-versus-host disease lethality in part via direct effects on CD4+ and CD8+ T cells", Annu. Rev. Immunol., 24:175-208 (1996).

Blazer, et al., "Infusion of anti-B7.1 (CD80) and anti-B7.2 (CDB6) monoclonal antibodies inhibits murine graft-versus-host disease lethality in part via direct effects on CD4+ and CD8+ T cells", J. Immunol., 157:3250-59 (1996).

Bona and Hiernaux, et al., "Immune response: Idiotype anti-idiotype network", CRC Crit. Rev. Immunol., 33-81 (1981).

Bonifaz, et al., "Efficient targeting of protein antigen to the dendritic cell receptor DEC-205 in the steady state leads to antigen presentation on major histocompatibillty complex class I products and peripheral CD8+ T cell tolerance", J. Exp. Med., 196(12)1627-38 (2002).

Bonifaz, et al., "In vivo targeting of antigens to maturing dendritic cells via the DEC-205 receptor improves T cell vaccination", J. Exp. Med., 199(6):815-24 (2004).

Boon, et al., "Human T cell responses against melanoma", Ann. Rev. Immmunol., 24:175-208 (2006).

Braquet, et al., "Effect of endothelin-1 on blood pressure and bronchopulmonary system of the guinea pig", J. Cardiovascular Pharmacology, 13(S5):S143-S146 (1989).

Butte, et al, "Interaction of human PD-L1 and B7-1", Mol. Immunol., 45 (13):3567-72 (2008).

Chakrabarti, et al., "Vaccinia virus expression vector: coexpression of beta-galactosidase provides visual screening of recombinant virus plaques", Molec. Cell. Biol., 5:3403-3409 (1985).

Chambers and Allison, "Co-stimulation in T cell responses", Curr. Opin. Immunol., 9:396-404 (1997).

Chapoval, et al., B7-H3: a costimulatory molecule for T cell activation and IFN-gamma production, Nat. Immunol., 2(3):269-74 (2001).

Chen, et al., "Costimulation of antitumor immunity by the B7 counterreceptor of the T lymphocyte molecules CD 28 and CTLA-4", Cell, 71:1093-1102 (1992).

Chen, "Co-inhibitory molecules of the B7-CD28 family in the control of T-cell Immunity", Nat. Rev. Immunol., 4(5):33647 (2004).

Choi, et al., "Genomic organization and expression analysis of B7-H4, an immune inhibitory molecule of the B7 family", J. Immunol, 171:4650-4 (2003).

Cone, et al., "High-efficiency gene transfer into mammalian cells: generation of helper-free recombinant retrovirus with broad mammalian host range", Proc. Natl. Acad. Sci. USA, 81:6349-6353 (1984).

Coyle, et al., "The expanding B7 superfamily: increasing complexity in costimulatory signals regulating T cell function", Nat. Immunol., 2(3):203-9 (2001).

Crystal, "Gene therapy strategies for pulmonary disease", Am. J. Med., 92 (6A):443-52S (1992).

Database EM-HUM [Online] EMBL; Accession No. AK001872 (Feb. 22, 2000).

Database EM-MUS [Online] EMBL; Accession No. AF142780.1 (version 1), (Jun. 1, 1999).

Debs, et al., "Lung-specific delivery of cytokines induces sustained pulmonary and systemic immunomodulation in rat", J. Immunol., 140:3482-3488 (1988).

Dong, et al., "B7-H1, a third member of the B7 family, co-stimulates T-cell proliferation and interleukin-10 secretion", Nature Med., 5(12):1365-1369 (1999).

Dong, et al., "Immune regulation by novel costimulatory molecules", Immunol. Res., 28(1):39-48 (2003).

Dong, et al., "Tumor-associated B7-H1 promotes T-cell apoptosis: a potential mechanism of immune evasion", Nature Med., 8:793-800 (2002).

Dudler, et al., "Gene transfer of programmed death ligand-1.lg prolongs cardiac allograft survival", Transplantation, 82(12):1733-7 (2006).

Dunussi-Joannopoulos, et al., "Gene therapy with B7.1 and GM-CSF vaccines in a murine AML model", J. Pediatr. Hematol. Oncol., 19(6):536-540 (1997).

EMBL-EBI Accession No. AF142780.2 (version 2, accessed Sep. 28, 2009), (Jun. 1, 1999).

EMBL-EBI Accession No. Q9WUL5 (Nov. 1, 1999).

Esteva, "Monoclonal antibodies, small molecules, and vaccines in the treatment of breast cancer", Oncologist, 9 Supp 3:4-9 (2004).

European Examination Report for Bristol-Myers Squibb Co., App. No. 07 023 993.4-1521, Dated May 19, 2010.

Falkner, et al., "pUV I: a new vaccinia virus insertion and expression vector", Nucl. Acids Res, 15:7192 (1987).

Fechteler, et al., "Prediction of protein three-dimensional structures in insertion and deletion regions: a procedure for searching data bases of representative protein fragments using geometric scoring criteria", J. Mol. Biol., 253:114-131 (1995).

Freeman, et al., "B7, a new member of the Ig superfamily with unique expression on activated and neoplastic B cells", The Journal of Immunology, 143 (8):2714-2722 (1989).

Freeman, et al., "Cloning of B7-2: a CTLA-4 counter-receptor that costimulates human T cell proliferation", Science, 262:909-911 (1993).

Freeman, et al., "Engagement of the PD-1 immunoinhibitory receptor by a novel B7 family member leads to negative regulation of lymphocyte activation", J. Exp. Med., 192:1027-1034 (2000).

Freeman, et al., "Structure, expression, and T cell costimulatory activity of the murine homologue of the human B lymphocyte activation antigen 87", J. Exp. Med., 174:625-631 (1991).

Fuerst, et al., "Transfer of the inducible lac repressor/operator system from *Escherichia coli* to a vaccinia virus expression vector", Proc. Natl. Acad. Sci. USA, 86:2549-2553 (1989).

GenBank Accession No. AK001872.1, "*Homo sapiens* cDNA FLJ11010 fis, clone PLACE1003145", pp. 1-2, (submitted Feb. 16, 2000).

GenBank Accession No. AL162253, "Human DNA sequence from clone RP11-574F11 on chromosome 9 Contains the gene for B7-H1 protein (PD-L1), the gene for programmed death ligand 2 (PDL2) (PDCD1L2) and a novel gene", pp. 1-36 (Mar. 24, 2000).

Gerstmayer, et al., "Costimulation of T-cell proliferation by a chimeric B7-antibody fusion protein", Cancer Immunology Immunotherapy, 45(3-4):156-158 (1997).

Gerstmayer, et al., "Costimulation of T cell proliferation by a chimeric B7-2 antibody fusion protein specifically targeted to cells expressing the erbB2 proto-oncogene," J. Immunol., 158(10): 4584-90 (1997).

Gimmi, et al., "B-cell surface antigen B7 provides a costimulatory signal that induces T cells to proliferate and secrete interleukin 2", Proc. Natl. Acad. Sci., 88:6576-6570 (1991).

Goodwin, et al., "Molecular Cloning and Expression of the Type 1 and Type 2 Murine Receptors for the Tumor Necrosis Factor", Mol. and Cell. Biol., 11 (6):3020-3026 (1991).

Greenwald, et al., "The B7 family revisited", Annu. Rev. Immunol., 23:515-48 (2005).

Guatelli, et al., "Isothermal, in vitro amplification of nucleic acids by a multienzyme reaction modeled after retroviral replication", Proc. Natl. Acad. Sci. USA, 87:1874-1878 (1990).

Guo, et al., "A novel fusion protein of IP10-scFv retains antibody specificity and chemokine function," Biochem. Biophys. Res. Commun., 320(2):506-13 (2004).

Hatzoglou, et al., "Hepatic gene transfer in animals using retroviruses containing the promoter from the gene for phosphoenolpyruvate carboxykinase", J. Biol. Chem. 265:17285-93 (1990).

Hawiger, et al., "Dendritic cells induce peripheral T cell unresponsiveness under steady state conditions in vivo", J. Exp. Med., 194(6):769-79 (2001).

Henry, et al., "Cloning, structural analysis, and mapping of the B30 and B7 multigen families to the major histocompatibility complex (MHC) and other chromosomal regions", Immunogenetics, 46:386-395 (1997).

Henry., et al., "Structure and evolution of the extended B7 family", Immunology Today, 20(6):285-288 (1999).

Hentikoff and Hentikoff, "Amino acid substitution matrices from protein blocks", Proc. Natl. Acad. Sci. U.S.A., 89:10915-10919 (1992).

Hiroishi, et al., "Interferon-alpha gene therapy in combination with CD80 transduction reduces tumorigenicity and growth of established tumor in poorly immunogenic tumor models", Gene Ther., 6:1988-1994 (1999).

Hochman, et al., "An active antibody fragment (Fv) composed of the variable portions of heavy and light chains", Biochemistry, 12:1130-1135 (1973).

Hock, et al., "Retrovirus-mediated transfer and expression of drug resistance genes in human haematopoietic progenitor cells", Nature, 320:275-77 (1986).

Hoiseth and Stocker, "Aromatic-dependent *Salmonella typhimurium* are non-virulent and effective as live vaccines", Nature, 291, 238-239 (1981).

Hubbard, et al., "Anti-neutrophil-elastase defenses of the lower respiratory tract in alpha 1-antitrypsin deficiency directly augmented with an aerosol of alpha 1-antitrypsin", Ann. Intern. Med., 111(3):206-12 (1989).

Hyrup, et al., "Peptide nucleic acids (PNA): synthesis, properties and potential applications", Bioorgan. Med, Chem., 4:5-23 (1996).

Ikemizu, et al., "Structure and dimerization of a soluble form of B7-1", Immunity, 12:51-60 (2000).

Ikonomidis, "Delivery of a viral antigen to the class I processing and presentation pathway by *Listeria monocytogenes*", J. Exp. Med., 180:2209-2218 (1994).

Ishida, et al., "Differential expression of PD-L1 and PD-L2, ligands for an inhibitory receptor PD-1, in the cells of lymphohematopoietic tissues", Immunol. Lett., 84:57-62 (2002).

Ishida, et al., "Induced expression of PD-1, a novel member of the immunoglobulin gene superfamily, upon programmed cell death", EMBO J., 11:3887-3895 (1992).

Jerne, "Towards a network theory of the immune system" Ann. Immunol., 125C:373-389 (1974).

Johnston, et al., "Biolistic Transformation of Animal Tissue", In Vitro Cell. Dev. Biol., 27P:11-14 (1991).

Kaleko, et al., "Persistent gene expression after retroviral gene transfer into liver cells in vivo", Human Gene Therapy, 2:27-32 (1991).

Kaufman, et al., "A phase I trial of intra lesional RV-B7.1 vaccine in the treatment of malignant melanoma", Hum. Gene Ther., 11:1065-1082 (2000).

Kohler and Milstein, "Continuous cultures of fused cells secreting antibody of predefined specificity", Nature, 256:495-497 (1975).

Kohn, et al., "Gene therapy for genetic diseases", Cancer Invest., 7:179-192 (1989).

Krummel and Allison, "CTLA-4 engagement inhibits IL-2 accumulation and cell cycle progression upon activation of resting T cells", J. Exp. Med., 183:2533-2540 (1996).

Kuiper, et al., "B7.1 and cytokines. Synergy in cancer gene therapy", Adv. Exp. Med. Biol., 465:381-390 (2000).

Latchman, et al., "PD-L2 is a second ligand for PD-1 and inhibits T cell activation", Nature Immunol., 2(3):261-268 (2001).

Lee, et al., "Increased vaccine-specific T cell frequency after peptide-based vaccination correlates with increased susceptibility to in vitro stimulation but does not lead to tumor regression", J Immunology, 163:6292-6300 (1999).

Lenschow, et al., "Expression and functional significance of an additional ligand for CTLA-4", Proc. Natl. Acad. Sci., 90:11054-11058 (1993).

Lenshow, et al., "CD28/B7 system of T cell costimulation", Annu. Rev. Immunol., 14:233-258 (1996).

Levitt, "Accurate modeling of protein conformation by automatic segment matching", J. Mol. Biol., 226:507-533 (1992),.

Lewinski, et al., "Retroviral DNA integration: viral and cellular determinants of target-site selection," PLoS Pathog., 2(6):e60 (2006).

Linsley, et al., "Binding of the B cells activation antigen B7 to CD28 costimulates T cell proliferation and interleukin 2 mRNA accumulation", J. Exp. Med., 173:721-730 (1991).
Linsley, et al. "Extending the B7 (CD80) gene family", Protein Sci., 3 (8):1341-1343 (1994).
Linsley, et al., "T-cell antigen CD28 mediates adhesion with B cells by interacting with activation antigen 87188-1", Proc. Natl. Acad. Sci., 87:5031-5035 (1990).
Liu, et al., "B7DC/PDL2 promotes tumor immunity by a PD-1-independent mechanism", J. Exp. Med., 197(12):1721-30 (2003).
Lu, et al., "EGF-IL-18 fusion protein as a potential anti-tumor reagent by induction of immune response and apoptosis in cancer cells," Cancer Lett., 60(1-2):187-97 (2008) {E-Published Dec. 21, 2007}.
Mann, et al., "Construction of a retrovirus packaging mutant and its use to produce helper-free defective retrovirus", Cell, 33:153-159 (1983).
Martin, et al.,"Combination gene therapy with CD86 and the MHC class II transactivator in the control of lung tumor growth", J. Immunol., 162:6663-6670 (1999).
Mathiowitz, et al., "Morphology of polyanhydride microsphere delivery systems", Scanning Microscopy,4:329-340 (1990).
Mathiowitz, et al., "Polyanhydride microspheres. IV. Morphology and characterization of systems made by spray drying", J. Appl. Polymer Sci. 45:125-134 (1992).
Mathiowitz, "Novel microcapsules for delivery systems", Reactive Polymers, 6:275-283 (1987).
Mathiowitz, "Polyanhydride microspheres as drug carriers. II. microencapsulation by solvent removal", J. Appl. Polymer Sci., 35:755-774 (1988).
Mathiowitz and Langer, "Polyanhydride microspheres as drug carriers. I. Hot-melt microencapsulation", J. Controlled Release, 5:13-22 (1987).
McLachlin, et al., "Retroviral-mediated gene transfer", Prog. Nuc. Acid Res. Molec. Biol. 38:91-135 (1990).
Metzler, et al., "Solution structure of human CTLA-4 and delineation of a CD80/CD86 binding site conserved in CD28", Nat. Struct. Biol., 4(7):527-31 (1997).
Miller, et al., Gene transfer by retrovirus vectors occurs only in cells that are actively replicating at the time of infection, Mol. Cell. Biol., 10:4239 (1990).
Miller, et al., "Generation of helper-free amphotropic retroviruses that transduce a dominant-acting, methotrexate-resistant dihydrofolate reductase gene", Molec. Cell. Biol., 5:431-437 (1985).
Miller, et al., "Redesign of retrovirus packaging cell lines to avoid recombination leading to helper virus production", Molec. Cell. Biol., 6:2895-2902 (1986).
Miller, "Human gene therapy comes of age", Nature, 357:455-460 (1992).
Moss, "Poxvirus expression vectors", Curr. Top. Microbiol. Immunol., 158:25-38 (1992).
Moss, "Poxvirus vectors: cytoplasmic expression of transferred genes", Curr. Opin. Genet. Dev., 3:86-90 (1993).
Moss, "Use of vaccinia virus as an infectious molecular cloning and expression vector", Gene Amplif Anal 3:201-213 (1983).
Moss, "Vaccinia virus: a tool for research and vaccine development", Science 252:1662-1667 (1991).
Moss, "Vaccinia virus vectors", in Vaccines: New Approaches to Immunological Problems, (Ellis, ed.), Butterworth-Heinemann:Boston, MA, pp. 345-362 (1992).
Nabel, et al., "Recombinant gene expression in vivo within endothelial cells of the arterial wall", Science, 244(4910):1342-4 (1989).
Nechiporuk, et al., "The mouse SCA2 gene: cDNA sequence, alternative splicing and protein expression", Human Mol. Gen., 7(8):1301-1309 (1998).
Needleman and Wunsch, "A general method applicable to the search for similarities in the amino acid sequence of two proteins", J. Mol. Biol., 48:443-453 (1970).
Newmark, et al., "Preparation and properties of adducts of streptokinase and streptokinase-plasmin complex with polyethylene glycol and pluronic Polyol F38", J. Appl. Biochem., 4:185-189 (1982).
Nicolau, et al., "In vivo expression of rat insulin after intravenous administration of the liposome-entrapped gene for rat insulin I", Proc. Natl. Acad. Sci. USA, 80:1068-72 (1983).
Nielsen and Marincola, "Melanoma vaccines: the paradox of T cell activation without clinical response", Cancer Chemother. Pharmacol., 46 (Suppl):S62-S66 (2006).
Nishimura, et al., "Autoimmune dilated cardiomyopathy in PD-1 receptor-deficient deficient mice", Science 291:319-322 (2001).
Nishimura, et al., "Development of lupus-like autoimmune diseases by disruption of the PD-1 gene encoding an ITIM motif-carrying immunoreceptor", Immunity, 11:141-151 (1999).
Nishimura, et al., "Immunological studies on PD-1 deficient mice: implication of PD-1 as a negative regulator for B cell responses", Int. Immunol., 10:1563-1572 (1998).
Office Action in U.S. Appl. No. 09/794,210 mailed Dec. 3, 2003.
Office Action in U.S. Appl. No. 09/794,210 mailed Jan. 9,2003.
Office Action in U.S. Appl. No. 11/361,057 mailed Aug. 17, 2007.
Office Action in U.S. Appl. No. 11/361,057 mailed Feb. 23, 2007.
Office Action in U.S. Appl. No. 11/361,057 mailed Jan. 17, 2008.
Office Action in U.S. Appl. No. 11/361,057 mailed Oct. 24, 2008.
Office Action in U.S. Appl. No. 11/931,653 mailed Jul. 14, 2010.
Office Action in U.S. Appl. No. 11/931,653 mailed Mar. 24, 2011.
Office Action in U.S. Appl. No. 11/932,327 mailed Jul. 15, 2010.
Office Action in U.S. Appl. No. 11/932,471 mailed Apr. 20, 2010.
Office Action in U.S. Appl. No. 11/932,471 mailed Jan. 6, 2011.
Office Action in U.S. Appl. No. 11/932,327 mailed May 12, 2011.
Okazaki, et al., "PD-1 and PD-1 ligands: from discovery to clinical application", Int. lmmunl., 19(7):813-24 (2007).
Ostrov, et al., "Structure of murine CTLA-4 and its role in modulating T cell responsiveness", Science, 290:816-819 (2000).
Ozkaynak, "Programmed death-1 targeting can promote allograft survival", J. Immunol., 169(11):6546-53 (2002).
Peach, et al., "Both extracellular immunoglobin-like domains of CD80 contain residues critical for binding T cell surface receptors CTLA-4 and CD28", J. Biol. Chem,., 270(36):21181-21187 (1995).
Penix, et al., Two essential regulatory elements in the human interferon gamma promoter confer activation specific expression in T cells, J. Exp. Med. 178:1483-1496 (1993).
Piccini and Paoletti, "Vaccinia: virus, vector, vaccine", Adv. Virus Res., 34:43-64 (1988).vbTab.
Pluckthun, "Expression of functional antibody Fv and Fab fragments in *Escherichia coli*", Methods Enzymol., 178: 497-515 (1989).
Poirier, "Protective immunity evoked by oral administration of attenuated aroA *Salmonella typhimurium* expressing cloned streptococcal M protein", J. Exp. Med., 168:25-32 (1988).
Ponder and Richards, "Tertiary templates for proteins. Use of packing criteria in the enumeration of allowed sequences for different structural classes", J. Mol. Biol., 193:775-791 (1987).
Prasad, et al., "B7S1, a novel B7 family member that negatively regulates T cell activation", Immunity, 18(6):863-873 (2003).
Radhakrishnan, et al., "Dendritic cells activated by cross-linking B7-DC (PD-L2) block inflammatory airway disease", J. Allergy Clin. Immunol., 116(3):668-74 (2005).
Rajewsky, et al., "Genetics, expression, and function of idiotypes", Ann. Rev. Immunol., 1:569-607 (1983).
Rathmell and Thompson, "The central effectors of cell death in the immune system", Annu. Rev. Immunol., 17:781-828 (1999).
Razi-Wolf, "Expression and function of the murine B7 antigen, the major costimulatory molecule expressed by peritoneal exudate cells", Proc. Natl. Acad. Sci., 89:4210-4214 (1992).
Renauld, et al., "Expression cloning of the murine and human interleukin 9 receptor cDNAs", Proc. Natl. Acad. Sci. USA, 89:5690-5694 (1992).
Rosenfeld, et al., "Adenovirus-mediated transfer of a recombinant alpha 1-antitrypsin gene to the lung epithelium in vivo", Science, 252:431-3 (1991).
Rousseaux, "Optimal conditions for the preparation of proteolytic fragments from monoclonal IgG of different rat IgG subclasses", Meth. Enzymol., 121:663-69 (1986).
Sadoff, "Oral *Salmonella typhimurium* vaccine expressing circumsporozoite protein protects against malaria", Science, 240:336-338 (1988).

Salib, et al., "Utilization of sodium alginate in drug microencapsulation", Pharmazeutische Industrie, 40(11A):1230-34 (1978).

Salih, et al., "The role of leukemia-derived B7-H1 (PD-L1) in tumor-T-cell interactions in humans", Exp. Hematol, 34(7):888-94 (2006).

Samulski, "Targeted integration of adeno-associated virus (AAV) into human chromosome 19", EMBO J., 10:3941-3950 (1991).

Sanni, et al., "Evolution of aminoacyl-tRNA synthetase quaternary structure and activity: *Saccharomyces cerevisiae* mitochondrial phenylalanyl-tRNA synthetase", Proc. Natl. Acad. Sci. USA, 88:8387-91 (1991).

Sawhney, et al., "Bioerodible hydrogels based on photopolymerized poly (ethylene glycol)-co-poly(.alpha.-hydroxy acid) diacrylate macromers", Macromolecules, 26:581-587 (1993).

Schafer, et al., "Induction of a cellular immune response to a foreign antigen by a recombinant *Listeria monocytogenes* vaccine", J. Immunol., 149:53-59 (1992).

Schwartz, et al., "Costimulation of T lymphocytes: the role of CD28. CTLA-4, and B7/BBI in interluekin-2 production and immunotherapy", Cell, 71:1065-1068 (1992).

Schwartz, et al., "Structural basis for co-stimulation by the human CTLA-4/B7-2 complex", Nature, 410:604-608 (2001).

Schwartz, et al., "Structural mechanisms of costimulation", Nature Immunol., 3:427 434 (2002).

Sharon, et al., "Preparation of Fv fragment from the mouse myeloma XRPC-25 immunoglobulin possessing anti-dinitrophenyl activity", Biochemistry, 15:1591-1594 (1976).

Shin, et al., "Cooperative B-7-1/2 (CD80/CD86) and B7-DC costimulation of CD4+ T cells independent of the PD-1 receptor", J. Exp. Med., 198(1):31-38 (2003).

Sica, et al., "B7-H4, a molecule of the B7 family, negatively regulates T cell immunity", Immunity, 18:849-861 (2003).

Skerra, "Assembly of a functional immunoglobulin Fv fragment in *Escherichiacoli*", Science, 240:1038-41 (1988).

Skolnick, et al., "From genes to protein structure and function: novel applications of computational approaches in the genomic era", Trends Biotechnol., 18(1):34-9 (2000).

Smith, et al., "Pulmonary deposition and clearance of aerosolized alpha-1-proteinase inhibitor administered to dogs and to sheep", J. Clin. Invest., 84:1145-1146 (1989).

Sorge, et al., "Amphotropic retrovirus vector system for human cell gene transfer", Molec. Cell. Biol., 4:1730-1737 (1984).

Soriano, "Targeted and nontargeted liposomes for in vivo transfer to rat liver cells of a plasmid containing the preproinsulin I gene", Proc. Natl. Acad. Sci. USA, 80:7128-7131 (1983).

Stammers, et al., "BTL-II: A polymorphic locus with homology to the butyrolphilin gene family, located at the border of the major histocompatibility complex class II and class III regions in human and mouse", Immunogenetics, 51(4-5):373-382 (2000).

Stamper, et al., "Crystal structure of the B7-1/CTLA-4 complex that inhibits human immune responses", Nature, 410:608-611 (2001).

Subudhi, et al., "Local expression of B7-H1 promotes organ-specific autoimmunity and transplant rejection", J. Clin.Invest., 113(5):694-700 (2004).

Summerton and Weller, "Morpholino antisense oligomers: design, preparation, and properties", Antisense Nucleic Acid Drug Dev. 7:187-195 (1997).

Sutter, et al., "Nonreplicating vaccinia vector efficiently expresses recombinant genes", Proc. Natl. Acad. Sci. USA, 89:10847-10851 (1992).

Swallow, et al., "B7h, a novel costimulatory homolog of B7.1 and B7.2, is induced by TNFalpha", Immunity, 11:423-432 (1999).

Tamura, "B7-H1 costimulation preferentially enhances CD28-independent T-helper cell function", Blood, 97:1809-1816 (2001).

Tazi-Ahnini et al., "Cloning, localization, and structure of new members of the butyrophilin gene family in the juxta-telomeric region of the major histocompatibility complex", Immunogenetics, 47:55-63 (1997).

Temin, "Safety Considerations in Somatic Gene Therapy of Human Disease with Retrovirus Vectors", Human Gene Therapy, 1:111-23 (1990).

Thompson, et al., "Cis-acting sequences required for inducible interleukin-2 enhancer function bind a novel Ets-related protein, Elf-1", Mol. Cell. Biol. 12:1043-1053 (1992).

Titomirov, "In vivo electroporation and stable transformation of skin cells of newborn mice by plasmid DNA", Biochim. Biophys. Acta., 1088:131-134 (1991).

Todd, et al., "Transcription of the interleukin 4 gene is regulated by multiple promoter elements", J. Exp. Med. 177:1663-1674 1993).

Townsend, et al. "Tumor rejection after direct costimulation of CD8+T cells by B7-transfected melanoma cells", Science, 259:368-370 (1993).

Tseng, et al., "B7-DC, a new dendritic cell molecule with potent costimulatory properties for T cells", J. Exp. Med., 193:839-846 (2001).

Wahl, et al., "Improved radioimaging and tumor localization with monoclonal F (ab')2", J. Nuc. Med., 24:316-325 (1983).

Walunas, et al., "CTLA-4 ligation blocks CD28-dependent T cell activation", J. Exp. Med., 183:2541-2550 (1996).

Wang, et al., "Costimulation of T cells by B7-H2, a B7-like molecule that binds ICOS", Blood, 96:2808-2813 (2000).

Wang, et al., "Ligand binding sites of inducible costimulator and high avidity mutants with improved function", J. Exp. Med., 195:1033-1041 (2002).

Wang, et al., "Molecular modeling and functional mapping of B7-H1 and B7-DC uncouple costimulatory function from PD-1 interaction", J. Exp. Med., 197 (9):1083-91 (2003).

Wang and Huang, "pH-sensitive immunoliposomes mediate target-cell-specific delivery and controlled expression of a foreign gene in mouse", Proc. Natl. Acad. Sci. USA, 84:7851 (1987).

Weiss, "Hot prospect for new gene amplifier", Science 254:1292-1293 (1991).

Williams, et al., "Introduction of foreign genes into tissues of living mice by DNA-coated microprojectiles", Proc. Natl. Acad. Sci. USA, 88:2726 (1991).

Williams and Barclay, "The immunoglobulin superfamily—domains for cell surface recognition", Annu. Rev. Immunol., 6:381-405 (1988).

Winter, et al., "Man-made antibodies", Nature, 349:293-299 (1991).

Wolff, "Direct gene transfer into mouse muscle in vivo", Science, 247:1465-1468 (1990).

Wong, "Human GM-CSF: molecular cloning of the complementary DNA and purification of the natural and recombinant proteins", Science, 228(4701):810-815 (1985).

Wu, "Receptor-mediated gene delivery and expression in vivo", J. Biol. Chem., 263:14621-14624 (1988).

Wu, "Targeting genes: delivery and persistent expression of a foreign gene driven by mammalian regulatory elements in vivo", J. Biol. Chem., 264:16985-16987 (1989).

Yang, et al., "In vivo and in vitro gene transfer to mammalian somatic cells by particle bombardment", Proc. Natl. Acad. Sci. USA, 87:9568-72 (1990).

Yang, "Gene transfer into mammalian somatic cells in vivo", Crit. Rev. Biotechnol., 12:335-356 (1992).

Yoshinaga, et al., "T-cell co-stimulation through B7RP-1 and ICOS", Nature, 402:827-832 (1999).

Youngnak, et al., "Differential binding properties of B7-H1 and B7-DC to programmed death-1", Biochem. Biophys. Res. Commun., 307(3):672-77 (2003).

Zang, et al., "B7x: A widely expressed 87 family member that inhibits T cell activation", Proc. Natl. Acad. Sci. USA, 100(18):10388-10392 (2003).

Zelenin, et al, "Genetic transformation of mouse cultured cells with the help of high-velocity mechanical DNA injection", FEBS Lett., 244:65-7 (1989).

Zelenin, et al., "High-velocity mechanical DNA transfer of the chloramphenicolacetyl transferase gene into rodent liver, kidney and mammary gland cells in organ explants and in vivo", FEBS Lett., 280:94-6 (1991).

Zhou, et al., "Inducible-costimulator-mediated suppression of human immunodeficiency virus type 1 replication in CD4+ T lymphocytes", Virology, 325 (2):252-263 (2004).

Zwiebel, et al., "Drug delivery by genetically engineered cell implants", Ann. N.Y. Acad. Sci., 618:394-404 (1991).

* cited by examiner

MetIlePheLeuLeuLeuMetLeuSerLeuGluLeuGlnLeuHisGlnIleAlaAla
LeuPheThrValThrValProLysGluLeuTyrIleIleGluHisGlySerAsnVal
TheLeuGluCysAsnPheAspThrGlySerHisValAsnLeuGlyAlaIleThrAla
SerLeuGlnLysValGluAsnAspThrSerProHisArgGluArgAlaThrLeuLeu
GluGluGlnLeuProLeuGlyLysAlaSerPheHisIleProGlnValGlnValArg
AspGluGlyGlnTyrGlnCysIleIleIleTyrGlyValAlaTrpAspTyrLysTyr
LeuThrLeuLysValLysAlaSerTyrArgLysIleAsnThrHisIleLeuLysVal
ProGluThrAspGluValGluLeuThrCysGlnAlaThrGlyTyrProLeuAlaGlu
ValSerTrpProAsnValSerValProAlaAsnThrSerHisSerArgThrProGlu
GlyLeuTyrGlnValThrSerValLeuArgLeuLysProProProGlyArgAsnPhe
SerCysValPheTrpAsnThrHisValArgGluLeuThrLeuAlaSerIleAspLeu
GlnSerGlnMetGluProArgThrHisProThrTrpLeuLeuHisIlePheIlePro
SerCysIleIleAlaPheIlePheIleAlaThrValIleAlaLeuArgLysGlnLeu
CysGlnLysLeuTyrSerSerLysAspThrThrLysArgProValThrThrThrLys
ArgGluValAsnSerAlaIle (SEQ ID NO: 1)

FIG. 1

MetLeuLeuLeuLeuProIleLeuAsnLeuSerLeuGlnLeuHisProValAlaAla
LeuPheThrValThrAlaProLysGluValTyrThrValAspValGlySerSerVal
SerLeuGluCysAspPheAspArgArgGluCysThrGluLeuGluGlyIleArgAla
SerLeuGlnLysValGluAsnAspThrSerLeuGlnSerGluArgAlaThrLeuLeu
GluGluGlnLeuProLeuGlyLysAlaLeuPheHisIleProSerValGlnValArg
AspSerGlyGlnTyrArgCysLeuValIleCysGlyAlaAlaTrpAspTyrLysTyr
LeuThrValLysValLysAlaSerTyrMetArgIleAspThrArgIleLeuGluVal
ProGlyThrGlyGluValGlnLeuThrCysGlnAlaArgGlyTyrProLeuAlaGlu
ValSerTrpGlnAsnValSerValProAlaAsnThrSerHisIleArgThrProGlu
GlyLeuTyrGlnValThrSerValLeuArgLeuLysProGlnProSerArgAsnPhe
SerCysMetPheTrpAsnAlaHisMetLysGluLeuThrSerAlaIleIleAspPro
LeuSerArgMetGluProLysValProArgThrTrpProLeuHisValPheIlePro
AlaCysThrIleAlaLeuIlePheLeuAlaIleValIleIleGlnArgLysArgIle (SEQ ID NO: 2)

FIG. 2

```
atgatcttcc tcctgctaat gttgagcctg gaattgcagc ttcaccagat
agcagcttta ttcacagtga cagtccctaa ggaactgtac ataatagagc
atggcagcaa tgtgaccctg gaatgcaact ttgacactgg aagtcatgtg
aaccttggag caataacagc cagtttgcaa aaggtggaaa atgatacatc
cccacaccgt gaaagagcca ctttgctgga ggagcagctg cccctaggga
aggcctcgtt ccacatacct caagtccaag tgaggacga aggacagtac
caatgcataa tcatctatgg ggtcgcctgg gactacaagt acctgactct
gaaagtcaaa gcttcctaca ggaaaataaa cactcacatc ctaaaggttc
cagaaacaga tgaggtagag ctcacctgcc aggctacagg ttatcctctg
gcagaagtat cctggccaaa cgtcagcgtt cctgccaaca ccagccactc
caggaccct gaaggcctct accaggtcac cagtgttctg cgcctaaagc
cacccctgg cagaaacttc agctgtgtgt tctggaatac tcacgtgagg
gaacttactt tggccagcat tgaccttcaa agtcagatgg aacccaggac
ccatccaact tggctgcttc acattttcat cccctcctgc atcattgctt
tcatttcat agccacagtg atagccctaa gaaacaact ctgtcaaaag
ctgtattctt caaagacac aacaaaaga cctgtcacca caacaaagag
ggaagtgaac agtgctatct ga
```

(SEQ ID NO: 3)

FIG. 3

```
atgctgctcc tgctgccgat actgaacctg agcttacaac ttcatcctgt
agcagcttta ttcaccgtga cagcccctaa agaagtgtac accgtagacg
tcggcagcag tgtgagcctg gagtgcgatt ttgaccgcag agaatgcact
gaactggaag ggataagagc cagtttgcag aaggtagaaa atgatacgtc
tctgcaaagt gaaagagcca ccctgctgga ggagcagctg cccctgggaa
aggctttgtt ccacatccct agtgtccaag tgagagattc cgggcagtac
cgttgcctgg tcatctgcgg ggccgcctgg gactacaagt acctgacggt
gaaagtcaaa gcttcttaca tgaggataga cactaggatc ctggaggttc
caggtacagg ggaggtgcag cttacctgcc aggctagagg ttatccccta
gcagaagtgt cctggcaaaa tgtcagtgtt cctgccaaca ccagccacat
caggaccccc gaaggcctct accaggtcac cagtgttctg cgcctcaagc
ctcagcctag cagaaacttc agctgcatgt tctggaatgc tcacatgaag
gagctgactt cagccatcat tgaccctctg agtcggatgg aacccaaagt
ccccagaacg tggccacttc atgttttcat ccggcctgc aacatcgctt
tgatcttcct ggccatagtg ataatccaga gaaagaggat ctag
```

(SEQ ID NO: 4)

Days after tumor inoculation

SEQUENCE LISTING

<160> NUMBER OF SEQ ID NOS: 12

<210> SEQ ID NO 1
<211> LENGTH: 273
<212> TYPE: PRT
<213> ORGANISM: Homo Sapien

<400> SEQUENCE: 1

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
                100                 105                 110

Lys Tyr Leu Thr Leu Lys Val Lys Ala Ser Tyr Arg Lys Ile Asn Thr
            115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Gly Arg Asn Phe Ser Cys
            180                 185                 190

Val Phe Trp Asn Thr His Val Arg Glu Leu Thr Leu Ala Ser Ile Asp
            195                 200                 205

Leu Gln Ser Gln Met Glu Pro Arg Thr His Pro Thr Trp Leu Leu His
    210                 215                 220

Ile Phe Ile Pro Ser Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
                260                 265                 270

Ile

<210> SEQ ID NO 2
<211> LENGTH: 247
<212> TYPE: PRT
<213> ORGANISM: Mus musculus

<400> SEQUENCE: 2

Met Leu Leu Leu Leu Pro Ile Leu Asn Leu Ser Leu Gln Leu His Pro
1               5                   10                  15

Val Ala Ala Leu Phe Thr Val Thr Ala Pro Lys Glu Val Tyr Thr Val
            20                  25                  30

Asp Val Gly Ser Ser Val Ser Leu Glu Cys Asp Phe Asp Arg Arg Glu
            35                  40                  45

Cys Thr Glu Leu Glu Gly Ile Arg Ala Ser Leu Gln Lys Val Glu Asn
    50                  55                  60

Asp Thr Ser Leu Gln Ser Glu Arg Ala Thr Leu Leu Glu Glu Gln Leu
65                  70                  75                  80

Pro Leu Gly Lys Ala Leu Phe His Ile Pro Ser Val Gln Val Arg Asp
                85                  90                  95

Ser Gly Gln Tyr Arg Cys Leu Val Ile Cys Gly Ala Ala Trp Asp Tyr

```
                100             105             110
Lys Tyr Leu Thr Val Lys Val Lys Ala Ser Tyr Met Arg Ile Asp Thr
            115                 120                 125

Arg Ile Leu Glu Val Pro Gly Thr Gly Glu Val Gln Leu Thr Cys Gln
        130                 135                 140

Ala Arg Gly Tyr Pro Leu Ala Glu Val Ser Trp Gln Asn Val Ser Val
145                 150                 155                 160

Pro Ala Asn Thr Ser His Ile Arg Thr Pro Glu Gly Leu Tyr Gln Val
                165                 170                 175

Thr Ser Val Leu Arg Leu Lys Pro Gln Pro Ser Arg Asn Phe Ser Cys
            180                 185                 190

Met Phe Trp Asn Ala His Met Lys Glu Leu Thr Ser Ala Ile Ile Asp
        195                 200                 205

Pro Leu Ser Arg Met Glu Pro Lys Val Pro Arg Thr Trp Pro Leu His
        210                 215                 220

Val Phe Ile Pro Ala Cys Thr Ile Ala Leu Ile Phe Leu Ala Ile Val
225                 230                 235                 240

Ile Ile Gln Arg Lys Arg Ile
            245

<210> SEQ ID NO 3
<211> LENGTH: 822
<212> TYPE: DNA
<213> ORGANISM: Homo Sapiens

<400> SEQUENCE: 3
atgatcttcc tcctgctaat gttgagcctg gaattgcagc ttcaccagat agcagcttta    60
ttcacagtga cagtccctaa ggaactgtac ataatagagc atggcagcaa tgtgaccctg    120
gaatgcaact ttgacactgg aagtcatgtg aaccttggag caataacagc cagtttgcaa    180
aaggtggaaa atgatacatc cccacaccgt gaaagagcca cttttctgga ggagcagctg    240
cccctaggga aggcctcgtt ccacatacct caagtccaag tgagggacga aggacagtac    300
caatgcataa tcatctatgg ggtcgcctgg gactacaagt acctgactct gaaagtcaaa    360
gcttcctaca ggaaaataaa cactcacatc ctaaaggttc agaaacaga tgaggtagag    420 ctcacctgcc aggctacagg ttatcctctg gcagaagtat cctggccaaa cgtcagcgtt    480
cctgccaaca ccagccactc caggacccct gaaggcctct accaggtcac cagtgttctg    540
cgcctaaagc cacccctgg cagaaacttc agctgtgtgt ctggaatac tcacgtgagg    600 gaacttactt tggccagcat tgaccttcaa agtcagatgg aacccaggac ccatccaact    660
tggctgcttc acattttcat cccctcctgc atcattgctt tcattttcat agccacagtg    720
atagccctaa gaaaacaact ctgtcaaaag ctgtattctt caaaagacac aacaaaaaga    780
cctgtcacca acaaagag ggaagtgaac agtgctatct ga                         822

<210> SEQ ID NO 4
<211> LENGTH: 744
<212> TYPE: DNA
<213> ORGANISM: Mus musculus

<400> SEQUENCE: 4
atgctgctcc tgctgccgat actgaacctg agcttacaac ttcatcctgt agcagcttta    60
ttcaccgtga cagcccctaa agaagtgtac accgtagacg tcggcagcag tgtgagcctg    120
gagtgcgatt tgaccgcag agaatgcact gaactggaag ggataagagc cagttttgcag    180 aaggtagaaa atgatacgtc tctgcaaagt gaaagagcca ccctgctgga ggagcagctg    240
```

```
cccctgggaa aggctttgtt ccacatccct agtgtccaag tgagagattc cggcagtac     300 cgttgcctgg tcatctgcgg ggccgcctgg gactacaagt acctgacggt gaaagtcaaa     360
gcttcttaca tgaggataga cactaggatc ctggaggttc caggtacagg ggaggtgcag     420
cttacctgcc aggctagagg ttatccccta gcagaagtgt cctggcaaaa tgtcagtgtt     480
cctgccaaca ccagccacat caggaccccc gaaggcctct accaggtcac cagtgttctg     540
cgcctcaagc ctcagcctag cagaaacttc agctgcatgt tctggaatgc tcacatgaag     600
gagctgactt cagccatcat tgaccctctg agtcggatgg aacccaaagt ccccagaacg     660
tggccacttc atgttttcat cccggcctgc accatcgctt tgatcttcct ggccatagtg     720
ataatccaga gaaagaggat ctag                                            744
```

<210> SEQ ID NO 5
<211> LENGTH: 109
<212> TYPE: PRT
<213> ORGANISM: Homo sapiens

<400> SEQUENCE: 5

Leu Lys Ile Gln Ala Tyr Phe Asn Glu Thr Ala Asp Leu Pro Cys Gln
1               5                   10                  15

Phe Ala Asn Ser Gln Asn Gln Ser Leu Ser Glu Leu Val Val Phe Trp
            20                  25                  30

Gln Asp Gln Glu Asn Leu Val Leu Asn Glu Val Tyr Leu Gly Lys Glu
        35                  40                  45

Lys Phe Asp Ser Val His Ser Lys Tyr Met Gly Arg Thr Ser Phe Asp
    50                  55                  60

Ser Asp Ser Trp Thr Leu Arg Leu His Asn Leu Gln Ile Lys Asp Lys
65                  70                  75                  80

Gly Leu Tyr Gln Cys Ile Ile His His Lys Lys Pro Thr Cys Met Ile
                85                  90                  95

Arg Ile His Gln Met Asn Ser Glu Leu Ser Val Leu Ala
            100                 105

<210> SEQ ID NO 6
<211> LENGTH: 105
<212> TYPE: PRT
<213> ORGANISM: Homo sapiens

<400> SEQUENCE: 6

Ile His Val Thr Lys Glu Val Lys Glu Val Ala Thr Leu Ser Cys Gly
1               5                   10                  15

His Asn Val Ser Val Glu Glu Leu Ala Gln Thr Arg Ile Tyr Trp Gln
            20                  25                  30

Lys Glu Lys Lys Met Val Leu Thr Met Met Ser Gly Asp Met Asn Ile
        35                  40                  45

Trp Pro Glu Tyr Lys Asn Arg Thr Ile Phe Asp Ile Thr Asn Asn Leu
    50                  55                  60

Ser Ile Val Ile Leu Ala Leu Arg Pro Ser Asp Glu Gly Thr Tyr Glu
65                  70                  75                  80

Cys Val Val Leu Lys Tyr Glu Lys Asp Ala Phe Lys Arg Glu His Leu
                85                  90                  95

Ala Glu Val Thr Leu Ser Val Lys Ala
            100                 105

<210> SEQ ID NO 7
<211> LENGTH: 113

```
<212> TYPE: PRT
<213> ORGANISM: homo sapiens

<400> SEQUENCE: 7

Asp Leu Tyr Val Val Glu Tyr Gly Ser Asn Met Thr Ile Glu Cys Lys
1               5                   10                  15

Phe Pro Val Glu Lys Gln Leu Asp Leu Ala Ala Leu Ile Val Tyr Trp
            20                  25                  30

Glu Met Glu Asp Lys Asn Ile Ile Gln Phe Val His Gly Glu Glu Asp
        35                  40                  45

Leu Lys Val Gln His Ser Ser Tyr Arg Gln Arg Ala Arg Leu Leu Lys
    50                  55                  60

Asp Gln Leu Ser Leu Gly Asn Ala Ala Leu Gln Ile Thr Asp Val Lys
65                  70                  75                  80

Leu Gln Asp Ala Gly Val Tyr Arg Cys Met Ile Ser Tyr Gly Gly Ala
                85                  90                  95

Asp Tyr Lys Arg Ile Thr Val Lys Val Asn Ala Pro Tyr Asn Lys Ile
            100                 105                 110

Asn

<210> SEQ ID NO 8
<211> LENGTH: 113
<212> TYPE: PRT
<213> ORGANISM: Mus musculus

<400> SEQUENCE: 8

Asp Leu Tyr Val Val Glu Tyr Gly Ser Asn Val Thr Met Glu Cys Arg
1               5                   10                  15

Phe Pro Val Glu Arg Glu Leu Asp Leu Leu Ala Leu Val Val Tyr Trp
            20                  25                  30

Glu Lys Glu Asp Glu Gln Val Ile Gln Phe Val Ala Gly Glu Glu Asp
        35                  40                  45

Leu Lys Pro Gln His Ser Asn Phe Arg Gly Arg Ala Ser Leu Pro Lys
    50                  55                  60

Asp Gln Leu Leu Lys Gly Asn Ala Ala Leu Gln Ile Thr Asp Val Lys
65                  70                  75                  80

Leu Asp Asp Ala Gly Val Tyr Cys Cys Ile Ile Ser Tyr Gly Gly Ala
                85                  90                  95

Asp Tyr Lys Arg Ile Thr Leu Lys Val Asn Ala Pro Tyr Arg Lys Ile
            100                 105                 110

Asn

<210> SEQ ID NO 9
<211> LENGTH: 114
<212> TYPE: PRT
<213> ORGANISM: homo sapiens

<400> SEQUENCE: 9

Lys Glu Val Arg Ala Met Val Gly Ser Asp Val Glu Leu Ser Cys Ala
1               5                   10                  15

Cys Pro Glu Gly Ser Arg Phe Asp Leu Asn Asp Val Tyr Val Tyr Trp
            20                  25                  30

Gln Thr Ser Glu Ser Lys Thr Val Val Thr Tyr His Ile Pro Gln Asn
        35                  40                  45

Ser Ser Leu Glu Asn Val Asp Ser Arg Tyr Arg Asn Arg Ala Leu Met
    50                  55                  60

Ser Pro Ala Gly Leu Met Arg Gly Asp Phe Ser Leu Arg Leu Phe Asn
```

```
                65                   70                  75                  80
Val Thr Pro Gln Asp Glu Gln Lys Phe His Cys Leu Val Leu Ser Gln
                    85                  90                  95

Ser Leu Gly Phe Gln Glu Val Leu Ser Val Glu Val Thr Leu His Val
                    100                 105                 110

Ala Ala

<210> SEQ ID NO 10
<211> LENGTH: 110
<212> TYPE: PRT
<213> ORGANISM: homo sapiens

<400> SEQUENCE: 10

Asp Pro Val Val Ala Leu Val Gly Thr Asp Ala Thr Leu Cys Cys Ser
1               5                   10                  15

Pro Ser Pro Glu Pro Gly Phe Ser Leu Ala Gln Leu Asn Leu Ile Trp
                20                  25                  30

Gln Leu Thr Asp Thr Gln Leu Val His Ser Phe Ala Glu Gly Gln Asp
            35                  40                  45

Gln Gly Ser Ala Tyr Ala Asn Arg Thr Ala Leu Phe Pro Asp Leu Leu
        50                  55                  60

Ala Gln Gly Asn Ala Ser Leu Arg Leu Gln Arg Val Arg Val Ala Asp
65                  70                  75                  80

Glu Gly Ser Phe Thr Cys Phe Val Ser Ile Arg Asp Phe Gly Ser Ala
                85                  90                  95

Ala Val Ser Leu Gln Val Ala Ala Pro Tyr Ser Lys Pro Ser
                100                 105                 110

<210> SEQ ID NO 11
<211> LENGTH: 98
<212> TYPE: PRT
<213> ORGANISM: Homo sapiens

<400> SEQUENCE: 11

Glu Leu Tyr Ile Ile Glu His Gly Ser Asn Val Thr Leu Glu Cys Asn
1               5                   10                  15

Phe Asp Thr Gly Ser His Val Asn Leu Gly Ala Ile Thr Ala Ser Leu
                20                  25                  30

Gln Lys Val Glu Asn Asp Thr Ser Pro His Arg Glu Arg Ala Thr Leu
            35                  40                  45

Leu Glu Glu Gln Leu Pro Leu Gly Lys Ala Ser Phe His Ile Pro Gln
        50                  55                  60

Val Gln Val Arg Asp Gly Gln Tyr Gln Cys Ile Ile Ile Tyr Gly
65                  70                  75                  80

Val Ala Trp Asp Tyr Lys Tyr Leu Thr Leu Lys Val Lys Ala Ser Tyr
                85                  90                  95

Arg Lys

<210> SEQ ID NO 12
<211> LENGTH: 98
<212> TYPE: PRT
<213> ORGANISM: Mus Musculus

<400> SEQUENCE: 12

Glu Val Tyr Thr Val Asp Val Gly Ser Ser Val Ser Leu Glu Cys Asp
1               5                   10                  15

Phe Asp Arg Arg Glu Cys Thr Glu Leu Glu Gly Ile Arg Ala Ser Leu
                20                  25                  30
```

```
Gln Lys Val Glu Asn Asp Thr Ser Leu Gln Ser Glu Arg Ala Thr Leu
        35                  40                  45
Leu Glu Glu Gln Leu Pro Leu Gly Lys Ala Leu Phe His Ile Pro Ser
        50                  55                  60
Val Gln Val Arg Asp Ser Gly Gln Tyr Arg Cys Leu Val Ile Cys Gly
65                  70                  75                  80
Ala Ala Trp Asp Tyr Lys Tyr Leu Thr Val Lys Val Lys Ala Ser Tyr
                85                  90                  95
Met Arg
```

US 8,445,447 B2

B7-DC VARIANTS IMMUNOGENIC COMPOSITIONS AND METHODS OF USE THEREOF

CROSS-REFERENCE TO RELATED APPLICATIONS

This application is a continuation of U.S. Ser. No. 12/171,802 filed Jul. 11, 2008, which claims priority to U.S. Ser. No. 60/949,785 filed on Jul. 13, 2007. The contents of the above-referenced applications are incorporated by reference in their entirety.

STATEMENT REGARDING FEDERALLY SPONSORED RESEARCH OR DEVELOPMENT

This invention was made with Government Support under Grant No. R01 CA85721 awarded by the National Institutes of Health. The Government has certain rights in the invention.

REFERENCE TO SEQUENCE LISTING

The Sequence Listing submitted Mar. 7, 2012 as a text file named "JHU_D10161_ST25.txt," created on Jul. 11, 2008, and having a size of 14,831 bytes is hereby incorporated by reference.

FIELD OF THE INVENTION

This invention relates to compositions and methods for modulating T-cell activation, in particular to compositions and methods for enhancing T-cell activation.

BACKGROUND OF THE INVENTION

Antigen-specific activation and proliferation of lymphocytes are regulated by both positive and negative signals from costimulatory molecules. The most extensively characterized T cell costimulatory pathway is B7-CD28, in which B7-1 (CD80) and B7-2 (CD86) each can engage the stimulatory CD28 receptor and the inhibitory CTLA-4 (CD152) receptor. In conjunction with signaling through the T cell receptor, CD28 ligation increases antigen-specific proliferation of T cells, enhances production of cytokines, stimulates differentiation and effector function, and promotes survival of T cells (Lenshow, et al., *Annu. Rev. Immunol.*, 14:233-258 (1996); Chambers and Allison, *Curr. Opin. Immunol.*, 9:396-404 (1997); and Rathmell and Thompson, *Annu. Rev. Immunol.*, 17:781-828 (1999)). In contrast, signaling through CTLA-4 is thought to deliver a negative signal that inhibits T cell proliferation, IL-2 production, and cell cycle progression (Krummel and Allison, *J. Exp. Med*, 183:2533-2540 (1996); and Walunas, et al., *J. Exp. Med.*, 183:2541-2550 (1996)). Other members of the B7 family include B7-H1 (Dong, et al., *Nature Med.*, 5:1365-1369 (1999); and Freeman, et al., *J. Exp. Med.*, 192:1-9 (2000)), B7-DC (Tseng, et al., *J. Exp. Med.*, 193:839-846 (2001); and Latchman, et al., *Nature Immunol.*, 2:261-268 (2001)), B7-H2 (Wang, et al., *Blood*, 96:2808-2813 (2000); Swallow, et al., *Immunity*, 11:423-432 (1999); and Yoshinaga, et al., *Nature*, 402:827-832 (1999)), B7-H3 (Chapoval, et al., *Nature Immunol.*, 2:269-274 (2001)) and B7-H4 (Choi, et al., *J. Immunol.*, 171:4650-4654 (2003); Sica, et al., *Immunity*, 18:849-861 (2003); Prasad, et al., *Immunity*, 18:863-873 (2003); and Zang, et al., *Proc. Natl. Acad. Sci. U.S.A.*, 100:10388-10392 (2003)). B7-H1 and B7-DC are ligands for PD-1, B7-H2 is a ligand for ICOS, and B7-H3 remains at this time an orphan ligand (Dong, et al., *Immunol. Res.*, 28:39-48 (2003)).

B7 family molecules are expressed on the cell surface as homodimers with a membrane proximal constant IgC domain and a membrane distal IgV domain. Receptors for these ligands share a common extracellular IgV-like domain. Interactions of receptor-ligand pairs are mediated predominantly through residues in the IgV domains of the ligands and receptors (Schwartz, et al., *Nature Immunol.*, 3:427-434 (2002)). In general, IgV domains are described as having two sheets that each contain a layer of β-strands (Williams and Barclay, *Annu. Rev. Immunol.*, 6:381-405 (1988)). The front and back sheets of CTLA-4 contain strands A'GFC'C and ABEDC," respectively (Ostrov, et al., *Science*, 290:816-819 (2000)), whereas the front and back sheets of the B7 IgV domains are composed of strands AGFCC'C" and BED, respectively (Schwartz, et al., *Nature*, 410:604-608 (2001); Stamper, et al., *Nature*, 410:608-611 (2001); and Ikemizu, et al., *Immunity*, 12:51-60 (2000)). Crystallographic analysis revealed that the CTLA-4/B7 binding interface is dominated by the interaction of the CDR3-analogous loop from CTLA-4, composed of a MYPPPY motif, with a surface on B7 formed predominately by the G, F, C, C' and C" strands (Schwartz, et al., (2001) supra; and Stamper, et al., (2001) supra.). Data from ammo acid homologies, mutation, and computer modeling provide support for the concept that this motif also is a major B7-binding site for CD28 (Bajorath, et al., *J. Mol. Graph. Model.*, 15:135439 (1997)). Although the MYPPPY motif is not conserved in ICOS, studies have indicated that a related motif having the sequence FDPPPF and located at the analogous position is a major determinant for binding of ICOS to B7-H2 (Wand, et al., *J. Exp. Med.*, 195:1033-1041 (2002)).

B7-DC (also called PD-L2) is a relatively new member of the B7 family, and has an amino acid sequence that is about 34% identical to B7-H1 (also called PD-L1). Human and mouse B7-DC orthologues share about 70% amino acid identity. While B7-H1 and B7-DC transcripts are found in various tissues (Dong, et al. (1999) supra; Latchman, et al. (2001) supra; and Tamura, *Blood*, 97:1809-1816 (2001)), the expression profiles of the proteins are quite distinct. Expression of B7-H1 protein, although essentially not found in normal tissues other than macrophage-like cells, can be induced in a variety of tissues and cell types (Dong, et al. (1999) supra; Tamura, et al. (2001) supra; and Ishida, et al., *Immunol. Lett.*, 84:57-62 (2000)). In contrast, B7-DC is expressed only in dendritic cells and monocytes (Tseng, et al. (2001) supra; and Ishida, et al. (2000) supra).

It has been shown that both B7-H1 and B7-DC bind to PD-1 (programmed cell death-1) (Freeman, et al., *J. Exp. Med.*, 192:1027-1034 (2000); Tseng (2001) supra; Latchman (2001) supra), a distant member of the CD28 family with an immunoreceptor tyrosine-based inhibitory motif (ITIM) in its cytoplasmic domain (Ishida, et al., *EMBO J.*, 11:3887-3895 (1992)). PD-1 is expressed on a subset of thymocytes and up-regulated on T, B, and myeloid cells after activation (Agata, et al., *Int. Immunol.*, 8:765-772 (1996)). The phenotypes of PD-1$^{-/-}$ mice provide direct evidence for PD-1 being a negative regulator of immune responses in vivo. In the absence of PD-1, mice on the C57BL/6 background slowly develop a lupus-like glomerulonephritis and progressive arthritis (Nishimura, et al., *Immunity*, 11:141-151 (1999)), PD-1$^{-/-}$ mice on the BALB/c background rapidly develop a fatal autoimmune dilated cardiomyopathy (Nishimura, et al., *Science*, 291:319-322 (2001)). However, substantial evidence indicates that B7-DC can function to costimulate T cell responses. In the presence of suboptimal TCR signals, B7-DC stimulates increased proliferation and production of cytokines in vitro (Tseng, et al., *J. Exp. Med.* 193:839-846 (2001)). On the other hand, in vitro studies indicate a negative regulatory role for B7-DC in T cell responses (Latchman (2001) supra). These seemingly contradictory data are best interpreted by expression of additional receptors for B7-DC on T cells other than PD-1.

It would be advantageous to provide compositions that increase antigen-specific proliferation of T cells, enhance production of cytokines, stimulate differentiation and effector function, and promote survival of T cells. It would also be advantageous to provide B7-DC variant polypeptides that have reduced binding affinity for PD-1 compared to wild type B7-DC, yet retain the ability to costimulate T cells (i.e., increase antigen-specific proliferation of T cells, enhance cytokine production by T cells, stimulate differentiation and effector functions of T cells, or promote survival of T cells).

It is therefore an object of the present invention to provide B7-DC variant polypeptides that have reduced binding affinity for PD-1 compared to wild type B7-DC, yet retain the ability to costimulate T cells.

It is another object of the present invention to provide isolated nucleic acid molecules encoding variant B7-DC polypeptides.

It is another object of the present invention to provide cells containing vectors that express nucleic acid molecules encoding variant B7-DC polypeptides.

It is a still further object of the present invention to provide methods for costimulating T cells by contacting them with variant B7-DC polypeptides.

It is still a further object of the invention to provide methods for administering variant B7-DC polypeptides, nucleic acids encoding the same, or cells transfected or transduced with nucleic acids encoding variant B7-DC polypeptides to a mammal in need thereof.

It is still a further object of the invention to provide methods for potentiating an immune response to an antigen or a vaccine by administering variant B7-DC polypeptides in combination with the antigen or vaccine.

SUMMARY OF THE INVENTION

Compositions and methods for costimulating T cells (i.e., increasing antigen-specific proliferation of T cells, enhancing cytokine production by T cells, stimulating differentiation ad effector functions of T cells and/or promoting T cell survival) are provided. Suitable compositions include variant B7-DC polypeptides. Variant B7-DC polypeptides have reduced binding affinity for the inhibitory PD-1 ligand and substantially retain the ability to costimulate T cells. In certain embodiments, variant B7-DC polypeptides can contain, without limitation, substitutions, deletions or insertions at position 33 of the A' β-strand, positions 39 or 41 of the B β-strand, positions 56 or 58 of the C β-strand, positions 65 or 67 of the C' β-strand, positions 71 or 72 of the C" β-strand, position 84 of the D β-strand, position 88 of the E β-strand, positions 101, 103 or 105 of the F β-strand, or positions 111, 113 or 116 of the G β-strand of murine or human B7-DC.

Fragments of variant B7-DC polypeptides and fusion proteins containing variant B7-DC polypeptides are also provided. In some embodiments, fragments of variant B7-DC polypeptides include soluble fragments, including the extracellular domain or a fragment thereof. Other suitable fragments of variant B7-DC polypeptides include fragments containing the IgV and IgC domains or fragments containing only the IgV domain. Variant B7-DC polypeptides and fragments thereof can be coupled to other polypeptides to form fusion proteins. Provided are variant B7-DC fusion polypeptides having a first fusion partner comprising all or a part of a variant B7-DC protein fused (i) directly to a second polypeptide or, (ii) optionally, fused to a linker peptide sequence that is fused to the second polypeptide. The presence of the fusion partner can alter the solubility, affinity and/or valency of the variant B7-DC polypeptide. In certain embodiments, variants B7-DC polypeptides are fused to one or more domains of an Ig heavy chain constant region, preferably having an amino acid sequence corresponding to the hinge, $C_{H2}$ and $C_{H3}$ regions of a human immunoglobulin Cγ1 chain.

Nucleic acids encoding variant B7-DC polypeptides and variant B7-DC fusion proteins and host cells containing such nucleic acids in vectors are also provided.

Immunogenic compositions containing variant B7-DC polypeptides and variant B7-DC fusion proteins are also provided. Immunogenic compositions include antigens, a source of variant B7-DC polypeptides and optionally adjuvants and targeting molecules. Suitable antigens include viral, bacterial, parasite, environmental and tumor antigens.

Methods for using variant B7-DC polypeptides and variant B7-DC fusion proteins to costimulate T cells are provided. T cells can be costimulated with variant B7-DC compositions in vitro, ex vivo or in vivo. Costimulation of T cells using variant B7-DC compositions can occur before, during or after antigen-specific activation of the T cell.

Therapeutic uses of variant B7-DC polypeptides, variant B7-DC fusion proteins and nucleic acids encoding the same are provided. Variant B7-DC compositions can be used to stimulate the immune response to cancer and infectious diseases, including viral infections. Variant B7-DC compositions can also be used to stimulate the immune response of immunosuppressed subjects. In certain embodiments, variant B7-DC compositions are administered in conjunction with vaccines.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1 is a depiction of the full-length, immature amino acid sequence of human B7-DC (hB7-DC) (SEQ ID NO: 1). The signal sequence of human B7-DC contains the first 19 amino acids of the full-length immature amino acid sequence.

FIG. 2 is a depiction of the full-length, immature amino acid sequence of mouse B7-DC (mB7-DC) (SEQ ID NO: 2). The signal sequence of murine B7-DC contains the first 19 amino acids of the full-length immature amino acid sequence.

FIG. 3 is a depiction of a nucleotide sequence (SEQ ID NO: 3) encoding a full-length, immature human B7-DC polypeptide (SEQ ID NO: 1) having the amino acid sequence shown in FIG. 1. The signal sequence of human B7-DC is encoded by the first 57 nucleotides of the full-length immature nucleic acid sequence.

FIG. 4 is a depiction of a nucleotide sequence (SEQ ID NO: 4) encoding a full-length, immature mouse B7-DC polypeptide (SEQ ID NO: 2) having the amino acid sequence shown in FIG. 2. The signal sequence of murine B7-DC is encoded by the first 57 nucleotides of the full-length immature nucleic acid sequence.

Figure 5:
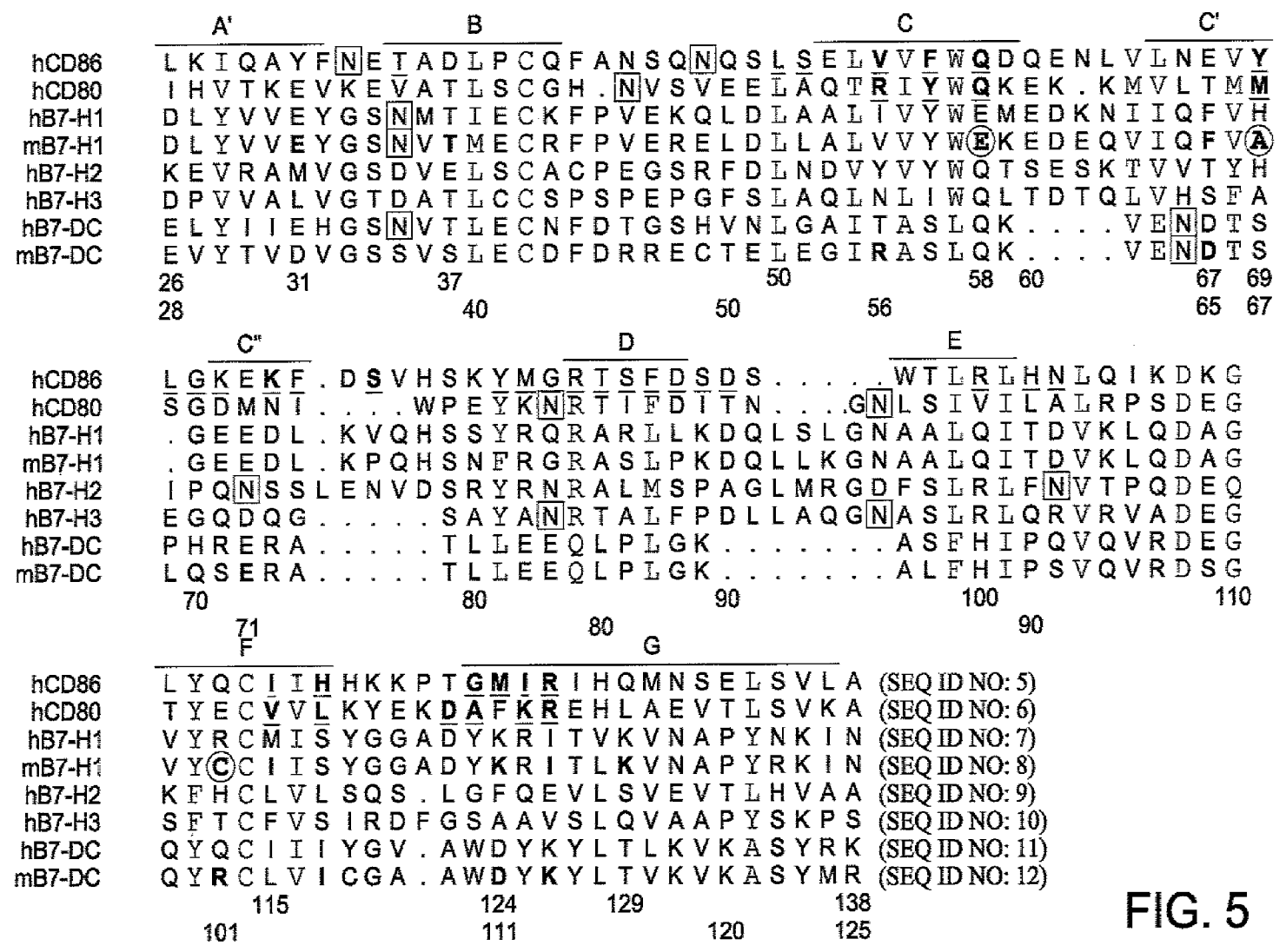

FIG. 5 is a structure-oriented sequence alignment of mouse and human B7 molecules. The alignment includes sequences from the N-terminal IgV domains of human CD86 (hCD86) (SEQ ID NO: 5), human CD80 (hCD80) (SEQ ID NO: 6), human B7-H1 (hB7-H1) (SEQ ID NO: 7), mouse B7-H1

(mB7-H1) (SEQ ID NO: 8), human B7-H2 (hB7-H2) (SEQ ID NO: 9), human B7-H3 (hB7-H3) (SEQ ID NO: 10), human B7-DC (hPD-L2) (SEQ ID NO: 11), and mouse B7-DC (mPD-L2) (SEQ ID NO: 12). β-strands observed in the x-ray structures of CDS0 and CD86 are labeled (A'-G), and residue positions most conserved across the B7 family (e.g., large hydrophobic, charged/polar, or cysteine residues) are shaded. Potential N-linked glycosylation sites are boxed. CD86 residues shown in italics are involved in formation of the crystallographic homodimer interface, which is conserved in CD80, and residues shown in bold italics participate in CTLA-4 binding in the structure of the complex. Residue positions in mB7-H1 and mB7-DC that are most important for PD-1 binding, based on mutagenesis studies, are underlined and shown in bold type. Residues in mB7-H1 that, when mutagenized, demonstrated increased avidity for PD-1 are circled. Residue numbers indicate positions within mB7-H1 (upper numbers) and mB7-DC (lower numbers).

FIG. 6 is a line graph showing results from surface plasmon resonance analysis of B7-DC binding to PD-1. The graph shows results for binding of wild type B7-DCIg and K113S B7-DCIg variant to immobilized PD-1Ig. Data are reported in terms of response units (RU) as a function of time in seconds.

FIG. 7 is a series of graphs showing the binding of wild type and variant B7-DCIg fusion proteins to CHO cells expressing PD-1. The B7-DCIg fusion proteins were incubated with the indicated wild type or variant B7-DC variant fusion protein and then with a FITC-labeled goat anti-human IgG and analyzed by FACS. Media alone and human IgG were used as negative controls and anti-human PD-1 antibody was used as a positive control. The graphs represent the number of cells as a function of level of emitted fluorescence. The numbers on the right and left sides of the graphs represent the percentage of cells that were considered to be positive and negative, respectively, for binding of the indicated composition.

FIGS. 8A and 8B are graphs showing effects of wild type and variant B7-DC molecules on T-cell costimulation. Data in FIG. 8A represent T cell proliferation after stimulation with the indicated wild type (-◇-) or variant (-■-D111; -x-K113) B7-DC Ig fusion proteins in the presence of anti-CD3 mAb coated onto the well-bottoms of 96-well plates at the indicated concentrations. T cell proliferation was measured as incorporation of $^3$H-Thymidine ($^3$H-TdR) (x$10^3$ cpm) as a function of the concentration of anti-CD3 mAb (μg/ml). Human Ig (hIg) (-o-) and PBS alone (-▲-) were used as negative controls for the costimulatory molecules. Data depict one representative experiment of three. Data in FIG. 8B represent IFN-γ secretion (ng/ml) by T cells cultured in the presence of the indicated Ig fusion proteins (■ wild type; □D111; □K113) and anti-CD3 for 48 or 72 hours. Human Ig (□) and PBS (□) were used as negative controls. Data depict one representative experiment of three.

FIG. 9 is a line graph showing proliferation of PD-1$^{-/-}$ T cells after incubation with the indicated wild type (-●-) or variant (-Δ-D111; -x-K113) B7-DC Ig fusion proteins in the presence of anti-CD3 mAb. T cell proliferation was measured as incorporation of $^3$H-Thymidine ($^3$H-TdR) (x$10^3$ cpm) as a function of the concentration of anti-CD3 mAb (μg/ml). Human Ig (-■-) and PBS (-o-) were used as negative controls. Data depict one representative experiment of three.

Figure 14:
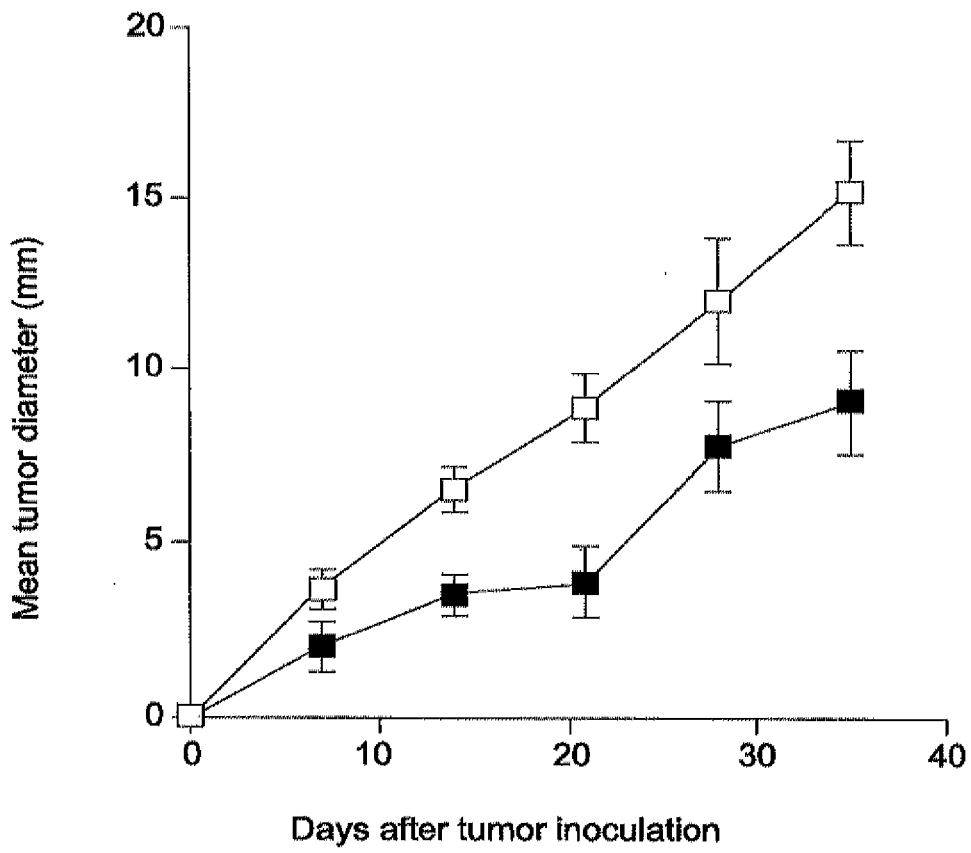

FIG. 14 is a line graph showing the effect of intraperitoneal injection of wild-type B7-DCIg on growth (mean tumor diameter in millimeters) of P815 mastrocytoma murine tumor cells in syngeneic immunocompetent (DBA/2) mice as a function of time (days). Mice were injected intraperitoneally with 0.1 mg of control Ig (-□-) or wild-type B7-DCIg (-■-) on day 3 and day 8.

DETAILED DESCRIPTION OF THE INVENTION

I. Definitions

As used herein the term "isolated" is meant to describe a compound of interest (e.g., either a polynucleotide or a polypeptide) that is in an environment different from that in which the compound naturally occurs e.g. separated from its natural milieu such as by concentrating a peptide to a concentration at which it is not found in nature. "Isolated" is meant to include compounds that are within samples that are substantially enriched for the compound of interest and/or in which the compound of interest is partially or substantially purified.

As used herein, the term "polypeptide" refers to a chain of amino acids of any length, regardless of modification (e.g., phosphorylation or glycosylation).

As used herein, a "costimulatory polypeptide" is a polypeptide that, upon interaction with a cell-surface molecule on T cells, enhances T cell responses, enhances proliferation of T cells, enhances production and/or secretion of cytokines by T cells, stimulates differentiation and effector functions of T cells or promotes survival of T cells relative to T cells not contacted with a costimulatory peptide.

As used herein, a "variant" polypeptide contains at least one amino acid sequence alteration as compared to the amino acid sequence of the corresponding wild-type polypeptide.

As used herein, an "amino acid sequence alteration" can be, for example, a substitution, a deletion, or an insertion of one or more amino acids.

As used herein, a "vector" is a replicon, such as a plasmid, phage, or cosmid, into which another DNA segment may be inserted so as to bring about the replication of the inserted segment. The vectors described herein can be expression vectors.

As used herein, an "expression vector" is a vector that includes one or more expression control sequences As used herein, an "expression control sequence" is a DNA sequence that controls and regulates the transcription and/or translation of another DNA sequence.

As used herein, "operably linked" means incorporated into a gentic construct so that expression control sequences effectively control expression of a coding sequence of interest.

As used herein, a "fragment" of a polypeptide refers to any subset of the polypeptide that is a shorter polypeptide of the full length protein. Generally, fragments will be five or more amino acids in length.

As used herein, "valency" refers to the number of binding sites available per molecule.

As used herein, "conservative" amino acid substitutions are substitutions wherein the substituted amino acid has similar structural or chemical properties.

As used herein, "non-conservative" amino acid substitutions are those in which the charge, hydrophobicity, or bulk of the substituted amino acid is significantly altered.

As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-B7-DC proteins).

As used herein with respect to nucleic acids, the term "isolated" includes any non-naturally-occurring nucleic acid sequence, since such non-naturally-occurring sequences are not found in nature and do not have immediately contiguous sequences in a naturally-occurring genome.

As used herein, the term "host cell" refers to prokaryotic and eukaryotic cells into which a recombinant expression vector can be introduced.

As used herein, "transformed" and "transfected" encompass the introduction of a nucleic acid (e.g. a vector) into a cell by a number of techniques known in the art.

As used herein, the term "antibody" is meant to include both intact molecules as well as fragments thereof that include the antigen-binding site. These include Fab and F(ab')$_2$ fragments which lack the Fc fragment of an intact antibody.

The terms "individual", "host", "subject", and "patient" are used interchangeably herein, and refer to a mammal, including, but not limited to, murines, simians, humans, mammalian farm animals, mammalian sport animals, and mammalian pets.

As used herein the term "effective amount" or "therapeutically effective amount" means a dosage sufficient to treat, inhibit, or alleviate one or more symptoms of an inflammatory response or autoimmune disease state being treated or to otherwise provide a desired pharmacologic and/or physiologic effect. The precise dosage will vary according to a variety of factors such as subject-dependent variables (e.g., age, immune system health, etc.), the disease, and the treatment being effected.

II. Compositions

A. Isolated B7-DC Polypeptides
1. Variant B7-DC Polypeptides

Isolated B7-DC polypeptides are disclosed herein. The B7-DC polypeptide may be of any species of origin. In one embodiment, the B7-DC polypeptide is from a mammalian species. In a preferred embodiment, the B7-DC polypeptide is of murine or human origin. The full-length, immature amino acid sequence of mouse B7-DC (SEQ ID NO: 2) is depicted in FIG. 2. The signal sequence of murine B7-DC contains the first 19 amino acids of the full-length immature amino acid sequence. The full-length, immature amino acid sequence of human B7-DC (SEQ ID NO: 1) is depicted in FIG. 1. The signal sequence of human B7-DC contains the first 19 amino acids of the full-length immature amino acid sequence. As used herein, the term "polypeptide" refers to a chain of amino acids of any length, regardless of modification (e.g., phosphorylation or glycosylation).

In one embodiment the variant B7-DC polypeptide has the same activity, substantially the same activity, or different activity as wildtype B7-DC. Substantially the same activity means it retains the ability to co-stimulate T cells.

The polypeptides disclosed herein include variant B7-DC polypeptides. As used herein, a "variant" polypeptide contains at least one amino acid sequence alteration as compared to the amino acid sequence of the corresponding wild-type polypeptide. An amino acid sequence alteration can be, for example, a substitution, a deletion, or an insertion of one or more amino acids.

A variant B7-DC polypeptide can have any combination of amino acid substitutions, deletions or insertions. In one embodiment, isolated B7-DC variant polypeptides have an integer number of amino acid alterations such that their amino acid sequence shares at least 60, 70, 80, 85, 90, 95, 97, 98, 99, 99.5 or 100% identity with an amino acid sequence of a wild type B7-DC polypeptide. In a preferred embodiment, B7-DC variant polypeptides have an amino acid sequence sharing at least 60, 70, 80, 85, 90, 95, 97, 98, 99, 99.5 or 100% identity with the amino acid sequence of a wild type murine or wild type human B7-DC polypeptide.

Percent sequence identity can be calculated using computer programs or direct sequence comparison. Preferred computer program methods to determine identity between two sequences include, but are not limited to, the GCG program package, FASTA, BLASTP, and TBLASTN (see, e.g., D. W. Mount, 2001, Bioinformatics: Sequence and Genome Analysis, Cold Spring Harbor Laboratory Press, Cold Spring Harbor, N.Y.). The BLASTP and TBLASTN programs are publicly available from NCBI and other sources. The well-known Smith Waterman algorithm may also be used to determine identity.

Exemplary parameters for amino acid sequence comparison include the following: 1) algorithm from Needleman and Wunsch (*J. Mol. Biol.*, 48:443-453 (1970)); 2) BLOSSUM62 comparison matrix from Hentikoff and Hentikoff (*Proc. Natl. Acad. Sci. U.S.A.*, 89:10915-10919 (1992)) 3) gap penalty=12; and 4) gap length penalty=4. A program useful with these parameters is publicly available as the "gap" program (Genetics Computer Group, Madison, Wis.). The aforementioned parameters are the default parameters for polypeptide comparisons (with no penalty for end gaps).

Alternatively, polypeptide sequence identity can be calculated using the following equation: % identity=(the number of identical residues)/(alignment length in amino acid residues)*100. For this calculation, alignment length includes internal gaps but does not include terminal gaps.

Amino acid substitutions in B7-DC polypeptides may be "conservative" or "non-conservative". As used herein, "conservative" amino acid substitutions are substitutions wherein the substituted amino acid has similar structural or chemical properties, and "non-conservative" amino acid substitutions are those in which the charge, hydrophobicity, or bulk of the substituted amino acid is significantly altered. Non-conservative substitutions will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain.

Examples of conservative amino acid substitutions include those in which the substitution is within one of the five following groups: 1) small aliphatic, nonpolar or slightly polar residues (Ala, Ser, Thr, Pro, Gly); 2) polar, negatively charged residues and their amides (Asp, Asn, Glu, Gln); polar, positively charged residues (His, Arg, Lys); large aliphatic, non-polar residues (Met, Leu, Ile, Val, Cys); and large aromatic resides (Phe, Tyr, Trp). Examples of non-conservative amino acid substitutions are those where 1) a hydrophilic residue, e.g., seryl or threonyl, is substituted for (or by) a hydrophobic residue, e.g., leucyl, isoleucyl, phenylalanyl, valyl, or alanyl; 2) a cysteine or proline is substituted for (or by) any other residue; 3) a residue having an electropositive side chain, e.g., lysyl, arginyl, or histidyl, is substituted for (or by) an electronegative residue, e.g., glutamyl or aspartyl; or 4) a residue having a bulky side chain, e.g., phenylalanine, is substituted for (or by) a residue that does not have a side chain, e.g., glycine.

B7 family molecules, including B7-DC are expressed at the cell surface as homodimers with a membrane proximal constant IgC domain and a membrane distal IgV domain. Receptors for these ligands share a common extracellular IgV-like domain. Interactions of receptor-ligand pairs are mediated predominantly through residues in the IgV domains of the ligands and receptors. In general, IgV domains are described as having two sheets that each contain a layer of β-strands. These β-strands are referred to as A', B, C, C', C", D, E, F and G. In one embodiment the B7-DC variant polypeptides contain amino acid alterations (i.e., substitutions, deletions or insertions) within one or more of these β-strands in any possible combination. In another embodiment, B7-DC variants contain one or more amino acid alterations (i.e., substitutions, deletions or insertions) within the A', C, C', C", D, E, F or G β-strands. In a preferred embodiment B7-DC variants contain one or more amino acid alterations in the G β-strand. With respect to murine B7-DC or human B7-DC, a variant B7-DC polypeptide can contain, without limitation, substitutions, deletions or insertions at position 33 of the A' β-strand, positions 39 or 41 of the B β-strand, positions 56 or 58 of the C β-strand, positions 65 or 67 of the C' β-strand, positions 71 or 72 of the C" β-strand, position 84 of the D β-strand, position 88 of the E β-strand, positions 101, 103 or 105 of the F β-strand, or positions 111, 113 or 116 of the G β-strand.

In one embodiment, variant B7-DC polypeptides contain a substitution at position 33 (e.g., a serine substitution for aspartic acid at position 33), a substitution at position 39 (e.g., a tyrosine substitution for serine at position 39), a substitution at position 41 (e.g., a serine substitution for glutamic acid at position 41), a substitution at position 56 (e.g., a serine substitution for arginine at position 56), a substitution at position 58 (e.g., a tyrosine substitution for serine at position 58), a substitution at position 65 (e.g., a serine substitution for aspartic acid at position 65), a substitution at position 67 (e.g., a tyrosine substitution for serine at position 67), a substitution at position 71 (e.g., a serine substitution for glutamic acid at position 71), a substitution at position 72 (e.g., a serine substitution for arginine at position 72), a substitution at position 84 (e.g., a serine substitution for lysine at position 84), a substitution at position 88 (e.g., an alanine substitution for histidine at position 88), a substitution at position 101 (e.g., a serine substitution for arginine at position 101), a substitution at position 103 (e.g., an alanine substitution for leucine at position 103), a substitution at position 105 (e.g., an alanine substitution for isoleucine at position 105), a substitution at position 111 (e.g., a serine substitution for aspartic acid at position 111), a substitution at position 113 (e.g., a serine substitution for lysine at position 113), or a substitution at position 116 (e.g., a tyrosine substitution for threonine at position 116).

It is understood, however, that substitutions at the recited amino acid positions can be made using any amino acid or amino acid analog. For example, the substitutions at the recited positions can be made with any of the naturally-occurring amino acids (e.g., alanine, aspartic acid, asparagine, arginine, cysteine, glycine, glutamic acid, glutamine, histidine, leucine, valine, isoleucine, lysine, methionine, proline, threonine, serine, phenylalanine, tryptophan, or tyrosine).

While the substitutions described herein are with respect to mouse and human B7-DC, it is noted that one of ordinary skill in the art could readily make equivalent alterations in the corresponding polypeptides from other species (e.g., rat, hamster, guinea pig, gerbil, rabbit, dog, cat, horse, pig, sheep, cow or non-human primate).

2. Properties of Variant B7-DC Polypeptides

The disclosed isolated B7-DC polypeptides are capable of costimulating T cells. A "costimulatory polypeptide" is a polypeptide that, upon interaction with a cell-surface molecule on a T cell, enhances T cell responses, enhances proliferation of T cells, enhances production and/or secretion of cytokines by T cells, stimulates differentiation and effector functions of T cells or promotes survival of T cells relative to T cells not contacted with a costimulatory peptide. The T cell response that results from the interaction typically is greater than the response in the absence of the costimulatory polypeptide. The response of the T cell in the absence of the costimulatory polypeptide can be no response or can be a response significantly lower than in the presence of the costimulatory polypeptide. The response of the T cell can be an effector (e.g., CTL or antibody-producing B cell) response, a helper response providing help for one or more effector (e.g., CTL or antibody-producing B cell) responses, or a suppressive response.

Variant B7-DC polypeptides disclosed herein have reduced binding affinity for PD-1 as compared to the binding affinity of the corresponding wild-type B7-DC polypeptide. The binding affinity of a variant typically is reduced by at least 50 percent, 55 percent, 60 percent, 70 percent, 75 percent, 80 percent, 90 percent, 95 percent, 99 percent, or more than 99 percent as compared to the binding affinity of the corresponding wild-type polypeptide.

Methods for measuring the binding affinity between two molecules are well known in the art. Methods for measuring the binding affinity of B7-DC variant polypeptides for PD-1 include, but are not limited to, fluorescence activated cell sorting (FACS), surface plasmon resonance, fluorescence anisotropy, affinity chromatography and affinity selection-mass spectrometry.

In addition, disclosed variant B7-DC polypeptides with reduced binding affinity for PD-1 retain substantial costimulatory activity. For example, a variant B7-DC polypeptide can have at least 20 percent, 25 percent, 30 percent, 40 percent, 50 percent, 60 percent, 75 percent, 90 percent, 100 percent, or more than 100 percent of the level of costimulatory activity exhibited by the corresponding wild-type B7-DC polypeptide.

Methods for measuring costimulation of T cells are well known in the art and include measurements of T cell proliferation and secretion of cytokines, including, but not limited to, Il-2, IL-4, IL-5, IL-6, IL-10, IL-13, and IFN-γ. Proliferation of T cells can be measured by a number of methods including, but not limited to, cell counting, measuring DNA synthesis by uptake of labeled nucleotides (such as [$^3$H] TdR and BrdU) and measuring metabolic activity with tetrazolium salts. Methods for measuring the secretion of cytokines include, but are not limited to, ELISA.

3. Fragments of Variant B7-DC Polypeptides

The B7-DC polypeptides disclosed herein can be full-length polypeptides, or can be a fragment of a full length B7-DC polypeptide. As used herein, a fragment of B7-DC refers to any subset of the polypeptide that is a shorter polypeptide of the full length protein.

In one embodiment, variant B7-DC polypeptide fragments are those that retain the ability to costimulate T cells. A variant B7-DC polypeptide that is a fragment of full-length B7-DC typically has at least 20 percent, 30 percent, 40 percent, 50 percent, 60 percent, 70 percent, 80 percent, 90 percent, 95 percent, 98 percent, 99 percent, 100 percent, or even more than 100 percent of the costimulatory activity of the full-length variant B7-DC polypeptide.

Human and mouse B7-DC proteins contain a short intracytoplasmic domain, a single transmembrane domain and an extracellular domain. The extracellular domain contains two Ig domains; a membrane proximal IgC domain and a membrane distal IgV domain. Useful fragments of variant B7-DC polypeptides include soluble fragments. Soluble B7-DC fragments are fragments of B7-DC that may be shed, secreted or otherwise extracted from the producing cells. In one embodiment, variant B7-DC polypeptide fragments include the entire extracellular domain of B7-DC. The extracellular domain of B7-DC includes amino acids from about 26 to about amino acid 226 of murine or human B7-DC or costimulatory fragments thereof. In another embodiment, variant B7-DC polypeptide fragments include the IgC and IgV domains of B7-DC. In another embodiment, variant B7-DC polypeptide fragments include the IgV domain of B7-DC.

In one embodiment, variant B7-DC polypeptide fragments may contain a region of the polypeptide that is important for binding affinity for PD-1. These polypeptide fragments may be useful to compete for binding to PD-1 and to prevent native B7-DC from binding to PD-1. By competing for binding to PD-1, these fragments may be useful to enhance an immune response, as inhibiting interactions of B7-H1 and B7-DC with PD-1 may also inhibit the suppression of immune responses that would otherwise occur. A polypeptide fragment of mouse or human B7-DC that could competitively bind to PD-1 can contain, for example, amino acids 67-71, 101-105, or 111-113. The binding of B7-DC to PD-1 typically is inhibited by at least 50 percent, 60 percent, 70 percent, 75 percent, 80 percent, 90 percent, 95 percent, or more than 95 percent as compared to the level of binding of B7-DC to PD-1 in the absence of the fragment.

4. Modified Variant B7-DC Polypeptides

Variant B7-DC polypeptides may be modified by chemical moieties that may be present in polypeptides in a normal cellular environment, for example, phosphorylation, methylation, amidation, sulfation, acylation, glycosylation, sumoylation and ubiquitylation. Variant B7-DC polypeptides may also be modified with a label capable of providing a detectable signal, either directly or indirectly, including, but not limited to, radioisotopes and fluorescent compounds.

Variant B7-DC polypeptides may also be modified by chemical moieties that are not normally added to polypeptides in a cellular environment. Such modifications may be introduced into the molecule by reacting targeted amino acid residues of the polypeptide with an organic derivatizing agent that is capable of reacting with selected side chains or terminal residues. Another modification is cyclization of the protein.

Examples of chemical derivatives of the polypeptides include lysinyl and amino terminal residues derivatized with succinic or other carboxylic acid anhydrides. Derivatization with a cyclic carboxylic anhydride has the effect of reversing the charge of the lysinyl residues. Other suitable reagents for derivatizing amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Carboxyl side groups, aspartyl or glutamyl, may be selectively modified by reaction with carbodiimides (R—N=C=N—R') such as 1-cyclohexyl-3-(2-morpholinyl-(4-ethyl)carbodiimide or 1-ethyl-3-(4-azonia-4,4-dimethylpentyl) carbodiimide. Furthermore, aspartyl and glutamyl residues can be converted to asparaginyl and glutaminyl residues by reaction with ammonia. Polypeptides may also include one or more D-amino acids that are substituted for one or more L-amino acids.

5. Variant B7-DC Fusion Polypeptides

The variant B7-DC polypeptides disclosed herein may be coupled to other polypeptides to form fusion proteins. Provided are variant B7-DC fusion polypeptides having a first fusion partner comprising all or a part of a variant B7-DC protein fused (i) directly to a second polypeptide or, (ii) optionally, fused to a linker peptide sequence that is fused to the second polypeptide. The presence of the fusion partner can alter the solubility, affinity and/or valency of the variant B7-DC polypeptide. As used herein, "valency" refers to the number of binding sites available per molecule. Variant B7-DC fusion proteins described herein include any combination of amino acid alteration (i.e. substitution, deletion or insertion), fragment of B7-DC, and/or modification as described above. In one embodiment, variant B7-DC fusion proteins include the extracellular domain of a B7-DC protein, or a costimulatory fragment thereof, as the first binding partner. In another embodiment, variant 137-DC fusion proteins include the IgV and IgC domain of a B7-DC protein as the first binding partner. In another embodiment, variant B7-DC fusion proteins include the IgV domain of a B7-DC protein as the first binding partner.

The second polypeptide binding partner may be N-terminal or C-terminal relative to the variant B7-DC polypeptide. In a preferred embodiment, the second polypeptide is C-terminal to the variant B7-DC polypeptide.

A large number of polypeptide sequences that are routinely used as fusion protein binding partners are well known in the art. Examples of useful polypeptide binding partners include, but are not limited to, green fluorescent protein (GFP), glutathione S-transferase (GST), polyhistidine, myc, hemagglutinin, Flag™ tag (Kodak, New Haven, Conn.), maltose E binding protein and protein A. In one embodiment, the variant B7-DC fusion protein is fused to one or more domains of an Ig heavy chain constant region, preferably having an amino acid sequence corresponding to the hinge, $C_{H2}$ and $C_{H3}$ regions of a human immunoglobulin Cγ1 chain.

B. Isolated Nucleic Acid Molecules

Isolated nucleic acid sequences encoding variant B7-DC polypeptides are disclosed herein. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-B7-DC proteins). The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule independent of other sequences (e.g., a chemically synthesized nucleic acid, or a cDNA or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

Nucleic acids can be in sense or antisense orientation, or can be complementary to a reference sequence encoding a B7-DC polypeptide. Reference sequences include, for example, the nucleotide sequence of human B7-DC (SEQ ID NO: 3) set forth in FIG. 3, which encodes full-length, immature B7-DC having the amino acid sequence (SEQ ID NO: 1) set forth in FIG. 1 and the nucleotide sequence of murine B7-DC (SEQ ID NO: 4) set forth in FIG. 4, which encodes full-length, immature B7-DC having the amino acid sequence (SEQ ID NO: 2) set forth in FIG. 2.

Nucleic acids can be DNA, RNA, or nucleic acid analogs. Nucleic acid analogs can be modified at the base moiety, sugar moiety, or phosphate backbone. Such modification can improve, for example, stability, hybridization, or solubility of the nucleic acid. Modifications at the base moiety can include deoxyuridine for deoxythymidine, and 5-methyl-2'-deoxycytidine or 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summer-ton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone.

C. Vectors and Host Cells

Nucleic acids, such as those described above, can be inserted into vectors for expression in cells. As used herein, a "vector" is a replicon, such as a plasmid, phage, or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalo virus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen Life Technologies (Carlsbad, Calif.).

An expression vector can include a tag sequence. Tag sequences, are typically expressed as a fusion with the encoded polypeptide. Such tags can be inserted anywhere within the polypeptide including at either the carboxyl or amino terminus. Examples of useful tags include, but are not limited to, green fluorescent protein (GFP), glutathione S-transferase (GST), polyhistidine, c-myc, hemagglutinin, Flag™ tag (Kodak, New Haven, Conn.), maltose E binding protein and protein A. In one embodiment, the variant B7-DC fusion protein is present in a vector containing nucleic acids that encode one or more domains of an Ig heavy chain constant region, preferably having an amino acid sequence corresponding to the hinge, $C_{H2}$ and $C_{H3}$ regions of a human immunoglobulin Cγ1 chain.

Vectors containing nucleic acids to be expressed can be transferred into host cells. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Host cells (e.g., a prokaryotic cell or a eukaryotic cell such as a CHO cell) can be used to, for example, produce the variant B7-DC polypeptides described herein. In some embodiments, a host cell (e.g., an antigen presenting cell) can be used to express the variant B7-DC polypeptides disclosed herein for presentation to a T cell.

D. Antibodies

Monoclonal antibodies (mAbs) and methods for their production and use are described in Kohler and Milstein, Nature 256:495-497 (1975); U.S. Pat. No. 4,376,110; Hartlow, E. et al., Antibodies: A Laboratory Manual, Cold Spring Harbor Laboratory Press, Cold Spring Harbor, N.Y., 1988); Monoclonal Antibodies and Hybridomas: A New Dimension in Biological Analyses, Plenum Press, New York, N.Y. (1980);

H. Zola et al., in Monoclonal Hybridoma Antibodies: Techniques and Applications, CRC Press, 1982)).

Immunoassay methods are described in Coligan, J. E. et al., eds., Current Protocols in Immunology, Wiley-Interscience, New York 1991 (or current edition); Butt, W. R. (ed.) Practical Immunoassay: The State of the Art, Dekker, N.Y., 1984; Bizollon, Ch. A., ed., Monoclonal Antibodies and New Trends in Immunoassays, Elsevier, N.Y., 1984; Butler, J. E., ELISA (Chapter 29), In: van Oss, C. J. et al., (eds), IMMUNOCHEMISTRY, Marcel Dekker, Inc., New York, 1994, pp. 759-803; Butler, J. E. (ed.), Immunochemistry of Solid-Phase Immunoassay, CRC Press, Boca Raton, 1991; Weintraub, B., Principles of Radioimmunoassays, Seventh Training Course on Radioligand Assay Techniques, The Endocrine Society, March, 1986; Work, T. S. et al., Laboratory Techniques and Biochemistry in Molecular Biology, North Holland Publishing Company, NY, (1978) (Chapter by Chard, T., "An Introduction to Radioimmune Assay and Related Techniques").

Anti-idiotypic antibodies are described, for example, in Idiotypy in Biology and Medicine, Academic Press, New York, 1984; Immunological Reviews Volume 79, 1984; Immunological Reviews Volume 90, 1986; Curr. Top. Microbiol., Immunol. Volume 119, 1985; Bona, C. et al., CRC Crit. Rev. Immunol., pp. 33-81 (1981); Jerne, N K, Ann. Immunol. 125C:373-389 (1974); Jerne, N K, In: Idiotypes—Antigens on the Inside, Westen-Schnurr, I., ed., Editiones Roche, Basel, 1982, Urbain, J. et al., Ann. Immunol. 133D:179-(1982); Rajewsky, K. et al., Ann. Rev. Immunol. 1:569-607 (1983).

Monoclonal and polyclonal antibodies that are reactive with novel epitopes of B7-DC that are absent from known B7 family proteins are described herein. The antibodies may be xenogeneic, allogeneic, syngeneic, or modified forms thereof, such as humanized or chimeric antibodies. Antiidiotypic antibodies specific for the idiotype of an anti-B7-DC antibody are also included. The term "antibody" is meant to include both intact molecules as well as fragments thereof that include the antigen-binding site and are capable of binding to a B7-DC epitope. These include, Fab and F(ab')$_2$ fragments which lack the Fc fragment of an intact antibody, clear more rapidly from the circulation, and may have less nonspecific tissue binding than an intact antibody (Wahl et al., J. Nuc. Med. 24:316-325 (1983)). Also included are Fv fragments (Hochman, J. et al. (1973) Biochemistry 12:1130-1135; Sharon, J. et al. (1976) Biochemistry 15:1591-1594). These various fragments are produced using conventional techniques such as protease cleavage or chemical cleavage (see, e.g., Rousseaux et al., Meth. Enzymol., 121:663-69 (1986)).

Polyclonal antibodies are obtained as sera from immunized animals such as rabbits, goats, rodents, etc. and may be used directly without further treatment or may be subjected to conventional enrichment or purification methods such as ammonium sulfate precipitation, ion exchange chromatography, and affinity chromatography.

The immunogen may comprise the complete B7-DC protein, or fragments or derivatives thereof. Preferred immunogens comprise all or a part of the extracellular domain (ECD) of human B7-DC, where these residues contain the post-translation modifications, such as glycosylation, found on the native B7-DC. Immunogens comprising the extracellular domain are produced in a variety of ways known in the art, e.g., expression of cloned genes using conventional recombinant methods, isolation from cells of origin, cell populations expressing high levels of B7-DC, etc.

Monoclonal antibodies may be produced using conventional hybridoma technology, such as the procedures introduced by Kohler and Milstein (Nature, 256:495-97 (1975)), and modifications thereof (see above references). An animal, preferably a mouse is primed by immunization with an immunogen as above to elicit the desired antibody response in the primed animal. B lymphocytes from the lymph nodes, spleens or peripheral blood of a primed, animal are fused with myeloma cells, generally in the presence of a fusion promoting agent such as polyethylene glycol (PEG). Any of a number of murine myeloma cell lines are available for such use: the P3-NS1/1-Ag4-1, P3-x63-k0Ag8.653, Sp2/0-Ag14, or HL1-653 myeloma lines (available from the ATCC, Rockville, Md.). Subsequent steps include growth in selective medium so that unfused parental myeloma cells and donor lymphocyte cells eventually die while only the hybridoma cells survive. These are cloned and grown and their supernatants screened for the presence of antibody of the desired specificity, e.g. by immunoassay techniques using B7-DC fusion proteins. Positive clones are subcloned, e.g., by limiting dilution, and the monoclonal antibodies are isolated.

Hybridomas produced according to these methods can be propagated in vitro or in vivo (in ascites fluid) using techniques known in the art (see generally Fink et al., Prog. Clin. Pathol., 9:121-33 (1984)). Generally, the individual cell line is propagated in culture and the culture medium containing high concentrations of a single monoclonal antibody can be harvested by decantation, filtration, or centrifugation.

The antibody may be produced as a single chain antibody or scFv instead of the normal multimeric structure. Single chain antibodies include the hypervariable regions from an Ig of interest and recreate the antigen binding site of the native Ig while being a fraction of the size of the intact Ig (Skerra, A. et al. (1988) Science, 240: 1038-1041; Pluckthun, A. et al. (1989) Methods Enzymol. 178: 497-515; Winter, G. et al. (1991) Nature, 349: 293-299). In a preferred embodiment, the antibody is produced using conventional molecular biology techniques.

E. Immunogenic Compositions

Vaccines require strong T cell response to eliminate cancer cells and infected cells. Variant B7-DC variants described herein can be administered as a component of a vaccine to provide a costimulatory signal to T cells. Vaccines disclosed herein include antigens, a source of variant B7-DC polypeptides and optionally adjuvants and targeting molecules. Sources of variant B7-DC polypeptides include any variant B7-DC polypeptide, variant B7-DC fusion proteins, nucleic acids encoding variant B7-DC polypeptides or variant B7-DC fusion proteins, or host cells containing vectors that express B7-DC polypeptides or variant B7-DC fusion proteins.

1. Antigens

Antigens can be peptides, proteins, polysaccharides, saccharides, lipids, nucleic acids, or combinations thereof. The antigen can be derived from a virus, bacterium, parasite, plant, protozoan, fungus, tissue or transformed cell such as a cancer or leukemic cell and can be a whole cell or immunogenic component thereof, e.g., cell wall components or molecular components thereof.

Suitable antigens are known in the art and are available from commercial government and scientific sources. In one embodiment, the antigens are whole inactivated or attenuated organisms. These organisms may be infectious organisms, such as viruses, parasites and bacteria. These organisms may also be tumor cells. The antigens may be purified or partially purified polypeptides derived from tumors or viral or bacterial sources. The antigens can be recombinant polypeptides produced by expressing DNA encoding the polypeptide antigen in a heterologous expression system. The antigens can be DNA encoding all or part of an antigenic protein. The DNA may be in the form of vector DNA such as plasmid DNA.

Antigens may be provided as single antigens or may be provided in combination. Antigens may also be provided as complex mixtures of polypeptides or nucleic acids.

i. Viral Antigens

A viral antigen can be isolated from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue D1NS3.

Viral antigens may be derived from a particular strain such as a papilloma virus, a herpes virus, i.e. herpes simplex 1 and 2; a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomeglavirus, Epstein-Barr, rotavirus, rhinovirus, adenovirus, coxsackieviruses, equine encephalitis, Japanese encephalitis, yellow fever, Rift Valley fever, and lymphocytic choriomeningitis.

ii. Bacterial Antigens

Bacterial antigens can originate from any bacteria including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus influenza* type B (HIB), *Hyphomicrobium, Legionella, Leptspirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus,* and *Treponema, Vibrio,* and *Yersinia.* iii. Parasite Antigens

Parasite antigens can be obtained from parasites such as, but not limited to, an antigen derived from *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni*. These include Sporozoan antigens, Plasmodian antigens, such as all or part of a Circumsporozoite protein, a Sporozoite surface protein, a liver stage antigen, an apical membrane associated protein, or a Merozoite surface protein.

iv. Allergens and Environmental Antigens

The antigen can be an allergen or environmental antigen, such as, but not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens. Important pollen allergens from trees, grasses and herbs originate from the taxonomic orders of Fagales, Oleales, Pinales and platanaceae including i.a. birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including i.e. grasses of the genera *Lolium, Phleum, Poa, Cynodon, Dactylis, Holcus, Phalaris, Secale,* and *Sorghum,* the orders of Asterales and Urticales including i.a. herbs of the genera *Ambrosia, Artemisia,* and *Parietaria*. Other allergen antigens that may be used include allergens from house dust mites of the genus *Dermatophagoides* and *Euroglyphus*, storage mite e.g *Lepidoglyphys, Glycyphagus* and *Tyrophagus*, those from cockroaches, midges and fleas e.g. *Blatella, Periplaneta, Chironomus* and *Ctenocepphalides*, those from mammals such as cat, dog and horse, birds, venom allergens including such originating from stinging or biting insects such as those from the taxonomic order of Hymenoptera including bees (superfamily Apidae), wasps (superfamily Vespidea), and ants (superfamily Formicoidae). Still other allergen antigens that may be used include inhalation allergens from fungi such as from the genera *Alternaria* and *Cladosporium.* v. Tumor Antigens

The antigen can be a tumor antigen, including a tumor-associated or tumor-specific antigen, such as, but not limited to, alpha-actinin-4, Ber-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triosephosphate isomeras, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15 (58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (Ep-CAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS.

2. Targeting Molecules

Of the main types of antigen-presenting cells (B cell, macrophages and dendritic cells (DCs)), the DC is the most potent and is responsible for initiating all antigen-specific immune responses. Thus, targeting DCs provides the opportunity to enhance the delivery of antigen and antigen responses.

Dendritic cells express a number of cell surface receptors that can mediate the endocytosis of bound antigen. Targeting exogenous antigens to internalizing surface molecules on systemically-distributed antigen presenting cells facilitates uptake of antigens and thus overcomes a major rate-limiting step in immunization and thus in vaccination.

Dendritic cell targeting molecules include monoclonal or polyclonal antibodies or fragments thereof that recognize and bind to epitopes displayed on the surface of dendritic cells. Dendritic cell targeting molecules also include ligands which bind to a cell surface receptor on dendritic cells. One such receptor, the lectin DEC-205, has been used in vitro and in mice to boost both humoral (antibody-based) and cellular (CD8 T cell) responses by 2-4 orders of magnitude (Hawiger, et al., J. Exp. Med., 194(6):769-79 (2001); Bonifaz, et al., J. Exp. Med., 196(12):1627-38 (2002); Bonifaz, et al., J. Exp. Med., 199(6):815-24 (2004)). In these experiments, antigens were fused to an anti-DEC205 heavy chain and a recombinant antibody molecule was used for immunization.

A variety of other endocytic receptors, including a mannose-specific lectin (mannose receptor) and IgG Fc receptors, have also been targeted in this way with similar enhancement of antigen presentation efficiency. Other suitable receptors which may be targeted include, but are not limited to, DC-SIGN, 33D1, SIGLEC-H, DCIR, CD11c, heat shock protein receptors and scavenger receptors.

Other receptors which may be targeted include the toll-like receptors (TLRs). TLRs recognize and bind to pathogen-associated molecular patterns (PAMPs). PAMPs target the TLR on the surface of the dendritic cell and signals internally, thereby potentially increasing DC antigen uptake, maturation and T-cell stimulatory capacity. PAMPs conjugated to the particle surface or co-encapsulated include unmethylated CpG DNA (bacterial), double-stranded RNA (viral), lipopolysacharride (bacterial), peptidoglycan (bacterial), lipoarabinomannin (bacterial), zymosan (yeast), mycoplasmal lipoproteins such as MALP-2 (bacterial), flagellin (bacterial) poly(inosinic-cytidylic) acid (bacterial), lipoteichoic acid (bacterial) or imidazoquinolines (synthetic).

3. Adjuvants

Optionally, the vaccines described herein may include adjuvants. The adjuvant can be, but is not limited to, one or more of the following: oil emulsions (e.g., Freund's adjuvant); saponin formulations; virosomes and viral-like particles; bacterial and microbial derivatives; immunostimulatory oligonucleotides; ADP-ribosylating toxins and detoxified derivatives; alum; BCG; mineral-containing compositions (e.g., mineral salts, such as aluminium salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

Adjuvants may also include immunomodulators such as cytokines, interleukins (e.g., IL-1, IL-2, IL-4, IL-5, IL-6, IL-7, IL-12, etc.), interferons (e.g., interferon-.gamma.), macrophage colony stimulating factor, and tumor necrosis factor. In addition to variant B7-DC polypeptides, other co-stimulatory molecules, including other polypeptides of the B7 family, may be administered. Such proteinaceous adjuvants may be provided as the full-length polypeptide or an active fragment thereof, or in the form of DNA, such as plasmid DNA.

F. Pharmaceutical Compositions

Pharmaceutical compositions including variant B7-DC polypeptides, variant B7-DC fusion proteins, nucleic acids encoding variant B7-DC polypeptides and fusion proteins, and vectors containing the same are provided. The pharmaceutical compositions may be for administration by oral, parenteral (intramuscular, intraperitoneal, intravenous (IV) or subcutaneous injection), transdermal (either passively or using iontophoresis or electroporation), transmucosal (nasal, vaginal, rectal, or sublingual) routes of administration or using bioerodible inserts and can be formulated in dosage forms appropriate for each route of administration. In a preferred embodiment, the peptides are administered in an aqueous solution, particularly for parenteral injection. In general, pharmaceutical compositions are provided including effective amounts of a variant B7-DC polypeptide, fusion proteinor nucleic acid encoding the same, or derivative products, and pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., TWEEN 20, TWEEN 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder (e.g., lyophilized) form.

1. Oral Delivery

Variant B7-DC polypeptides, fusion proteins and nucleic acids encoding the same can be formulated for oral delivery. Oral solid dosage forms are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets, pellets, powders, or granules. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: Modem Pharmaceutics Edited by G. S. Banker and C. T. Rhodes Chapter 10, 1979, herein incorporated by reference. In general, the formulation will include the ABC transporter ligands (or chemically modified forms thereof) and inert ingredients which allow for protection against the stomach environment, and release of the biologically active material in the intestine.

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

The polypeptide antagonists may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. PEGylation is a preferred chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane [see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) J. Appl. Biochem. 4:185-189].

For oral formulations, the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the peptide (or derivative) or by release of the peptide (or derivative) beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (i.e. powder), for liquid forms a soft gelatin shell may be used. The shell material of cachets could be thick starch or other edible paper. For pills, lozenges, molded tablets or tablet triturates, moist massing techniques can be used.

The variant B7-DC polypeptide, variant B7-DC fusion protein or nucleic acid encoding the same (or derivative) can be included in the formulation as fine multiparticulates in the form of granules or pellets of particle size about 1 mm. The formulation of the material for capsule administration could also be as a powder, lightly compressed plugs, or even as tablets. These therapeutics could be prepared by compression.

Colorants and/or flavoring agents may also be included. For example, the sH4 antagonist (or derivative) may be formulated (such as by liposome or microsphere encapsulation) and then further contained within an edible product, such as a refrigerated beverage containing colorants and flavoring agents.

One may dilute or increase the volume of the variant B7-DC polypeptide, variant B7-DC fusion protein or nucleic acid encoding the same (or derivative) with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. The disintegrants may also be insoluble cationic exchange resins. Powdered gums may be used as disintegrants and as binders and can include powdered gums such as agar, Karaya or tragacanth. Alginic acid and its sodium salt are also useful as disintegrants.

Binders may be used to hold the variant B7-DC polypeptide, variant B7-DC fusion protein or nucleic acid encoding the same (or derivative) together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the peptide (or derivative).

An antifrictional agent may be included in the formulation of the sH4 antagonist (or derivative) to prevent sticking during the formulation process. Lubricants may be used as a layer between the peptide (or derivative) and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the peptide (or derivative) into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 20, 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the variant B7-DC polypeptide, variant B7-DC fusion protein or nucleic acid encoding the same (or derivative) are for instance the fatty acids oleic acid, linoleic acid and linolenic acid.

Controlled release oral formulations may be desirable. The variant B7-DC polypeptide, variant B7-DC fusion protein or nucleic acid encoding the same (or derivative) could be incorporated into an inert matrix which permits release by either diffusion or leaching mechanisms, e.g., gums. Slowly degenerating matrices may also be incorporated into the formulation. Some enteric coatings also have a delayed release effect. Another form of a controlled release is by a method based on the Oros therapeutic system (Alza Corp.), i.e. the drug is enclosed in a semipermeable membrane which allows water to enter and push drug out through a single small opening due to osmotic effects.

Other coatings may be used for the formulation. These include a variety of sugars which could be applied in a coating pan. The variant B7-DC polypeptide, variant B7-DC fusion protein or nucleic acid encoding the same (or derivative) could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

2. Parenteral Delivery

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

3. Mucous Membrane Delivery

Compositions for rectal or vaginal administration are preferably suppositories which may contain, in addition to the active substance, excipients such as cocoa butter or a suppository wax. Compositions for nasal or sublingual administration are also prepared with standard excipients well known in the art (see below).

4. Pulmonary Delivery

Also contemplated herein is pulmonary delivery of the sH4 antagonists (or derivatives thereof). The variant B7-DC polypeptide, variant B7-DC fusion protein or nucleic acid encoding the same (or derivative) is delivered to the lungs of a mammal while inhaling and traverses across the lung epithelial lining to the blood stream (see, e.g., Adjei, et al. (1990) Pharmaceutical Research 7:565-569; Adjei, et al. (1990) Int. J. Pharmaceutics 63:135-144 (leuprolide acetate); Braquet, et al. (1989) J. Cardiovascular Pharmacology 13(sup5):143-146 (endothelin-1); Hubbard, et al. (1989) Annals of Internal Medicine, Vol. III, pp. 206-212 ($\alpha$1-antitrypsin); Smith, et al. (1989) J. Clin. Invest. 84:1145-1146 (alpha-1-proteinase); Oswein, et al. (1990) "Aerosolization of Proteins", Proceedings of Symposium on Respiratory Drug Delivery II Keystone, Colorado (recombinant human growth hormone); Debs, et al. (1988) J. Immunol. 140:3482-3488 (interferon-.gamma. and tumor necrosis factor alpha); and U.S. Pat. No. 5,284,656 to Platz, et al. (granulocyte colony stimulating factor). A method and composition for pulmonary delivery of drugs for systemic effect is described in U.S. Pat. No. 5,451,569 to Wong, et al.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices suitable for the practice of this invention are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.).

All such devices require the use of formulations suitable for the dispensing of the variant B7-DC polypeptide, variant B7-DC fusion protein or nucleic acid encoding the same (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified peptides may also be prepared in different formulations depending on the type of chemical modification or the type of device employed.

Formulations suitable for use with a nebulizer, either jet or ultrasonic, will typically comprise peptide (or derivative) dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the peptide (or derivative) caused by atomization of the solution in forming the aerosol.

Formulations for use with a metered-dose inhaler device will generally include a finely divided powder containing the peptide (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will include a finely divided dry powder containing peptide (or derivative) and may also include a bulking agent, such as lactose, sorbitol, sucrose, or mannitol in amounts which facilitate dispersal of the powder from the device, e.g., 50 to 90% by weight of the formulation. The variant B7-DC polypeptide, variant B7-DC fusion protein or nucleic acid encoding the same (or derivative) should most advantageously be prepared in particulate form with an average particle size of less than 10 mm (or microns), most preferably 0.5 to 5 mm, for most effective delivery to the distal lung.

5. Polymeric Matrices

Both non-biodegradable and biodegradable matrices can be used for delivery of variant B7-DC polypeptides, variant B7-DC fusion proteins or nucleic acids encoding the same, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

Representative synthetic polymers that can be used for delivery include polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methylcellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly (ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), poly(vinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof. Examples of biodegradable polymers include synthetic polymers such as polymers of lactic acid and glycolic acid, polyanhydrides, poly(ortho) esters, polyurethanes, poly(butic acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, polyhyaluronic acids, casein, gelatin, glutin, polyanhydrides, polyacrylic acid, alginate, chitosan, poly(methyl methacrylates), poly(ethyl methacrylates), poly(butylmethaerylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), and poly(octadecyl acrylate).

The matrix can be in the form of microparticles such as microspheres, where peptides are dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

The matrices can be formed by solvent evaporation, spray drying, solvent extraction and other methods known to those skilled in the art.

Bioerodible microspheres can be prepared using any of the methods developed for making microspheres for drug delivery, for example, as described by Mathiowitz and Langer, J. Controlled Release 5, 13-22 (1987); Mathiowitz, et al., Reactive Polymers 6, 275-283 (1987); and Mathiowitz, et al., J. Appl. Polymer Sci. 35, 755-774 (1988). The selection of the method depends on the polymer selection, the size, external morphology, and crystallinity that is desired, as described, for example, by Mathiowitz, et al., Scanning Microscopy 4, 329-340 (1990); Mathiowitz, et al., J. Appl. Polymer Sci. 45, 125-134 (1992); and Benita, et al., J. Pharm. Sci. 73, 1721-1724 (1984). In solvent evaporation, described for example, in Mathiowitz, et al., (1990), Benita, and U.S. Pat. No. 4,272,398 to Jaffe, the polymer is dissolved in a volatile organic solvent. The anagonist either in soluble form or dispersed as fine particles, is added to the polymer solution, and the mixture is suspended in an aqueous phase that contains a surface active agent such as poly(vinyl alcohol). The resulting emulsion is stirred until most of the organic solvent evaporates, leaving solid microspheres. In general, the polymer can be dissolved in methylene chloride. Microspheres with different sizes (1-1000 microns) and morphologies can be obtained by this method which is useful for relatively stable polymers such as polyesters and polystyrene. However, labile polymers such as polyanhydrides may degrade due to exposure to water. For these polymers, hot melt encapsulation and solvent removal may be preferred.

In hot melt encapsulation, the polymer is first melted and then mixed with the solid particles of variant B7-DC polypeptide, variant B7-DC fusion protein or nucleic acid encoding the same. The mixture is suspended in a non-miscible solvent such as silicon oil and, with continuous stirring, heated to 5° C. above the melting point of the polymer. Once the emulsion is stabilized, it is cooled until the polymer particles solidify. The resulting microspheres are washed by decantation with petroleum ether to give a free-flowing powder. Microspheres with diameters between one and 1000 microns can be obtained with this method. The external surface of spheres prepared with this technique is usually smooth and dense. This procedure is useful with water labile polymers, but is limited to use with polymers with molecular weights between 1000 and 50000. Solvent removal was primarily designed for use with polyanhydrides. In this method, the variant B7-DC polypeptide, variant B7-DC fusion protein or nucleic acid encoding the same is dispersed or dissolved in a solution of a selected polymer in a volatile organic solvent like methylene chloride. The mixture is then suspended in oil, such as silicon oil, by stirring, to form an emulsion. Within 24 hours, the solvent diffuses into the oil phase and the emulsion droplets harden into solid polymer microspheres. Unlike solvent evaporation, this method can be used to make microspheres from polymers with high melting points and a wide range of molecular weights. Microspheres having a diameter between one and 300 microns can be obtained with this procedure. The external morphology of the spheres is highly dependent on the type of polymer used. In spray drying, the polymer is dissolved in methylene chloride (0.04 g/ml). A known amount of active drug is suspended (if insoluble) or co-dissolved (if soluble) in the polymer solution. The solution or the dispersion is then spray-dried. Double walled microspheres can be prepared according to U.S. Pat. No. 4,861,627 to Mathiowitz.

Hydrogel microspheres made of gel-type polymers such as alginate or polyphosphazines or other dicarboxylic polymers can be prepared by dissolving the polymer in an aqueous solution, suspending the material to be incorporated into the mixture, and extruding the polymer mixture through a microdroplet forming device, equipped with a nitrogen gas jet. The resulting microspheres fall into a slowly stirring, ionic hardening bath, as described, for example, by Salib, et al., Pharmazeutische Industrie 40-11A, 1230 (1978). Chitosan microspheres can be prepared by dissolving the polymer in acidic solution and crosslinking with tripolyphosphate. For example, carboxymethylcellulose (CMC) microsphere are prepared by dissolving the polymer in an acid solution and precipitating the microspheres with lead ions. Alginate/polyethylene imide (PEI) can be prepared to reduce the amount of carboxyl groups on the alginate microcapsules.

Other delivery systems including films, coatings, pellets, slabs, and devices can be fabricated using solvent or melt casting, and extrusion, as well as standard methods for making composites. The polymer can be produced by first mixing monomers and peptides as described by Sawhney, et al., and polymerizing the monomers with UV light. The polymerization can be carried out in vitro as well as in vivo.

II. Methods of Manufacture

A. Methods for Producing Variant B7-DC Polypeptides

Isolated variant B7-DC polypeptides can be obtained by, for example, chemical synthesis or by recombinant production in a host cell. To recombinantly produce a costimulatory polypeptide, a nucleic acid containing a nucleotide sequence encoding the polypeptide can be used to transform, transduce, or transfect a bacterial or eukaryotic host cell (e.g., an insect, yeast, or mammalian cell). In general, nucleic acid constructs include a regulatory sequence operably linked to a nucleotide sequence encoding a costimulatory polypeptide. Regulatory sequences (also referred to herein as expression control sequences) typically do not encode a gene product, but instead affect the expression of the nucleic acid sequences to which they are operably linked.

Useful prokaryotic and eukaryotic systems for expressing and producing polypeptides are well know in the art include, for example, *Escherichia coli* strains such as BL-21, and cultured mammalian cells such as CHO cells.

In eukaryotic host cells, a number of viral-based expression systems can be utilized to express variant B7-DC polypeptides. Viral based expression systems are well known in the art and include, but are not limited to, baculoviral, SV40, retroviral, or vaccinia based viral vectors.

Mammalian cell lines that stably express variant costimulatory polypeptides can be produced using expression vectors with appropriate control elements and a selectable marker. For example, the eukaryotic expression vectors pCR3.1 (Invitrogen Life Technologies) and p91023(B) (see Wong et al. (1985) *Science* 228:810-815) are suitable for expression of variant costimulatory polypeptides in, for example, Chinese hamster ovary (CHO) cells, COS-1 cells, human embryonic kidney 293 cells, NIH3T3 cells, BHK21 cells, MDCK cells, and human vascular endothelial cells (HUVEC). Following introduction of an expression vector by electroporation, lipofection, calcium phosphate, or calcium chloride co-precipitation, DEAE dextran, or other suitable transfection method, stable cell lines can be selected (e.g., by antibiotic resistance to G418, kanamycin, or hygromycin). The transfected cells can be cultured such that the polypeptide of interest is expressed, and the polypeptide can be recovered from, for example, the cell culture supernatant or from lysed cells. Alternatively, a variant B7-DC polypeptide can be produced by (a) ligating amplified sequences into a mammalian expression vector such as pcDNA3 (Invitrogen Life Technologies), and (b) transcribing and translating in vitro using wheat germ extract or rabbit reticulocyte lysate.

Variant costimulatory polypeptides can be isolated using, for example, chromatographic methods such as DEAE ion exchange, gel filtration, and hydroxylapatite chromatography. For example, a costimulatory polypeptide in a cell culture supernatant or a cytoplasmic extract can be isolated using a protein G column. In some embodiments, variant costimulatory polypeptides can be "engineered" to contain an amino acid sequence that allows the polypeptides to be captured onto an affinity matrix. For example, a tag such as c-myc, hemagglutinin, polyhistidine, or Flag™ (Kodak) can be used to aid polypeptide purification. Such tags can be inserted anywhere within the polypeptide, including at either the carboxyl or amino terminus. Other fusions that can be useful include enzymes that aid in the detection of the polypeptide, such as alkaline phosphatase. Immunoaffinity chromatography also can be used to purify costimulatory polypeptides.

B. Methods for Producing Isolated Nucleic Acid Molecules

Isolated nucleic acid molecules can be produced by standard techniques, including, without limitation, common molecular cloning and chemical nucleic acid synthesis techniques. For example, polymerase chain reaction (PCR) techniques can be used to obtain an isolated nucleic acid encoding a variant costimulatory polypeptide. PCR is a technique in which target nucleic acids are enzymatically amplified. Typically, sequence information from the ends of the region of interest or beyond can be employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292-1293.

Isolated nucleic acids can be chemically synthesized, either as a single nucleic acid molecule or as a series of oligonucleotides (e.g., using phosphoramidite technology for automated DNA synthesis in the 3' to 5' direction). For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase can be used to extend the oligonucleotides, resulting in a single, double-stranded nucleic acid molecule per oligonucleotide pair, which then can be ligated into a vector. Isolated nucleic acids can also obtained by mutagenesis. B7-DC encoding nucleic acids can be mutated using standard techniques, including oligonucleotide-directed mutagenesis and/or site-directed mutagenesis through PCR. See, *Short Protocols in Molecular Biology*. Chapter 8, Green Publishing Associates and John Wiley & Sons, edited by Ausubel et al, 1992. Examples of amino acid positions that can be modified include those described herein.

III. Methods of Use

A. Costimulation of T Cells

Variant B7-DC polypeptides, variant B7-DC fusion proteins, nucleic acids encoding variant B7-DC polypeptides or B7-DC fusion proteins, or cells expressing variant B7-DC polypeptides can be used to costimulate T cells (i.e., increase antigen-specific proliferation of T cells, enhance cytokine production by T cells, stimulate differentiation ad effector functions of T cells and/or promote T cell survival).

B7-DC can bind to PD-1 (programmed cell death-1), a CD28 homolog with an immunoreceptor tyrosine-based inhibitory motifinits cytoplasmic domain (Ishida et al. (1992)

*EMBO J.* 11:3887-3895). PD-1 is expressed on a subset of thymocytes and is up-regulated on T cells, B cells, and myeloid cells after their activation (Agata et al. (1996) *Int. Immunol.* 8:765-772). PD-1 appears to be a negative regulator of immune responses in vivo. For example, PD-1$^{-/-}$ mice in the C57BL/6 background slowly developed a lupus-like glomerulonephritis and progressive arthritis (Nishimura et al. (1999) *Immunity* 11:141-151). Additionally, PD-1$^{-/-}$ mice in the BALB/c background rapidly developed a fatal autoimmune dilated cardiomyopathy (Nishimura et al. (2001) *Science* 291:319-322). Evidence also indicates, however, that B7-DC can function to costimulate a T cell response. In the presence of suboptimal TCR signals, B7-DC can stimulate increased proliferation and production of cytokines in vitro. Thus, B7-DC appears to also bind to T cell receptors other than PD-1. The experiments described in the Examples below indicate that the costimulatory activity of B7-DC, and the variants of B7-DC described herein, is not mediated by the PD-1 receptor.

The B7-DC variants described herein demonstrate reduced binding to PD-1 relative to wild type B7-DC, yet retain the ability to costimulate T cells. Thus, the B7-DC variants described herein retain their ability to costimulate T cells and have a reduced ability to suppress T cell activation by binding to PD-1. These B7-DC variants are therefore advantageous over wild type B7-DC for costimulating T cells. Methods for using a variant B7-DC polypeptides and variant B7-DC fusion proteins with reduced affinity for PD-1 to stimulate a T cell response are disclosed herein. The methods can include contacting a T cell with a isolated variant costimulatory polypeptide. The contacting can be in vitro, ex vivo, or in vivo (e.g., in a mammal such as a mouse, rat, rabbit, dog, cow, pig, non-human primate, or a human).

The contacting can occur before, during, or after activation of the T cell. Typically, contacting of the T cell with variant costimulatory polypeptide can be at substantially the same time as activation. Activation can be, for example, by exposing the T cell to an antibody that binds to the T cell receptor (TCR) or one of the polypeptides of the CD3 complex that is physically associated with the TCR. Alternatively, a T cell can be exposed to either an alloantigen (e.g., a MHC alloantigen) on, for example, an APC [e.g., an interdigitating dendritic cell (referred to herein as a dendritic cell), a macrophage, a monocyte, or a B cell] or an antigenic peptide produced by processing of a protein antigen by any of the above APC and presented to the T cell by MHC molecules on the surface of the APC. The T cell can be a CD4$^+$ T cell or a CD8$^+$ T cell.

In some embodiments, a isolated variant costimulatory polypeptide can be administered directly to a T cell. Alternatively, an APC such as a macrophage, monocyte, interdigitating dendritic cell (referred to herein as a dendritic cell), or B cell can be transformed, transduced, or transfected with a nucleic acid containing a nucleotide sequence that encodes a variant costimulatory polypeptide, and the T cell can be contacted by the transformed, transduced, or transfected APC. The transformed, transduced, or transfected cell can be a cell, or a progeny of a cell that, prior to being transformed, transduced, or transfected, was obtained from the subject to which it is administered, or from another subject (e.g., another subject of the same species).

The variant B7-DC polypeptide can be any of those described herein, including any of the disclosed amino acid alterations, polypeptide fragments, fusion proteins and combinations thereof.

If the activation is in vitro, the variant B7-DC molecule can be bound to the floor of a relevant culture vessel, e.g. a well of a plastic microtiter plate.

In vitro application of the isolated variant costimulatory polypeptides can be useful, for example, in basic scientific studies of immune mechanisms or for production of activated T cells for use in studies of T cell function or, for example, passive immunotherapy. Furthermore, variant B7-DC polypeptides can be added to in vitro assays (e.g., T cell proliferation assays) designed to test for immunity to an antigen of interest in a subject from which the T cells were obtained. Addition of variant costimulatory polypeptides to such assays would be expected to result in a more potent, and therefore more readily detectable, in vitro response. Moreover, a variant B7-DC polypeptide, or an APC transformed, transfected, or transduced with a nucleic acid encoding such a polypeptide, can be used: (a) as a positive control in an assay to test for co-stimulatory activity in other molecules; or (b) in screening assays for compounds useful in inhibiting T costimulation (e.g., compounds potentially useful for treating autoimmune diseases or organ graft rejection).

B. Therapeutic Uses of B7-DC Variants

1. Conditions to be Treated

The variant B7-DC polypeptides provided herein are generally useful in vivo and ex vivo as immune response-stimulating therapeutics. In general, the compositions described herein are useful for treating a subject having or being predisposed to any disease or disorder to which the subject's immune system mounts an immune response. The ability of variant B7-DC polypeptides to costimulate T cells makes the disclosed compositions useful to stimulate or enhance immune responses involving T cells. Thus, in a preferred embodiment, the type of disease to be treated or prevented is a malignant tumor or a chronic infectious disease caused by a bacterium, virus, protozoan, helminth, or other microbial pathogen that enters intracellularly and is attacked, i.e., by cytotoxic T lymphocytes. Costimulation of T cells using the variant B7-DC compositions described herein is also advantageous to treat or prevent conditions characterized by immunosuppression.

i. Viral Infections

Because viral infections are cleared primarily by T-cells, an increase in T-cell activity would be therapeutically useful in situations where more rapid or thorough clearance of an infective viral agent would be beneficial to an animal or human subject. Thus, variant B7-DC polypeptides and variant B7-DC fusion proteins can be administered for the treatment of local or systemic viral infections, including, but not limited to, immunodeficiency (e.g., HIV), papilloma (e.g., HPV), herpes (e.g., HSV), encephalitis, influenza (e.g., human influenza virus A), and common cold (e.g., human rhinovirus) viral infections. For example, pharmaceutical formulations of B7-DC compositions factors can be administered topically to treat viral skin diseases such as herpes lesions or shingles, or genital warts. Pharmaceutical formulations of variant B7-DC compositions can also be administered to treat systemic viral diseases, including, but not limited to, AIDS, influenza, the common cold, or encephalitis.

ii. Cancer

Variant B7-DC polypeptides, variant B7-DC fusion proteins and nucleic acids encoding the same may be useful in the induction of tumor immunity. For example, tumor cells, including, but not limited to, sarcoma, melanoma, lymphoma, leukemia, neuroblastoma, or carcinoma cells, can be engineered to carry a nucleic acid encoding a variant B7-DC polypeptide or variant B7-DC fusion protein as described herein, and then administered to a subject to traverse tumor-specific tolerance in the subject. Notably, ectopic expression of B7-1 in B7 negative murine tumor cells has been shown to induce T-cell mediated specific immunity accompanied by tumor rejection and prolonged protection to tumor challenge in mice (L. Chen et al., supra; S. Townsend et al., supra; S. Baskar et al., supra). Tumor or cancer cell gene therapy treatments utilizing 137-related factors may be modeled on animal experiments (see K. Dunussi-Joannopoulos et al. (1997) J. Pediatr. Hematol. Oncol. 19:356-340; K. Hiroishi et al. (1999) Gene Ther. 6:1988-1994; B. K. Martin et al. (1999) J. Immunol. 162:6663-6670; M. Kuiper et al. (2000) Adv. Exp. Med. Biol. 465:381-390), or human phase I trial experiments (H. L. Kaufman et al. (2000) Hum. Gene Ther. 11:1065-1082), which use B7-1 or B7-2 for gene transfer therapy. It will be understood that such methods may be adapted for use with various tumor or cancer cells. Additionally, tumor immunity may be achieved by administration of variant B7-DC polypeptides and variant B7-DC fusion proteins that directly stimulates the immune cells.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated in with the provided compositions and methods include, but are not limited to, the following: bladder, brain, breast, cervical, colo-rectal, esophageal, kidney, liver, lung, nasopharangeal, pancreatic, prostate, skin, stomach, uterine, and the like. Administration is not limited to the treatment of an existing tumor or infectious disease but can also be used to prevent or lower the risk of developing such diseases in an individual, i.e., for prophylactic use. Potential candidates for prophylactic vaccination include individuals with a high risk of developing cancer, i.e., with a personal or familial history of certain types of cancer.

iii. Immunosuppressed Conditions

Variant B7-DC polypeptides and variant B7-DC fusion proteins can be used for treatment of disease conditions characterized by immunosuppression, including, but not limited to, AIDS or AIDS-related complex, other virally or environmentally-induced conditions, and certain congenital immune deficiencies. Variant B7-DC polypeptides and variant B7-DC fusion proteins can also be employed to increase immune function that has been impaired by the use of radiotherapy of immunosuppressive drugs (e.g., certain chemotherapeutic agents), and therefore can be particularly useful when given in conjunction with such drugs or radiotherapy.

2. Use of B7-DC Variants in Vaccines

Variant B7-DC polypeptides, variant B7-DC fusion proteins, and/or nucleic acids encoding the same may be administered alone or in combination with any other suitable treatment. In one embodiment, variant B7-DC polypeptides, variant B7-DC fusion proteins, and/or nucleic acids encoding the same may be administered in conjunction with, or as a component of, a vaccine composition. Suitable components of vaccine compositions are described above. Variant B7-DC compositions described herein can be administered prior to, concurrently with, or after the administration of a vaccine. In one embodiment the variant B7-DC composition is administered at the same time as administration of a vaccine.

The variant B7-DC compositions described herein may be administered in conjunction with prophylactic vaccines, which confer resistance in a subject to subsequent exposure to infectious agents, or in conjunction with therapeutic vaccines, which can be used to initiate or enhance a subject's immune response to a pre-existing antigen, such as a tumor antigen in a subject with cancer, or a viral antigen in a subject infected with a virus.

The desired outcome of a prophylactic, therapeutic or desensitized immune response may vary according to the disease, according to principles well known in the art. For example, an immune response against an infectious agent may completely prevent colonization and replication of an infectious agent, affecting "sterile immunity" and the absence of any disease symptoms. However, a vaccine against infectious agents may be considered effective if it reduces the number, severity or duration of symptoms; if it reduces the number of individuals in a population with symptoms; or reduces the transmission of an infectious agent. Similarly, immune responses against cancer, allergens or infectious agents may completely treat a disease, may alleviate symptoms, or may be one facet in an overall therapeutic intervention against a disease. For example, the stimulation of an immune response against a cancer may be coupled with surgical, chemotherapeutic, radiologic, hormonal and other immunologic approaches in order to affect treatment.

C. Methods of Administration of Variant B7-DC Polypeptides

In some in viva approaches, a variant B7-DC polypeptide or variant B7-DC fusion protein itself is administered to a subject in a therapeutically effective amount. Typically, the polypeptides can be suspended in a pharmaceutically-acceptable carrier. Pharmaceutically acceptable carriers are biologically compatible vehicles (e.g., physiological saline) that are suitable for administration to a human. A therapeutically effective amount is an amount of a variant costimulatory polypeptide that is capable of producing a medically desirable result (e.g., an enhanced T cell response) in a treated animal. Variant B7-DC polypeptides and B7-DC fusion proteins can be administered orally or by intravenous infusion, or injected subcutaneously, intramuscularly, intraperitoneally, intrarectally, intravaginally, intranasally, intragastrically, intratracheally, or intrapulmonarily. The variant costimulatory polypeptides can be delivered directly to an appropriate lymphoid tissue (e.g., spleen, lymph node, or mucosal-associated lymphoid tissue).

D. Methods of Administration of Nucleic Acids and Cells

Nucleic acids encoding variant B7-DC polypeptides or fusion proteins can be administered to subjects in need thereof. Nucleic delivery involves introduction of "foreign" nucleic acids into a cell and ultimately, into a live animal. Several general strategies for gene therapy have been studied and have been reviewed extensively (Yang, N-S., Crit. Rev. Biotechnol. 12:335-356 (1992); Anderson, W. F., Science 256:808-813 (1992); Miller, A. S., Nature 357:455-460 (1992); Crystal, R. G., Amer. J. Med. 92 (suppl 6A):44S-52S (1992); Zwiebel, J. A. et al., Ann. N.Y. Acad. Sci. 618:394-404 (1991); McLachlin, J. R. et al., Prog. Nuc. Acid Res. Molec. Biol. 38:91-135 (1990); Kohn, D. B. et al., Cancer Invest. 7:179-192 (1989), which references are herein incorporated by reference in their entirety).

One approach includes nucleic acid transfer into primary cells in culture followed by autologous transplantation of the ex vivo transformed cells into the host, either systemically or into a particular organ or tissue. In one embodiment, vectors containing nucleic acids encoding variant B7-DC polypeptides are transfected into cells that are administered to a subject in need thereof. In a preferred embodiment the cells containing the vectors containing nucleic acids encoding variant B7-DC polypeptides are antigen presenting cells.

Ex vivo methods can include, for example, the steps of harvesting cells from a subject, culturing the cells, transducing them with an expression vector, and maintaining the cells under conditions suitable for expression of the variant costimulatory polypeptides provided herein. These methods are known in the art of molecular biology. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject.

In some ex vivo methods, peripheral blood mononuclear cells (PBMC) can be withdrawn from a patient or a suitable donor and exposed ex vivo to an activating stimulus (see above) and a variant costimulatory polypeptide (whether in soluble form or attached to a sold support by standard methodologies). The PBMC containing highly activated T cells then can be introduced into the same or a different patient.

An alternative ex vivo strategy can involve transfecting or transducing cells obtained from a subject with a nucleic acid encoding a variant B7-DC polypeptide. The transfected or transduced cells then can be returned to the subject. While such cells typically would be hemopoietic cells (e.g., bone marrow cells, macrophages, monocytes, dendritic cells, or B cells), 20 they can also be any of a wide range of types including, without limitation, fibroblasts, epithelial cells, endothelial cells, keratinocytes, or muscle cells in which they act as a source of the variant B7-DC polypeptide for as long as they survive in the subject. The use of hemopoietic cells, including the above APC, can be particularly useful, as such cells typically are expected to home to, among others, lymphoid tissue (e.g., lymph nodes or spleen) and thus the variant B7-DC polypeptide can be produced in high concentration at the site where its effect (i.e., enhancement of an immune response) is exerted. In addition, if APC are used, the APC expressing the exogenous variant costimulatory molecule can be the same APC that present an alloantigen or antigenic peptide to the relevant T cell. The variant B7-DC can be secreted by the APC or expressed on its surface.

Nucleic acid therapy can be accomplished by direct transfer of a functionally active DNA into mammalian somatic tissue or organ in vivo. For example, nucleic acids encoding B7-DC variant polypeptides can be administered directly to lymphoid tissues. Alternatively, lymphoid tissue specific targeting can be achieved using lymphoid tissue-specific transcriptional regulatory elements (TREs) such as a B lymphocyte-, T lymphocyte-, or dendritic cell-specific TRE. Lymphoid tissue specific TREs include, for example, those known in the art [see, e.g., Thompson et al. (1992) *Mol. Cell. Biol.* 12:1043-1053; Todd et al. (1993) *J. Exp. Med.* 177: 1663-1674; and Penix et al. (1993) *J. Exp. Med.* 178:1483-1496].

DNA transfer can be achieved using a number of approaches described below. These systems can be tested for successful expression in vitro by use of a selectable marker (e.g., G418 resistance) to select transfected clones expressing the DNA, followed by detection of the presence of the B7-H4 expression product (after treatment with the inducer in the case of an inducible system) using an antibody to the product in an appropriate immunoassay. Efficiency of the procedure, including DNA uptake, plasmid integration and stability of integrated plasmids, can be improved by linearizing the plasmid DNA using known methods, and co-transfection using high molecular weight mammalian DNA as a "carrier".

Examples of successful "gene transfer" reported in the art include: (a) direct injection of plasmid DNA into mouse muscle tissues, which led to expression of marker genes for an indefinite period of time (Wolff, J. A. et al., Science 247:1465 (1990); Acsadi, G. et al., The New Biologist 3:71 (1991)); (b) retroviral vectors are effective for in vivo and in situ infection of blood vessel tissues; (c) portal vein injection and direct injection of retrovirus preparations into liver effected gene transfer and expression in vivo (Horzaglou, M. et al., J. Biol. Chem. 265:17285 (1990); Koleko, M. et al., Human Gene Therapy 2:27 (1991); Ferry, N. et al., Proc. Natl. Acad. Sci. USA 88:8387 (1991)); (d) intratracheal infusion of recombinant adenovirus into lung tissues was effective for in vivo transfer and prolonged expression of foreign genes in lung respiratory epithelium (Rosenfeld, M. A. et al., Science 252: 431 (1991); (e) Herpes simplex virus vectors achieved in vivo gene transfer into brain tissue (Ahmad, F. et al., eds, Miami Short Reports—Advances in Gene Technology: The Molecular Biology of Human Genetic Disease, Vol 1, Boerringer Manneheim Biochemicals, USA, 1991).

Retroviral-mediated human therapy utilizes amphotrophic, replication-deficient retrovirus systems (Temin, H. M., Human Gene Therapy 1:111 (1990); Temin et al., U.S. Pat. No. 4,980,289; Temin et al., U.S. Pat. No. 4,650, 764; Temin et al., U.S. Pat. No. 5,124,263; Wills, J. W. U.S. Pat. No. 5,175,099; Miller, A. D., U.S. Pat. No. 4,861,719). Such vectors have been used to introduce functional DNA into human cells or tissues, for example, the adenosine deaminase gene into lymphocytes, the NPT-II gene and the gene for tumor necrosis factor into tumor infiltrating lymphocytes. Retrovirus-mediated gene delivery generally requires target cell proliferation for gene transfer (Miller, D. G. et al., Mol. Cell. Biol. 10:4239 (1990). This condition is met by certain of the preferred target cells into which the present DNA molecules are to be introduced, i.e., actively growing tumor cells. Gene therapy of cystic fibrosis using transfection by plasmids using any of a number of methods and by retroviral vectors has been described by Collins et al., U.S. Pat. No. 5,240,846.

Nucleic acid molecules encoding variant B7-DC polypeptides or fusion proteins may be packaged into retrovirus vectors using packaging cell lines that produce replication-defective retroviruses, as is well-known in the art (see, for example, Cone, R. D. et al., Proc. Natl. Acad. Sci. USA 81:6349-6353 (1984); Mann, R. F. et al., Cell 33:153-159 (1983); Miller, A. D. et al., Molec. Cell. Biol. 5:431-437 (1985); Sorge, J., et al., Molec. Cell. Biol. 4:1730-1737 (1984); Hock, R. A. et al., Nature 320:257 (1986); Miller, A. D. et al., Molec. Cell. Biol. 6:2895-2902 (1986). Newer packaging cell lines which are efficient and safe for gene transfer have also been described (Bank et al., U.S. Pat. No. 5,278, 056).

This approach can be utilized in a site specific manner to deliver the retroviral vector to the tissue or organ of choice. Thus, for example, a catheter delivery system can be used (Nabel, E G et al., Science 244:1342 (1989)). Such methods, using either a retroviral vector or a liposome vector, are particularly useful to deliver the nucleic acid to be expressed to a blood vessel wall, or into the blood circulation of a tumor.

Other virus vectors may also be used, including recombinant adenoviruses (Horowitz, M. S., In: Virology, Fields, B N et al., eds, Raven Press, New York, 1990, p. 1679; Berkner, K. L., Biotechniques 6:616 9191988), Strauss, S. E., In: The Adenoviruses, Ginsberg, H S, ed., Plenum Press, New York, 1984, chapter 11), herpes simplex virus (HSV) for neuron-specific delivery and persistence. Advantages of adenovirus vectors for human gene therapy include the fact that recombination is rare, no human malignancies are known to be associated with such viruses, the adenovirus genome is double stranded DNA which can be manipulated to accept foreign genes of up to 7.5 kb in size, and live adenovirus is a safe human vaccine organism. Adeno-associated virus is also useful for human therapy (Samulski, R. J. et al., EMBO J. 10:3941 (1991).

Another vector which can express the disclosed DNA molecule and is useful in the present therapeutic setting, particularly in humans, is vaccinia virus, which can be rendered non-replicating (U.S. Pat. Nos. 5,225,336; 5,204,243; 5,155,020; 4,769,330; Sutter, G et al., Proc. Natl. Acad. Sci. USA (1992) 89:10847-10851; Fuerst, T. R. et al., Proc. Natl. Acad. Sci. USA (1989) 86:2549-2553; Falkner F. G. et al.; Nucl. Acids Res (1987) 15:7192; Chakrabarti, S et al., Molec. Cell. Biol. (1985) 5:3403-3409). Descriptions of recombinant vaccinia viruses and other viruses containing heterologous DNA and their uses in immunization and DNA therapy are reviewed in: Moss, B., Curr. Opin. Genet. Dev. (1993) 3:86-90; Moss, B. Biotechnology (1992) 20: 345-362; Moss, B., Curr Top Microbiol Immunol (1992) 158:25-38; Moss, B., Science (1991) 252:1662-1667; Piccini, A et al., Adv. Virus Res. (1988) 34:43-64; Moss, B. et al., Gene Amplif Anal (1983) 3:201-213.

In addition to naked DNA or RNA, or viral vectors, engineered bacteria may be used as vectors. A number of bacterial strains including *Salmonella*, BCG and *Listeria monocytogenes* (LM) (Hoiseth & Stocker, Nature 291, 238-239 (1981); Poirier, T P et al. J. Exp. Med. 168, 25-32 (1988); (Sadoff, J. C., et al., Science 240, 336-338 (1988); Stover, C. K., et al., Nature 351, 456-460 (1991); Aldovini, A. et al., Nature 351, 479-482 (1991); Schafer, R., et al., J. Immunol. 149, 53-59 (1992); Ikonomidis, G. et al., J. Exp. Med. 180, 2209-2218 (1994)). These organisms display two promising characteristics for use as vaccine vectors: (1) enteric routes of infection, providing the possibility of oral vaccine delivery; and (2) infection of monocytes/macrophages thereby targeting antigens to professional APCs.

In addition to virus-mediated gene transfer in vivo, physical means well-known in the art can be used for direct transfer of DNA, including administration of plasmid DNA (Wolff et al., 1990, supra) and particle-bombardment mediated gene transfer (Yang, N. -S., et al., Proc. Natl. Acad. Sci. USA 87:9568 (1990); Williams, R. S. et al., Proc. Natl. Acad. Sci. USA 88:2726 (1991); Zelenin, A. V. et al., FEBS Lett. 280:94 (1991); Zelenin, A. V. et al., FEBS Lett. 244:65 (1989); Johnston, S. A. et al., In Vitro Cell. Dev. Biol. 27:11 (1991)). Furthermore, electroporation, a well-known means to transfer genes into cell in vitro, can be used to transfer DNA molecules to tissues in vivo (Titomirov, A. V. et al., Biochim. Biophys. Acta 1088:131 ((1991)).

"Carrier mediated gene transfer" has also been described (Wu, C. H. et al., J. Biol. Chem. 264:16985 (1989); Wu, G. Y. et al., J. Biol. Chem. 263:14621 (1988); Soriano, P. et al., Proc. Natl. Acad. Sci. USA 80:7128 (1983); Wang, C-Y. et al., Proc. Natl. Acad. Sci. USA 84:7851 (1982); Wilson, J. M. et al., J. Biol. Chem. 267:963 (1992)). Preferred carriers are targeted liposomes (Nicolau, C. et al., Proc. Natl. Acad. Sci. USA 80:1068 (1983); Soriano et al., supra) such as immuno-liposomes, which can incorporate acylated mAbs into the lipid bilayer (Wang et al., supra). Polycations such as asia-loglycoprotein/polylysine (Wu et al., 1989, supra) may be used, where the conjugate includes a molecule which recognizes the target tissue (e.g., asialoorosomucoid for liver) and a DNA binding compound to bind to the DNA to be transfected. Polylysine is an example of a DNA binding molecule which binds DNA without damaging it. This conjugate is then complexed with plasmid DNA.

Plasmid DNA used for transfection or microinjection may be prepared using methods well-known in the art, for example using the Quiagen procedure (Quiagen), followed by DNA purification using known methods, such as the methods exemplified herein.

E. Dosages

For variant B7-DC polypeptides, variant B7-DC fusion proteins, nucleic acids encoding B7-DC polypeptides and variant B7-DC fusion proteins, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage may be lower.

EXAMPLES

The present invention may be further understood by reference to the following non-limiting examples.

Example 1

Molecular Modeling of B7-DC and Sequence Analysis in Three Dimensions

Materials and Methods:

Molecular models of the Ig V-type domains of human B7-H1 (hB7-H1), mouse 137-H1 (mB7-H1), human B7-DC (hB7-DC), and mouse B7-DC (mB7-DC) were generated by homology (or comparative) modeling based on X-ray coordinates of human CD80 and CD86, as seen in the structures of the CD80/CTLA-4 and CD86/CTLA-4 complexes. First, the V-domains of CD80 and CD86 were optimally superimposed, and sequences of B7 family members were aligned based on this superimposition. The superimposition and initial alignments were carried out using the sequence-structure alignment function of MOE (Molecular Operating Environment, Chemical Computing Group, Montreal, Quebec, Canada). The alignment was then manually adjusted to match Ig consensus positions and to map other conserved hydrophobic residues in the target sequences to core positions in the X-ray structures. Corresponding residues in the aligned sequences thus were predicted to have roughly equivalent spatial positions. Taking this kind of structural information into account typically is a more reliable alignment criterion than sequence identity alone if the identity is low, as in this case. In the aligned region, the average identity of the compared B7 sequences relative to the two structural templates, CD80 and CD86, was only approximately 16%. The final version of the structure-oriented sequence alignment, which provided the basis for model building, is shown in FIG. 5. Following the alignment, core regions of the four models were automatically assembled with MOE from the structural templates, and insertions and deletions in loop regions were modeled by applying a segment matching procedure (Levitt, *J. Mol. Biol.*, 226:507-533 (1992); and Fechteler, et al., *J. Mol. Biol.*, 253:114-131 (1995)). Side chain replacements were carried out using preferred rotamer conformations seen in high-resolution protein databank structures (Ponder and Richards, *J. Mol. Biol.*, 193:775-791 (1987); and Berman, et al., *Nucl. Acids Res.*, 28:235-242 (2000)). In each case, twenty intermediate models were generated, average coordinates were calculated, and the resulting structures were energy minimized using a protein force field (Engh and Huber, *Ada Cryst.*, A47:392-400 (1991)) until intramolecular contacts and stereochemistry of each model were reasonable. Graphical analysis of the models, including calculation of solvent-accessible surfaces (Connolly, *J. Appl. Cryst.*, 16:548-558 (1983)) and residue mapping studies were carried out with InsightII (Accelrys, San Diego, Calif.).

Results:

The V-regions in CD80 and CD86 share only limited sequence identity (approximately 20%), but their three-dimensional structures are very similar as revealed by independent crystallographic studies. Many core or Ig superfamily consensus residue positions seen in CD80/CD86 also are conserved or conservatively replaced in other B7 family members, including B7-H1 and B7-DC (FIG. 5).

Molecular models of mouse and human B7-H1 and B7-DC molecules were constructed. These models revealed that in the V-regions, B7-H1 and B7-DC share more sequence identity than average across the B7 family—approximately 34%. Since both B7-H1 and B7-DC bind PD-1, residue conservation could be significant for formation of the receptor binding structure. Therefore, the models were used to compare the putative distribution of conserved residues that are exposed on the protein surface. A side-by-side comparison of these molecular models revealed significant conservation of surface residues on the BED faces of B7-H1 and B7-DC, more so in the human than the mouse proteins. In contrast, the opposite A'GFCC'C" faces did not display significant residue conservation. This result was somewhat unexpected because the corresponding A'GFCC'C" faces of both CD80 and CD86 contain the CD28/CTLA-4 binding sites.

Example 2

Mutagenesis Analysis of Receptor Binding Sites

Materials and Methods:
Mice and Cell Lines:

Female C57BL/6 (B6) mice were purchased from the National Cancer Institute (Frederick, Md.). PD-1-deficient (PD-1$^{-/-}$) mice were generated as described previously (Nishimura, et al., *Int. Immunol.*, 10:1563-1572 (1998)). Stably transfected Chinese hamster ovary (CHO) cell clones secreting fusion proteins were maintained in CHO-SF II medium (Invitrogen Life Technologies) supplemented with 1% dialyzed fetal bovine serum (FBS; HyClone, Logan, Utah). Lymphocytes and COS cells were grown in Dulbecco's modified Eagle medium (DMEM; Invitrogen Life Technologies) supplemented with 10% FBS, 25 mM HEPES, 2 mM L-glutamine, 1 mM sodium pyruvate, 1% MEM nonessential amino acids, 100 U/ml penicillin G, and 100 µg/ml streptomycin sulfate.

Site-Directed Mutagenesis:

All variants of B7-DCIg were constructed using a two-step PCR technique using B7-DCIg cDNA as a template. Overlapping oligonucleotide primers were synthesized to encode the desired mutations, and two flanking 5' and 3' primers were designed to contain EcoR I and Bgl II restriction sites, respectively. Appropriate regions of the cDNAs initially were amplified using the corresponding overlapping and flanking primers. Using the flanking 5' and 3' primers, fragments with overlapping sequences were fused together and amplified. PCR products were digested with EcoR I and Bgl II and ligated into EcoR I/Bgl II-digested pHIg vectors. To verify that the desired mutations were introduced, each variant was sequenced using an ABI Prism 310 Genetic Analyzer. Plasmids were transfected into COS cells, and serum-free supernatants were harvested and used for in vitro binding assays or isolated on a protein G column for BIAcore analysis and functional assays.

Ig Fusion Proteins:

Fusion proteins containing the extracellular domain of mouse PD-1 linked to the Fc portion of mouse IgG2a (PD-1 Ig) were produced in stably transfected CHO cells and isolated by protein G affinity column as described previously (Wand, et al. supra). Total RNA was isolated from mouse spleen cells and B7-DC cDNA was obtained by reverse-transcription PCR. Murine B7-DCIg was prepared by transiently transfecting COS cells with a plasmid containing a chimeric cDNA that included the extracellular domain of mouse B7-DC linked in frame to the CH2-CH3 portion of human IgG1. Human B7-DCIg was prepared by transiently transfecting COS cells with a plasmid containing a chimeric cDNA that included the extracellular domain of human B7-DC linked in frame to the CH2-CH3 portion of human IgG1. The transfected COS cells were cultured in serum-free DMEM, and concentrated supernatants were used as sources of Ig fusion proteins for initial binding assays. The Ig proteins were further isolated on a protein G column for BIAcore analysis and functional assays as described previously (Wand, et al. supra).

ELISA:

A sandwich ELISA specific for B7-DCIg was established. Microtiter plates were coated with 2 fig/ml goat anti-human IgG (Sigma, St. Louis, Mo.) overnight at 4° C. Wells were blocked for 1 hour with blocking buffer (10% FBS in PBS) and washed with PBS containing 0.05% Tween 20 (PBS-Tween). COS cell culture supernatants were added and incubated for 2 hours at room temperature. Known concentrations of isolated B7-DCIg also were added to separate wells on each plate for generation of a standard curve. After extensive washing, horseradish peroxidase (HRP)-conjugated goat anti-human IgG (TAGO, Inc., Burlingame, Calif.) diluted 1:2000 was added and subsequently developed with TMB substrate before stopping the reaction by the addition of 0.5 M $H_2SO_4$. Absorbance was measured at 405 mm on a microtiter plate reader. Concentrations of variant fusion proteins were determined by comparison with the linear range of a standard curve of B7-DClg. Data from triplicate wells were collected, and the standard deviations from the mean were <10%. Experiments were repeated at least three times.

The ability of mutant and wild type B7-DCIg fusion polypeptides to bind PD-1 was measured using a capture ELISA assay. Recombinant PD-1Ig fusion proteins were coated on microtiter plates at 5 µg/ml overnight at 4° C. The plates were blocked and washed, and COS cell culture media was added and incubated for 2 hours at room temperature. After extensive washing, HRP-conjugated goat anti-human IgG was added, followed by TMB substrate and measurement of absorbance at 405 mm.

Flow Cytometry:

Human embryonal kidney 293 cells were transfected with a PD-1 GFP vector, which was constructed by fusing GFP (green fluorescent protein cDNA) in frame to the C terminal end of a full-length mouse PD-1 cDNA. The cells were harvested 24 hours after transfection and incubated in FACS (fluorescence activated cell sorting) buffer (PBS, 3% FBS, 0.02% NaN$_3$) with equal amounts of fusion proteins, which had been titrated using wild type B7-DCIg in COS cell culture media on ice for 45 minutes. An unrelated fusion protein containing human Ig was used as a negative control. The cells were washed, further incubated with fluorescein isothiocyanate (PE)-conjugated goat anti-human IgG (BioSource, Camarillo, Calif.), and analyzed on a FACScaliber (Becton Dickinson, Mountain View, Calif.) with Cell Quest software (Becton Dickinson). GFP-positive cells were gated by FL1.

Surface Plasmon Resonance Analysis:

The affinity of isolated wild type and variant B7-DC polypeptides was analyzed on a BIAcore™ 3000 instrument (Biacore AB, Uppsala, Sweden). All reagents except fusion proteins were purchased, pre-filtered, and degassed from BIAcore. All experiments were performed at 25° C. using 0.1 M HEPES, 0.15 M NaCl (pH 7.4) as a running buffer. Briefly, PD-1 Ig was first immobilized onto a CM5 sensor chip (BIAcore) by amine coupling according to the BIAcore protocol. A flow cell of the CM5 chip was derivatized through injection of a 1:1 EDC:NHS [N-ethyl-N'-(diethylaminopropyl) carbodiimide:N-hydroxysuccinimide] mixture for seven minutes, followed by injection of 20 µg/ml of PD-1Ig at 10 µl/min diluted in 10 mM sodium acetate (pH 4.5). The PD-1Ig was immobilized at 2000 RUs. This was followed by blocking the remaining activated carboxyl groups with 1 M ethanolamine (pH 8.5). A control flow cell was prepared in a similar fashion as above, substituting running buffer alone in place of PD-1Ig. The fusion proteins were diluted in running buffer in a concentration series of 3.75, 7.5, 15, 30, and 60 µg/ml. The proteins were injected at a flow rate of 20 µl/min for 3 minutes, and buffer was allowed to flow over the surface for 5 minutes for dissociation data. The flow cells were regenerated with a single 30-second pulse of 10 mM NaOH. Data analysis was performed using BIAevaluation software package 3.1 (BIAcore).

Results:

With the aid of the molecular models, the V-domain of B7-DC was scanned for important residues. Conserved and non-conserved residues on both the BED and A'GFCC'C" faces were selected for site-specific mutagenesis. Residues in the mouse molecules were mutated to enable subsequent functional studies of selected mutant proteins. The binding characteristics of the resulting variant polypeptides were assessed by specific ELISA and FACS analysis for binding to PD-1. A total of 17 mB7-DC variants were prepared and tested. The results are summarized in Table 1. Particular residues within mB7-DC were only considered to be important for ligand-receptor interactions if their mutation caused at least a 50% loss of binding by FACS, or at least an order of magnitude loss by ELISA.

Mutation of about half of these residues significantly abolished binding to mPD-1. In particular, mB7-DC residues E71, I105, D111, and K113 were identified as important for binding to mPD1. Mutation of residue S58 in mB7-DC increased binding to mPD-1 as determined by ELISA. Thus, this residue must at least be proximal to the receptor-ligand interface and have not only some tolerance for substitution but also potential optimization of binding interactions.

Variants of human B7-DC were also tested for binding to PD-1 using ELISA and FACS analysis. Mutation of hB7-DC residues K113 and D111 were identified as important for binding to PD-1. FACS analysis results are shown in FIG. 7.

TABLE 1

Summary of amino acid substitutions and binding characteristics of mouse B7-DC mutants

| Mutants[a] | Sites | Substitutions[b] Nucleic acids(s) | Amino acid | PD-1 binding FACS[c] | ELISA (%)[d] |
|---|---|---|---|---|---|
| B7-DC | | | | ++++ | 100 |
| D33S | A' strand | GAC→AGC | D→S | ++++ | 30 |
| S39Y | B strand | AGC→TAC | S→Y | ++++ | 60 |
| E41S | B strand | GAG→AGC | E→S | ++++ | 100 |
| R56S | C strand | AGA→TCT | R→S | +++/++ | 5 |
| S58Y | C strand | AGT→TAC | S→Y | ++++ | 170 |
| D65S | C' strand | GAT→AGC | D→S | ++++ | 100 |
| S67Y | C'strand | TCT→TAC | S→Y | +++/++ | 3 |
| E71S | C" strand | GAA→AGC | E→S | +++/++ | 2 |
| R72S | C" strand | AGA→AGC | R→S | ++++ | 60 |
| K84S | D strand | AAG→AGC | K→S | +++/++++ | 13 |
| H88A | E strand | CAC→GCC | H→A | +++/++++ | 20 |
| R101S | F strand | CGT→AGC | R→S | +++ | 7 |
| L103A | F strand | CTG→GCC | L→A | +++ | 25 |
| I105A | F strand | ATC→GCC | I→A | ++ | 0.5 |
| D111S | G strand | GAC→AGC | D→S | ++ | 0.3 |
| K113S | G strand | AAG→AGC | K→S | −/+ | <0.1 |
| T116Y | G strand | ACG→TAC | T→Y | +++/++++ | 20 |

The PD-1 binding sites mapped to equivalent regions on the opposite A'GFCC'C" face. Mapping of the binding site regions revealed that residues whose mutation negatively (or positively) affected PD-1 binding could form coherent surfaces in both ligands. The proximity of important residues and some residues not important for binding again suggested that the observed effects were specific, and were not a consequence of global structural changes. Comparison of important residue positions confirmed that the location of the putative binding sites in mB7-DC closely corresponded to the CD28/CTLA-4 binding sites in CD86 and CD80.

Figure 6:
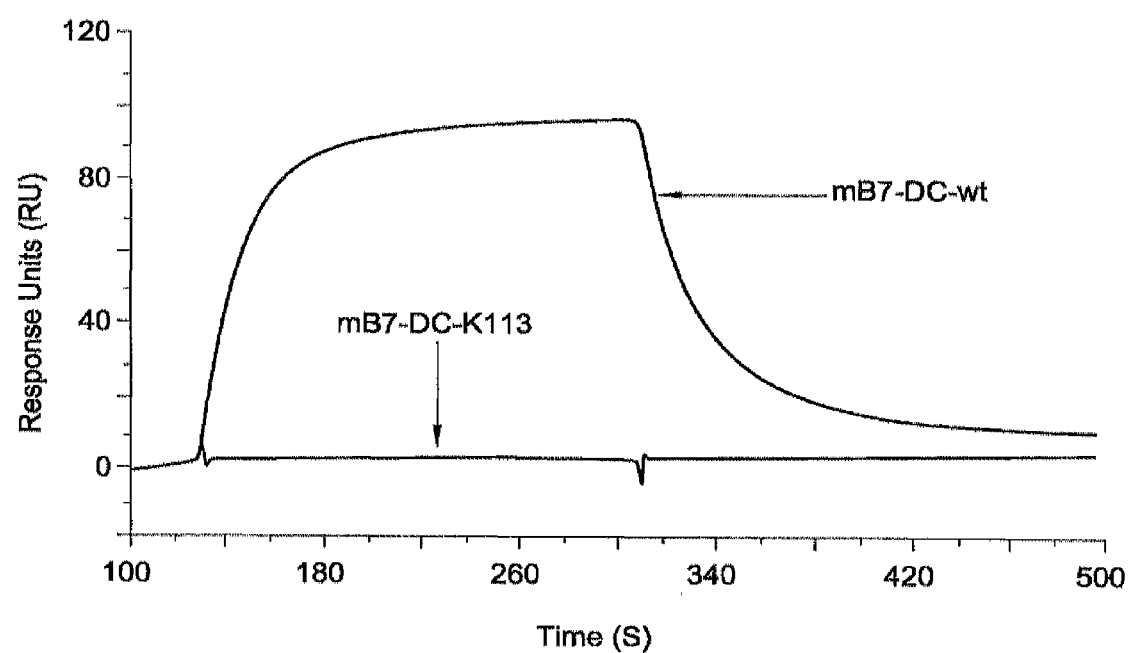
Figure 7A:
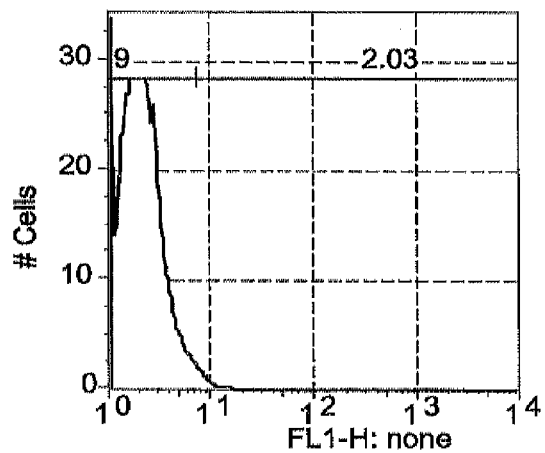
Figure 7B:
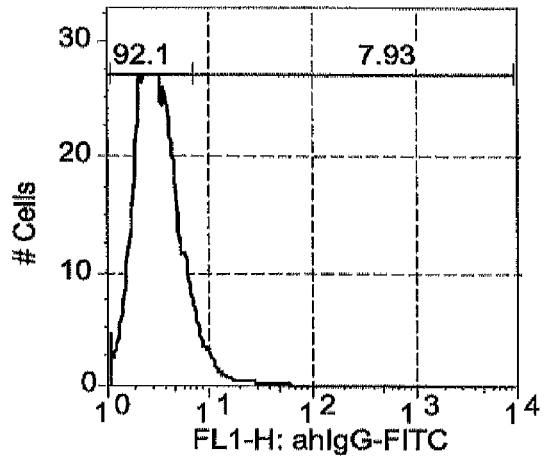
Figure 7C:
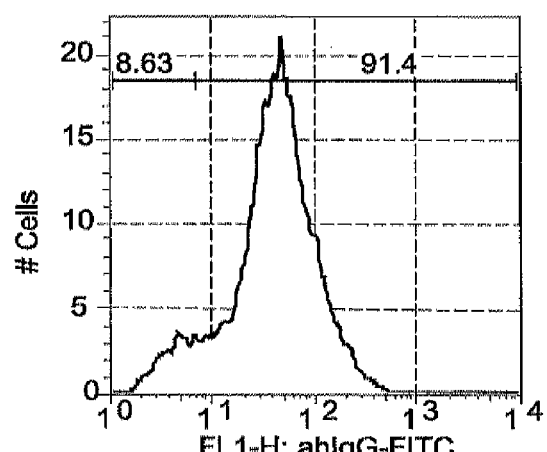
Figure 7D:
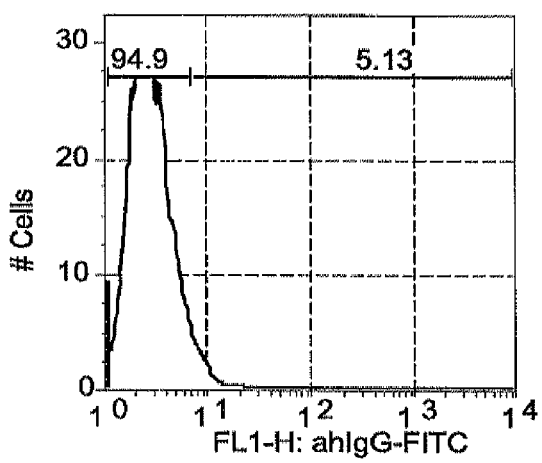
Figure 7E:
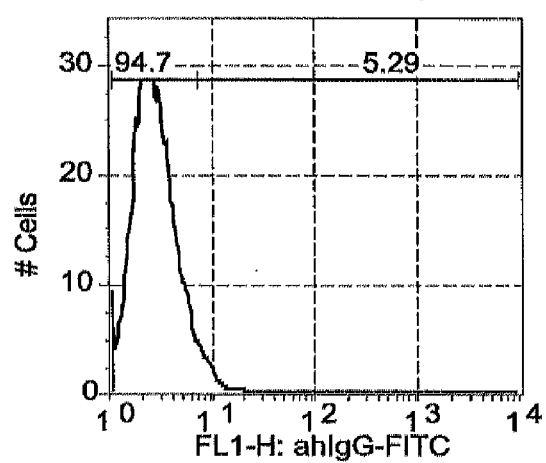
Figure 7F:
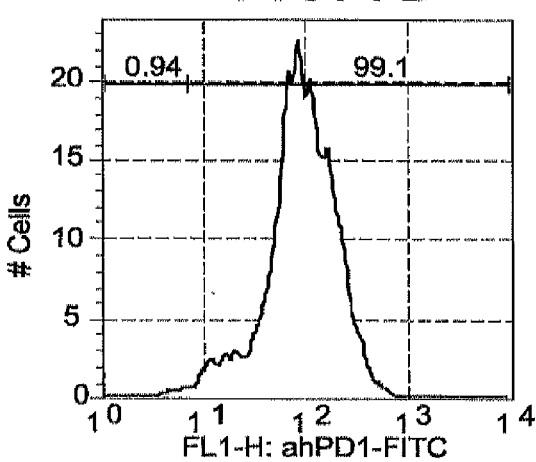

Surface plasmon resonance analysis of binding of wild type and mutant proteins to PD-1 was largely consistent with the results from the FACS and ELISA analyses. The wild type B7-DC protein had an R$_{max}$ of 227 RU, and the B7-DC variant K113 did not bind to PD-1 at all (FIG. 6). These data demonstrated that wild type B7-DC had a greater steady state affinity for PD-1 than mutant K113. The B7-DC K113 variant showed slower or no on- and off-rates, as compared to wild type B7-DC.

Example 3

Costimulatory Function of B7-DC Variants

Materials and Methods:
T Cell Proliferation and Cytokine Assays:

T cells from wild type B6 mice or PD-1$^{-/-}$ mice were isolated using nylon wool columns (Robbins Scientific Co, Sunnyvale, Calif.) as described previously (Wang, et al. supra). The enriched T cells were cultured at 3×10$^5$ cells per well in flat-bottomed 96-well microplates that were pre-coated with anti-CD3 mAb (clone 145-2C11, Pharmingen, San Diego, Calif.) in the presence of 5 µg/ml of fusion or control polypeptides. Proliferation of T cells was determined by incorporation of 1 µCi/well $^3$H-TdR during the last 12 hours of the 3-day culture. $^3$H-TdR incorporation was counted using a MicroBeta Trilux liquid scintillation counter (Wallac, Finland). To detect cytokine, culture supernatants were collected at various time points, and the concentration of IFN-γ was measured by sandwich ELISA following the manufacturer's instructions (Pharmingen).

Figure 8A:
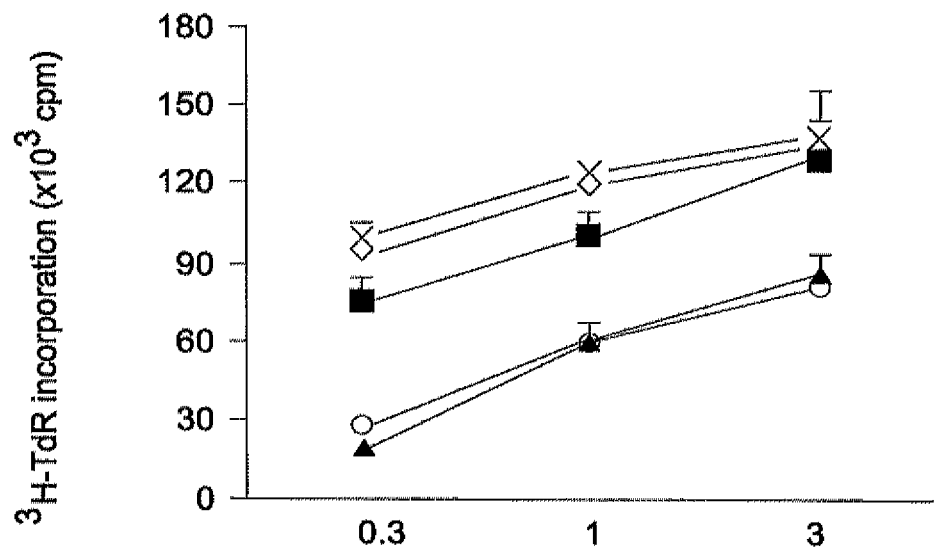
Figure 8B:
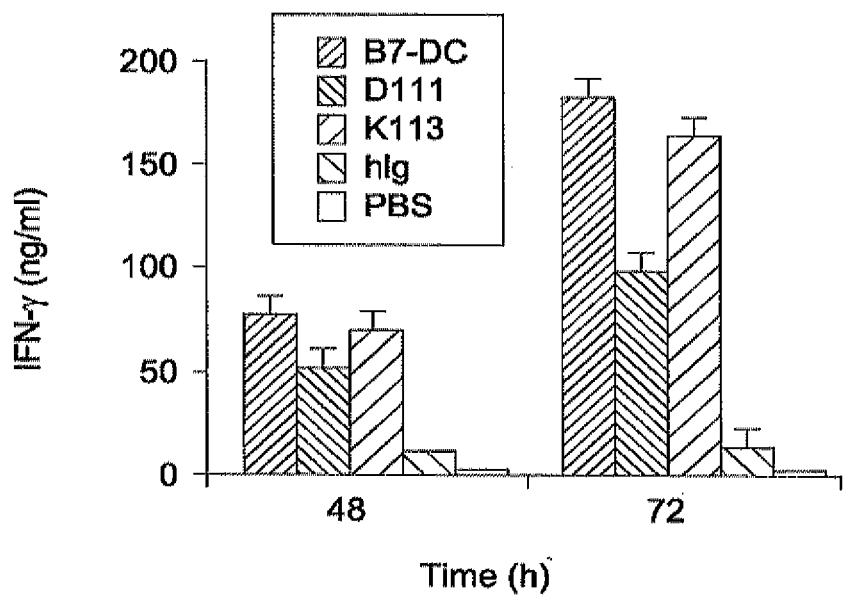

Results:

The costimulatory potential of selected variants also was tested. B7-DC variants K113 and D111 were selected for analysis. Both K113 and Dill had minimal binding to PD-1 in both FACS and ELISA assays (Table 1). As shown in FIGS. 8A and 8B, these variants were still able to costimulate T cell proliferation and IFN-γ production in comparison with wild type B7-DC.

Figure 9:
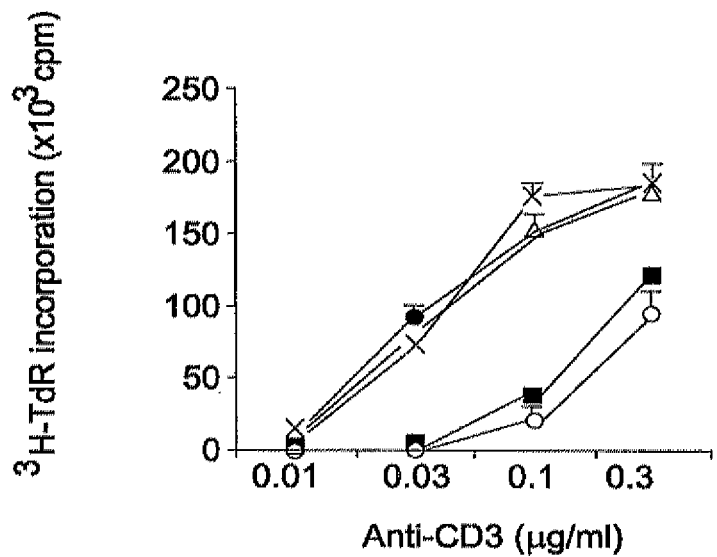

Although B7-DC might costimulate T cell growth through a yet unknown receptor, these findings could be interpreted as an integrated stimulatory effect of unidentified costimulatory receptor(s) and PD-1. Therefore, the costimulatory effects of B7-DC variants were tested in PD-1 deficient T cells. Wild type and variant B7-DC polypeptides costimulated proliferation of PD-1$^{-/-}$ T cells as well as or better than PD-1$^{+/+}$ cells (FIG. 9 as compared with FIG. 8A). Thus, these observations strongly suggest that B7-DC costimulates T cell growth through a non-PD-1 receptor.

Example 4

Effect of Wild-type and Variant B7-DC on Growth of Tumor Cells in Syngeneic Immunocompetent and Immunocompromised Mice The Examples above indicate that B7-DC mutants, which lose binding to inhibitory receptor program death-1 (PD-1), retain costimulatory function for T cells. These results indicate that B7-DC mutants could be applied to enhance antitumor immune responses. Therefore, the capacity of B7-DC and B7-DC variants to stimulate antitumor immunity in whole animals was examined. The plasmid K113S B7-DC, which contains cDNA encoding a point mutation was transfected into a murine tumor line EG7 by electroporation. EG7 cell lines which stably express K113S B7-DC were established. Expression of B7-DC on the cell surface of a subline of EG7 transfectants, EG7/K113S, was demonstrated by flow cytometry analysis using specific monoclonal antibody to B7-DC. EG7 cells were also transfected with either parent plasmid (mock) as negative control or the plasmid containing wild type B7-DC (EG7/Wt B7-DC) as an additional control. Mock EG7 transfected cells do not express detectable B7-DC while wt B7-DC stable transfectants express a comparable level of B7-DC as cells stably transfected with K113S B7-DC.

Figure 10:
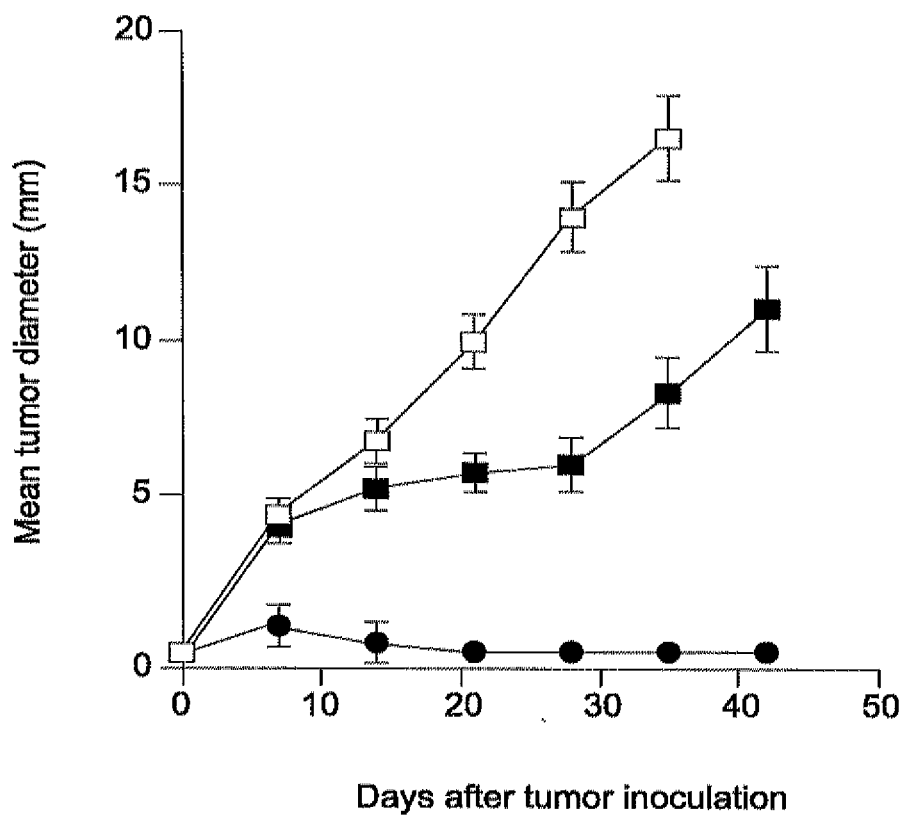
FIG. 10 is a line graph showing growth (mean tumor diameter in millimeters) of EG7 murine tumor cells that were either mock transfected (-□-) or transfected with wild-type B7-DC (-■-) or K113S B7-DC (-●-) in syngeneic immunocompetent (C57BL/6) mice as a function of time (days).

Subcutaneous inoculation of EG7/K113S cells into 10 syngeneic immunocompetent C57BL/6 mice induced transient growth of tumors as nodules. However, these tumors regressed rapidly. At day 20, all tumors disappeared completely. In contrast, inoculation of mock EG7 line induced progressively growing tumors and eventually killed the mice in 30-40 days. Inoculation of mice with cells of the Wt B7-DC line also induced progressively growing tumors. However, their growth was much slower than mock EG7 line (FIG. 10).

Figure 11:
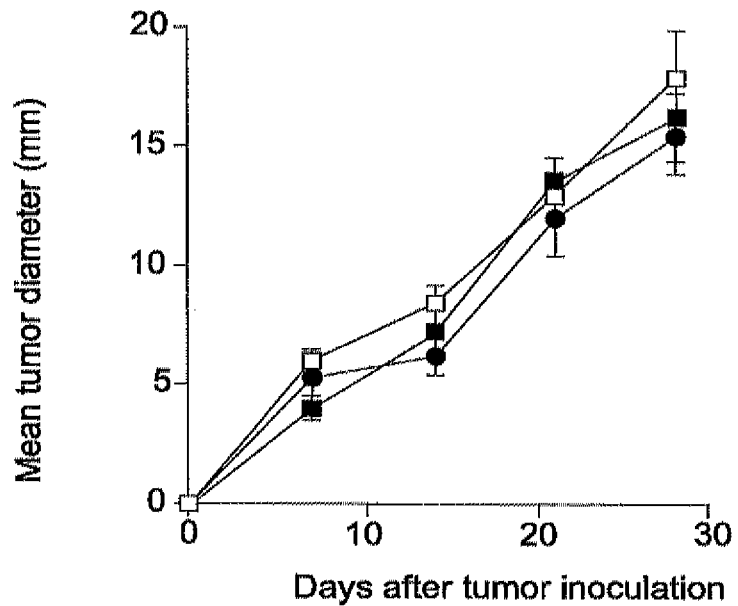
FIG. 11 is a line graph showing growth (mean tumor diameter in millimeters) of EG7 murine tumor cells that were either mock transfected (-□-) or transfected with wild-type B7-DC (-■-) or K113S 137-DC (-●-) in immunodeficient nude (nu/nu) mice as a function of time (days).

While these results suggest that expression of K113S B7-DC on tumor cells induces regression of tumor in immune competent mice, it is unclear whether this effect is mediated by immune system. To confirm this, K113S B7-DC cells were introduced into immune deficient nude mice subcutaneously. The results demonstrate that EG7/K113S cells has a similar growth rate as cells of the mock line and Wt B7-DC line, and tumors did not regress (FIG. 11). These results thus demonstrate that tumor regression is mediated by the immune system and the expression of K113S B7-DC stimulates potent immune responses.

Figure 12:
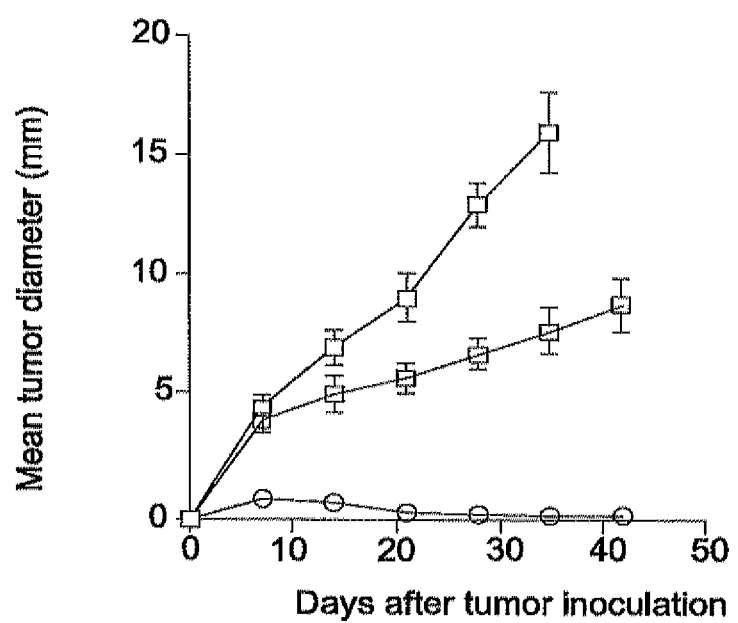
FIG. 12 is a line graph showing growth (mean tumor diameter in millimeters) of P815 mastrocytoma murine tumor cells that were either mock transfected (-□-) or transfected with wild-type B7-DC (-■-) or K113S B7-DC (-●-) in syngeneic immunocompetent (DBA/2) mice as a function of time (days).
Figure 13:
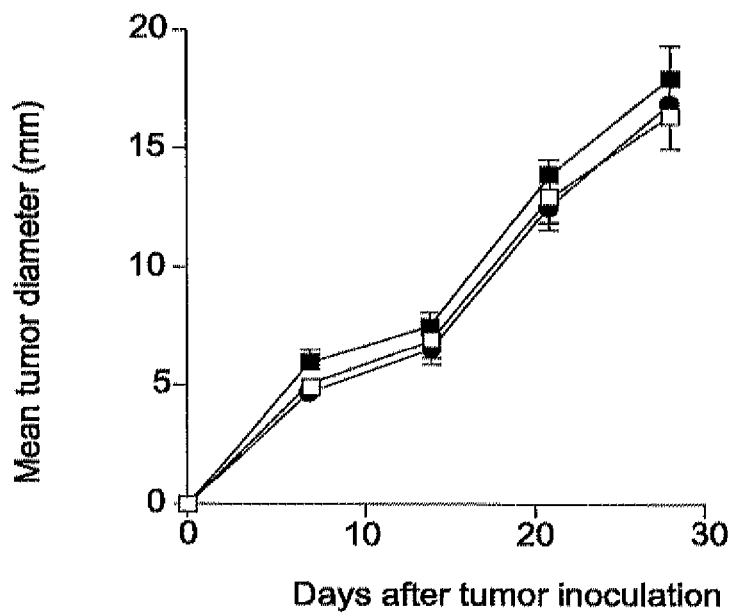
FIG. 13 is a line graph showing growth (mean tumor diameter in millimeters) of P815 mastrocytoma murine tumor cells that were either mock transfected (-□-) or transfected with wild-type B7-DC (-■-) or K113S B7-DC (-●-) in immunodeficient nude (nu/nu) mice as a function of time (days).

To demonstrate that stimulation of antitumor immunity by K113S B7-DC is not limited to EG7 tumor cells, similar experiment were performed using stably transfected murine P815 mastocytoma cells. K113S B7-DC, parental plasmid, as well as the plasmid containing Wt B7-DC were also transfected to establish control cell lines. Sublines of tumor cells expressing comparable levels of B7-DC were selected after flow cytometry analysis using specific antibody as described above. Similar to the EG7/K11S tumor line, subcutaneous inoculation of P815/K113S cells into 10 syngeneic immunocompetent DBA/2 mice induced transient growth, and all tumors regressed rapidly. Inoculation of mock-transfected P815 cells induced progressively growing tumors, while injection of P815/Wt B7-DC cells also induced progressively growing tumors. However, their growth was much slower than mock P815 line (FIG. 12). Inoculation of these tumor lines into immune deficient nu/nu mice induced growth of tumors at a similar rate (FIG. 13), supporting that immune system plays a role in growth resistance of B7-DC transfectant.

Example 5

Therapeutic Effect of B7-DCIg on Tumor Growth in Mice

To determine therapeutic effect of B7-DC protein on tumor growth, mice with established P815 tumors in immune competent mice were treated with B7-DCIg fusion proteins. Inoculation of wt P815 cells into mice induced progressive growing tumors. Injection of mice with 0.1 mg of B7-DCIg intraperitoneally at day 3 and 8 inhibited the growth of the tumors (FIG. 14).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A method for inducing an immune response to an antigen in a human subject comprising administering to the subject
   (a) an antigen, and
   (b) a fusion protein comprising a first fusion partner comprising a variant B7-DC polypeptide fused
      (i) directly to a second polypeptide or,
      (ii) fused to a linker peptide sequence that is fused to the second polypeptide,
   wherein the variant B7-DC polypeptide is an isolated variant of a wildtype human B7-DC polypeptide comprising an IgV domain of B7-DC comprising an amino acid substitution in the A', B, C, C', C", D, E, F, or G β strand of the wild-type human B7-DC polypeptide, and has altered affinity for PD-1 compared to the wild-type human B7-DC polypeptide.

2. The method of claim 1, wherein (a) is administered to the subject prior to (b).

3. The method of claim 1, wherein (b) is administered to the subject prior to (a).

4. The method of claim 1, wherein (a) and (b) are co-administered to the subject in an immunogenic composition.

5. The method of claim 4, wherein the immunogenic composition further comprises an adjuvant.

6. The method of claim 4, wherein the immunogenic composition further comprises a targeting molecule.

7. The method of claim 1, wherein the subject has cancer.

8. The method of claim 1, wherein the antigen is a soluble antigen.

9. The method of claim 1, wherein the antigen is a tumor antigen.

10. The method of claim 1, wherein the immune response is an increase antigen-specific proliferation of T cells, enhanced cytokine production by T cells, stimulation of differentiation, stimulation of an effector function of T cells, or increased survival of T cells in the subject compared to administering (a) alone.

11. A method for treating cancer in a human subject comprising administering to the subject
    (a) an antigen, and
    (b) a fusion protein comprising a first fusion partner comprising a variant B7-DC polypeptide fused
       (i) directly to a second polypeptide or,
       (ii) fused to a linker peptide sequence that is fused to the second polypeptide,
    wherein the variant B7-DC polypeptide is an isolated variant of a wildtype human B7-DC polypeptide comprising an IgV domain of B7-DC comprising an amino acid substitution in the A', B, C, C', C", D, E, F, or G β strand of the wild-type human B7-DC polypeptide, and has altered affinity for PD-1 compared to the wild-type human B7-DC polypeptide,
    wherein (a) and (b) are administered to the subject in an effective amount to reduce a symptom of the cancer.

12. The method of claim 11, wherein (a) is administered to the subject prior to (b).

13. The method of claim 11, wherein (b) is administered to the subject prior to (a).

14. The method of claim 11, wherein (a) and (b) are co-administered to the subject in an immunogenic composition.

15. The method of claim 14, wherein the immunogenic composition further comprises an adjuvant.

16. The method of claim 14, wherein the immunogenic composition further comprises a targeting molecule.

17. The method of claim 11, wherein the antigen is a soluble antigen.

18. The method of claim 11, wherein the antigen is a tumor antigen.

19. The method of claim 11 further comprising administering the subject a chemotherapeutic agent, a hormonal agent, a second immunostimulatory agent, or radiation therapy.

20. A method for increasing antigen-specific proliferation of T cells in a human subject comprising administering to the subject
    (a) an antigen, and
    (b) a fusion protein comprising a first fusion partner comprising a variant B7-DC polypeptide fused
       (i) directly to a second polypeptide or,
       (ii) fused to a linker peptide sequence that is fused to the second polypeptide,
    wherein the variant B7-DC polypeptide is an isolated variant of a wildtype human B7-DC polypeptide comprising an IgV domain of B7-DC comprising an amino acid substitution in the A', B, C, C', C", D, E, F, or G β strand of the wild-type human B7-DC polypeptide, and has altered affinity for PD-1 compared to the wild-type human B7-DC polypeptide,
    wherein (b) is administered in an effective amount to increase proliferation of T cells specific to the antigen in the subject compared to administrating the subject (a) alone.

21. A method for enhancing production of a cytokine by T cells in a human subject comprising administering to the subject
    (a) an antigen, and
    (b) a fusion protein comprising a first fusion partner comprising a variant B7-DC polypeptide fused
       (i) directly to a second polypeptide or,
       (ii) fused to a linker peptide sequence that is fused to the second polypeptide, wherein the variant B7-DC polypeptide is an isolated variant of a wildtype human B7-DC polypeptide comprising an IgV domain of B7-DC comprising an amino acid substitution in the A', B, C, C', C", D, E, F, or G β strand of the wild-type human B7-DC polypeptide, and has altered affinity for PD-1 compared to the wild-type human B7-DC polypeptide, wherein (b) is administered in an effective amount to enhance production of the cytokine by T cells in the subject compared to administrating the subject (a) alone.

22. The method of claim 21, wherein the cytokine is selected from the group consisting of Il-2, IL-4, IL-5, IL-6, IL-10, IL-13, and IFN-γ.

23. A method for increasing differentiation of T cells in a human subject comprising administering to the subject
(a) an antigen, and
(b) a fusion protein comprising a first fusion partner comprising a variant B7-DC polypeptide fused
(i) directly to a second polypeptide or,
(ii) fused to a linker peptide sequence that is fused to the second polypeptide,
wherein the variant B7-DC polypeptide is an isolated variant of a wildtype human B7-DC polypeptide comprising an IgV domain of B7-DC comprising an amino acid substitution in the A', B, C, C', C", D, E, F, or G β strand of the wild-type human B7-DC polypeptide, and has altered affinity for PD-1 compared to the wild-type human B7-DC polypeptide,
wherein (b) is administered in an effective amount to increase differentiation of T cells in the subject compared to administrating the subject (a) alone.

24. A method for increasing an effector function of T cells in a human subject comprising administering to the subject
(a) an antigen, and
(b) a fusion protein comprising a first fusion partner comprising a variant B7-DC polypeptide fused
(i) directly to a second polypeptide or,
(ii) fused to a linker peptide sequence that is fused to the second polypeptide,
wherein the variant B7-DC polypeptide is an isolated variant of a wildtype human B7-DC polypeptide comprising an IgV domain of B7-DC comprising an amino acid substitution in the A', B, C, C', C", D, E, F, or G β strand of the wild-type human B7-DC polypeptide, and has altered affinity for PD-1 compared to the wild-type human B7-DC polypeptide,
wherein (b) is administered in an effective amount to increase the effector function of T cells in the subject compared to administrating the subject (a) alone.

25. A method for increasing survival of T cells in a human subject comprising administering to the subject
(a) an antigen, and
(b) a fusion protein comprising a first fusion partner comprising a variant B7-DC polypeptide fused
(i) directly to a second polypeptide or,
(ii) fused to a linker peptide sequence that is fused to the second polypeptide,
wherein the variant B7-DC polypeptide is an isolated variant of a wildtype human B7-DC polypeptide comprising an IgV domain of B7-DC comprising an amino acid substitution in the A', 13, C, C', C", D, E, F, or G β strand of the wild-type human B7-DC polypeptide, and has altered affinity for PD-1 compared to the wild-type human B7-DC polypeptide,
wherein (b) is administered in an effective amount to increase survival of T cells in the subject compared to administrating the subject (a) alone.

* * * * *

UNITED STATES PATENT AND TRADEMARK OFFICE
CERTIFICATE OF CORRECTION

PATENT NO. : 8,445,447 B2
APPLICATION NO. : 13/413990
DATED : May 21, 2013
INVENTOR(S) : Lieping Chen Page 1 of 1

It is certified that error appears in the above-identified patent and that said Letters Patent is hereby corrected as shown below:

In the Claims:

Claim 10, column 53, line 50, replace "increase" with --increased--.
Claim 25, column 56, line 27, replace "A', 13, C," with --A', B, C--.

Signed and Sealed this
Third Day of September, 2013

Teresa Stanek Rea
*Acting Director of the United States Patent and Trademark Office*